US010351531B2

(12) United States Patent
Xiong et al.

(10) Patent No.: US 10,351,531 B2
(45) Date of Patent: *Jul. 16, 2019

(54) PYRAZOLE DERIVATIVES AS MODULATORS OF THE 5-HT$_{2A}$ SEROTONIN RECEPTOR USEFUL FOR THE TREATMENT OF DISORDERS RELATED THERETO

(71) Applicant: Arena Pharmaceuticals, Inc., San Diego, CA (US)

(72) Inventors: Yifeng Xiong, San Diego, CA (US); Martin C. Cherrier, Chicago, IL (US); Jin Sun Karoline Choi, San Diego, CA (US); Peter I. Dosa, San Diego, CA (US); Brian M. Smith, San Diego, CA (US); Sonja Strah-Pleynet, Newton, MA (US); Brett Ullman, San Diego, CA (US); Bradley Teegarden, San Diego, CA (US)

(73) Assignee: ARENA PHARMACEUTICALS, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/657,896

(22) Filed: Jul. 24, 2017

(65) Prior Publication Data

US 2017/0320831 A1 Nov. 9, 2017

Related U.S. Application Data

(63) Continuation of application No. 14/692,807, filed on Apr. 22, 2015, now Pat. No. 9,732,039, which is a continuation of application No. 12/444,098, filed as application No. PCT/US2007/021182 on Oct. 2, 2007, now Pat. No. 9,434,692.

(60) Provisional application No. 60/849,070, filed on Oct. 3, 2006.

(51) Int. Cl.
| C07D 231/16 | (2006.01) |
| C07D 403/14 | (2006.01) |
| C07D 403/12 | (2006.01) |
| C07D 403/06 | (2006.01) |
| C07D 231/54 | (2006.01) |
| C07D 405/04 | (2006.01) |
| C07D 231/14 | (2006.01) |

(52) U.S. Cl.
CPC ......... *C07D 231/16* (2013.01); *C07D 231/14* (2013.01); *C07D 231/54* (2013.01); *C07D 403/06* (2013.01); *C07D 403/12* (2013.01); *C07D 403/14* (2013.01); *C07D 405/04* (2013.01)

(58) Field of Classification Search
CPC .. C07D 231/14; C07D 403/06; C07D 403/12; C07D 403/14; C07D 231/54; C07D 231/16; C07D 405/04
See application file for complete search history.

(56) References Cited

U.S. PATENT DOCUMENTS

| 4,099,012 A | 4/1978 | Gschwend |
| 4,405,644 A | 9/1983 | Kabbe et al. |
| 4,409,231 A | 10/1983 | Stenzel et al. |
| 4,482,534 A | 11/1984 | Blank |
| 4,555,399 A | 11/1985 | Hsiao |
| 4,985,352 A | 1/1991 | Julius et al. |
| 5,077,409 A | 12/1991 | Wissner |
| 5,128,351 A | 7/1992 | Wissner |
| 5,346,906 A | 9/1994 | Baker et al. |
| 5,523,280 A | 6/1996 | Chene et al. |

(Continued)

FOREIGN PATENT DOCUMENTS

| CA | 2135253 A1 | 5/1996 |
| DE | 102004061593 A1 | 6/2006 |

(Continued)

OTHER PUBLICATIONS

Fujiwara, Augmented Responses to 5-HT2-Receptor-Mediated Vascoconstrictions in Atherosclerotic Rabbit Common Carotid Arteries, (1995) Journal of Cardiovascular Pharmacology 26:503-510.

(Continued)

*Primary Examiner* — Alexander R Pagano
*Assistant Examiner* — Ebenezer O Sackey
(74) *Attorney, Agent, or Firm* — Pepper Hamilton LLP

(57) ABSTRACT

Pyrazole derivatives of Formula (Ia) and pharmaceutical compositions thereof that modulate the activity of the serotonin 5HT$_{2A}$ receptor. Formula (Ia). Compounds and pharmaceutical compositions thereof are directed to methods useful in the treatment of insomnia and related sleep disorders, platelet aggregation, coronary artery disease, myocardial infarction, transient ischemic attack, angina, stroke, atrial fibrillation, reducing the risk of blood clot formation, asthma or symptoms thereof, agitation or symptoms thereof, behavioral disorders, drug induced psychosis, excitative psychosis, Gilles de la Tourette's syndrome, manic disorder, organic or NOS psychosis, psychotic disorders, psychosis, acute schizophrenia, chronic schizophrenia, NOS schizophrenia and related disorders, diabetic-related disorders, progressive multifocal leukoencephalopathy and the like. The present invention also relates to the methods for the treatment of 5-HT$_{2A}$ serotonin receptor mediated disorders in combination with other pharmaceutical agents administered separately or together.

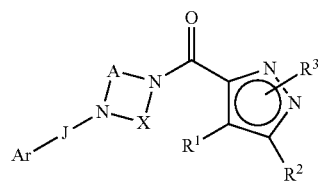

(Ia)

22 Claims, 6 Drawing Sheets

(56) References Cited

U.S. PATENT DOCUMENTS

| | | |
|---|---|---|
| 5,661,024 A | 8/1997 | Kao et al. |
| 5,856,326 A | 1/1999 | Anthony et al. |
| 5,861,431 A | 1/1999 | Hildebrand et al. |
| 5,885,785 A | 3/1999 | Kao et al. |
| 5,886,044 A | 3/1999 | Widdowson et al. |
| 5,905,080 A | 5/1999 | Duckworth et al. |
| 5,945,382 A | 8/1999 | Cantegril et al. |
| 5,990,133 A | 11/1999 | Gaster et al. |
| 6,005,008 A | 12/1999 | Widdowson et al. |
| 6,028,083 A | 2/2000 | Carr et al. |
| 6,028,085 A | 2/2000 | Bromidge |
| 6,063,808 A | 5/2000 | Fabiano et al. |
| 6,107,324 A | 8/2000 | Behan et al. |
| 6,110,498 A | 8/2000 | Rudnic et al. |
| 6,140,509 A | 10/2000 | Behan et al. |
| 6,180,138 B1 | 1/2001 | Engh et al. |
| 6,271,261 B1 | 8/2001 | Widdowson |
| 6,284,269 B1 | 9/2001 | Struengmann et al. |
| 6,297,261 B1 | 10/2001 | Christophersen et al. |
| 6,358,698 B1 | 3/2002 | Weiner et al. |
| 6,383,762 B1 | 5/2002 | Kao et al. |
| 6,417,393 B1 | 7/2002 | Christophersen et al. |
| 6,420,541 B1 | 7/2002 | Behan et al. |
| 6,469,006 B1 | 10/2002 | Blair et al. |
| 6,479,480 B1 | 11/2002 | Moyes et al. |
| 6,479,519 B1 | 11/2002 | Astles et al. |
| 6,531,291 B1 | 3/2003 | Kabbash et al. |
| 6,541,209 B1 | 4/2003 | Behan et al. |
| 6,541,477 B2 | 4/2003 | Goehring et al. |
| 6,696,475 B2 | 2/2004 | Dahl et al. |
| 6,706,749 B2 | 3/2004 | Dahl et al. |
| 6,753,442 B1 | 6/2004 | Benedini et al. |
| 6,784,183 B2 | 8/2004 | Lavielle et al. |
| 6,846,919 B2 | 1/2005 | Behan et al. |
| 7,091,236 B1 | 8/2006 | Roberts et al. |
| 7,368,539 B2 | 5/2008 | Behan et al. |
| 7,754,724 B2 | 7/2010 | Lorsbach et al. |
| 8,481,535 B2 | 7/2013 | Gharbaoui et al. |
| 9,034,911 B2 | 5/2015 | Selvey et al. |
| 9,434,692 B2 * | 9/2016 | Xiong .................. C07D 231/14 |
| 9,732,039 B2 * | 8/2017 | Xiong .................. C07D 231/14 |
| 2001/0022963 A1 | 9/2001 | Klaveness et al. |
| 2002/0025965 A1 | 2/2002 | Lavielle et al. |
| 2002/0025967 A1 | 2/2002 | Smith |
| 2002/0098548 A1 | 7/2002 | Kao et al. |
| 2003/0037274 A1 | 2/2003 | Shikata et al. |
| 2004/0077654 A1 | 4/2004 | Bouillot et al. |
| 2004/0082644 A1 | 4/2004 | Korsten |
| 2004/0092528 A1 | 5/2004 | Kelly et al. |
| 2004/0102636 A1 | 5/2004 | Miller et al. |
| 2005/0054691 A1 | 3/2005 | Potter et al. |
| 2005/0080124 A1 | 4/2005 | Teegarden et al. |
| 2005/0215526 A1 | 9/2005 | Hulme et al. |
| 2005/0267097 A1 | 12/2005 | Pinto et al. |
| 2006/0014705 A1 | 1/2006 | Howitz et al. |
| 2006/0018839 A1 | 1/2006 | Ieni et al. |
| 2006/0063754 A1 | 3/2006 | Edgar et al. |
| 2006/0142241 A1 | 6/2006 | Yoo |
| 2006/0172992 A1 | 8/2006 | Yokoyama et al. |
| 2006/0205792 A1 | 9/2006 | Wong et al. |
| 2006/0229335 A1 | 10/2006 | Teegarden et al. |
| 2007/0004750 A1 | 1/2007 | Lorsbach et al. |
| 2007/0037827 A1 | 1/2007 | Nunes et al. |
| 2007/0043058 A1 | 2/2007 | Bang-Anderson et al. |
| 2007/0072857 A1 | 3/2007 | Teegarden et al. |
| 2007/0078134 A1 | 4/2007 | Teegarden et al. |
| 2007/0207994 A1 | 9/2007 | Teegarden et al. |
| 2007/0244086 A1 | 10/2007 | Teegarden et al. |
| 2007/0293685 A1 | 12/2007 | Fritch et al. |
| 2008/0015223 A1 | 1/2008 | Strah-Pleynet et al. |
| 2008/0114014 A1 | 5/2008 | Rich |
| 2008/0194836 A1 | 8/2008 | Gharbaoui et al. |
| 2008/0200530 A1 | 8/2008 | Unett et al. |
| 2009/0053306 A1 | 2/2009 | Agarwal et al. |
| 2009/0076254 A1 | 3/2009 | Behan et al. |
| 2009/0186895 A1 | 7/2009 | Teegarden et al. |
| 2009/0197935 A1 | 8/2009 | Teegarden et al. |
| 2010/0004264 A1 | 1/2010 | Xiong et al. |
| 2010/0069367 A1 | 3/2010 | Boren et al. |
| 2010/0240653 A1 | 9/2010 | Santora et al. |
| 2011/0207790 A1 | 8/2011 | Carlos et al. |
| 2011/0207791 A1 | 8/2011 | Selvey et al. |
| 2011/0263592 A1 | 10/2011 | Xiong et al. |
| 2012/0088785 A1 | 4/2012 | Rich |
| 2013/0172379 A1 | 7/2013 | Rich |
| 2013/0172398 A1 | 7/2013 | Rich |
| 2013/0217700 A1 | 8/2013 | Xiong et al. |
| 2013/0237541 A1 | 9/2013 | Teegarden et al. |
| 2014/0142140 A1 | 5/2014 | Bird |
| 2015/0031897 A1 | 1/2015 | Rich |
| 2015/0045372 A1 | 2/2015 | Krishnan et al. |
| 2015/0073141 A1 | 3/2015 | Teegarden et al. |
| 2015/0210648 A1 | 7/2015 | Carlos et al. |
| 2015/0320742 A1 | 11/2015 | Chuang et al. |
| 2016/0067216 A1 | 3/2016 | Selvey et al. |
| 2016/0075660 A1 | 3/2016 | Kiong et al. |
| 2017/0014385 A1 | 1/2017 | Friedhoff et al. |
| 2017/0042876 A1 | 2/2017 | Mills et al. |

FOREIGN PATENT DOCUMENTS

| | | |
|---|---|---|
| EP | 0371431 A2 | 11/1989 |
| EP | 1108720 B1 | 12/2000 |
| EP | 1683516 A2 | 1/2006 |
| EP | 1695966 A1 | 8/2006 |
| EP | 1727803 B1 | 3/2012 |
| EP | 2190844 B1 | 4/2013 |
| EP | 2066641 B1 | 6/2014 |
| FR | 2722369 A | 1/1996 |
| GB | 1147379 A | 4/1969 |
| JP | 04334357 B2 | 3/2010 |
| WO | 1996002138 A1 | 2/1996 |
| WO | 1996010559 A1 | 4/1996 |
| WO | 1996023783 A1 | 8/1996 |
| WO | 1996032931 A2 | 10/1996 |
| WO | 1997003967 A1 | 2/1997 |
| WO | 1997045111 A1 | 12/1997 |
| WO | 1998024785 A1 | 6/1998 |
| WO | 1999006354 A1 | 2/1999 |
| WO | 1999032436 A1 | 7/1999 |
| WO | 1999032463 A1 | 7/1999 |
| WO | 1999032927 A1 | 7/1999 |
| WO | 1999052927 A1 | 10/1999 |
| WO | 2000057877 A1 | 10/2000 |
| WO | 2000064866 A1 | 11/2000 |
| WO | 2001007436 A1 | 2/2001 |
| WO | 2001021160 A1 | 3/2001 |
| WO | 2001029008 A1 | 4/2001 |
| WO | 2001046166 A2 | 6/2001 |
| WO | 2001064676 A1 | 9/2001 |
| WO | 2002039987 A1 | 5/2002 |
| WO | 2002051833 A2 | 7/2002 |
| WO | 2002076464 A1 | 10/2002 |
| WO | 2003002097 A2 | 1/2003 |
| WO | 2003062206 A2 | 7/2003 |
| WO | 2004028450 A2 | 4/2004 |
| WO | 2004045118 A2 | 5/2004 |
| WO | 2004046110 A1 | 6/2004 |
| WO | 2004058722 A1 | 7/2004 |
| WO | 2004071426 A2 | 8/2004 |
| WO | 2004085433 A2 | 10/2004 |
| WO | 2004096771 A1 | 11/2004 |
| WO | 2005012254 A1 | 2/2005 |
| WO | 2005021545 A1 | 3/2005 |
| WO | 2005077345 A1 | 8/2005 |
| WO | 2005103011 A1 | 11/2005 |
| WO | 2006049734 A2 | 2/2006 |
| WO | 2006018662 A2 | 5/2006 |
| WO | 2006049941 A2 | 5/2006 |
| WO | 2006060654 A1 | 6/2006 |
| WO | 2006070394 A1 | 7/2006 |
| WO | 2006076592 A1 | 7/2006 |
| WO | 2006078610 A1 | 7/2006 |
| WO | 2006079637 A1 | 8/2006 |

(56) References Cited

FOREIGN PATENT DOCUMENTS

| WO | 2006081335 A1 | 8/2006 |
|---|---|---|
| WO | 2006086705 A1 | 8/2006 |
| WO | 2006089871 A1 | 8/2006 |
| WO | 2006095205 A1 | 9/2006 |
| WO | 2006097766 A1 | 9/2006 |
| WO | 2006100519 A1 | 9/2006 |
| WO | 2006112464 A1 | 10/2006 |
| WO | 2006116614 A1 | 11/2006 |
| WO | 2007002559 A1 | 1/2007 |
| WO | 2007026959 A1 | 3/2007 |
| WO | 2007041409 A1 | 4/2007 |
| WO | 2007129111 A1 | 11/2007 |
| WO | 2007136680 A1 | 11/2007 |
| WO | 2007136689 A1 | 11/2007 |
| WO | 2007136703 A1 | 11/2007 |
| WO | 2007136875 A1 | 11/2007 |
| WO | 2008027483 A1 | 3/2008 |
| WO | 2008042388 A1 | 4/2008 |
| WO | 2008054748 A1 | 5/2008 |
| WO | 2009023253 A1 | 2/2009 |
| WO | 2009123714 A1 | 10/2009 |
| WO | 2010062321 A1 | 6/2010 |
| WO | 2010062323 A1 | 6/2010 |
| WO | 2014065437 A1 | 5/2014 |
| WO | 2015012554 A1 | 1/2015 |

OTHER PUBLICATIONS

Gill et al., A Prescribing Cascade Involving Cholinesterase Inhibitors and Anticholinergic Drugs, (2005) Arch Intern Med 165:808-813.
Gish et al., Memorandum: Age-dependent manifestations of central anticholinergic effects, Department of Health and Human Services Public Health Service Food and Drug Administration Center for Drug Evaluation and Research, Mar. 5, 2007.
Glennon et al., Behavioral and Serotonin receptor properties of 4-substituted Derivatives of the Hallucinogen 1-2,5-dimethoxyphenyl)-2-aminopropane, (1982) J. Med. Chem. 25(10):1163-1168.
Gottlieb et al., NMR Chemical Shifts of Common Laboratory Solvents as Trace Impurities, (1997) J. Org. Chem. 62:7512-7515.
Greene et al., Protecting Groups in Organic Synthesis, 3rd Edition, 1999 (Wiley) (abstract).
Griesser, The Importance of Solvates, in Polymorphism in the Pharmaceutical Industry, 211-233; Rolf Hilfiker, ed., 2006.
Grotewiel et al., Receptors Exhibit Constitutive Activity that is Blocked by Inverse Agonists, (May 21-25, 1994) Faseb J., Abstract 353:8(7) (1 page).
Grunder et al., Time course of 5-HT2A receptor occupancy in the human brain after a single oral dose of the putative antipsychotic drug MDL 100,907 measured by positron emission tomography, (Sep. 1997) Neuropsychopharmacology 17(3):175-185.
Guillory, Generation of Polymorphs, Hydrates, Solvates, and Amorphous Solids, in Polymorphism in the Pharmaceutical Industry, (1999) Harry G. Britain ed. 183-226, 202-209.
Gutsche et al., 2-Phenylcycloheptanone, (1963) Org. Syn. Coll. 4:780-783.
Halberstadt et al., 5-HT2A and 5-HT2C Receptors Exert Opposing Effects on Locomotor Activity in Mice, (Jul. 2009) Neuropsychopharmacology 34(8):1958-1967.
Hashimoto et al., Urinary Incontinence: an Unrecognised Adverse Effect with Donepezil, (Aug. 12, 2000) The Lancet 356:568 (abstract).
Hayashi et al., Sarpogrelate HCl, a selective 5-HT2A Antagonist, Retards the Progression of Atherosclerosis Through a Novel Mechanism, (2003) Atherosclerosis 168:23-31.
Herrick-Davis et al., Activating mutations of the serotonin 5-HT2C receptor, (Sep. 1997) J. Neurochem 69(3):1138-44.
Herrick-Davis et al., Constitutively active 5HT2C serotonin receptor created by site-directed mutagenesis, Society for Neuroscience Abstracts 22:699.18.

Higuchi et al., Pro-Drugs as Novel Delivery Systems, vol. 14 of the ACS Symposium Series; and in Bioreversible Carriers in Drug Design, ed. Edward B. Roche, American Pharmaceutical Association and Pergamon Press, 1987.
Hittner et al., A Selective 5-HT.sub.2A Receptor Inverse Agonist with Preclinical Antipsychotic Profile in Rats, 2000 Neuro, poster.
Holtje, Pharmacophore Identification and Receptor Mapping, (2003) The Practice of Medicinal Chemistry, 2nd ed., Wermuth (editor), Academic Press, Chap. 24, pp. 387-403.
Horibe et al., Sarpogrelate, a 5-HT2 Receptor Blocker, may Have a Preconditioning-Like Effect in Patients with Coronary Artery Disease, (2004) Circulation Research 68:68-72.
ICSD—International Classification of Sleep Disorders: Revied Diagnostic and Coding Manual, American Academy of Sleep Medicine (2001) pp. 1-336 (also includes table of contents and glossary.
Ieni et al., The 5-HT1A Receptor Probe[3H]8-OH-DPAT Labels. The 5-HT Transporter in Human Platelets, (1988) Life Sciences 42:311-320.
Ikeguchi et al., Mianserin Treatment of Patients with Psychosis Induced by Antiparkinsonian Drugs, (1995) Eur. Arch. Psych. Clin. Neurosci. 244:320-324.
International Preliminary Report on Patentability for International Application No. PCT/US2005/041726 dated Sep. 21, 2006.
International Preliminary Report on Patentability for International Application No. PCT/US2007/011810 dated Jul. 16, 2008.
International Preliminary Report on Patentability; PCT/US2007/021182 dated Nov. 4, 2008.
International Search Report and Written Opinion for PCT/US2004/023880 dated Nov. 15, 2004.
International Search Report and Written Opinion for PCT/US2007/021182 dated Mar. 14, 2005.
International Search Report and Written Opinion for PCT/US2008/009740 dated Feb. 18, 2009.
International Search Report and Written Opinion for PCT/US2009/005811 dated Jul. 8, 2010.
International Search Report and Written Opinion for PCT/US2009/005809 dated Apr. 28, 2010.
International Search Report and Written Opinion for PCT/US2016/037090 dated Sep. 9, 2016.
International Search Report for International Application No. PCT/US2006/002721 dated Feb. 20, 2007.
International Search Report for International Application No. PCT/US2005/041726 dated May 18, 2006.
International Search Report for International Application No. PCT/US2006/001516 dated Jun. 7, 2006.
International Search Report for International Application No. PCT/US2007/011810 dated Oct. 30, 2007.
Janos et al., Overactive bladder medicines and cognitive testing, (Nov. 2008) Int J Clin Pract 62(11):1637-1642 (abstract).
Jayakumar et al., Synthesis and SAR of Alkoxyphenyl Pyrazole as 5-HT2A Inverse Agonists, (2006) ACS, 232nd ACS National Meeting, Medi 430, poster.
Jayakumar et al., Synthesis and SAR of Novel-Phenyl-Pyrazole Urea derivatives, (2006) ACS, abstract.
Jayakumar et al; Synthesis and SAR of Substituted Diphenylamines as 5HT2A Inverse-Agonists, (2004) ACS, meeting abstract.
Jayakumar et al; Synthesis and Sar of Substituted Diphenylamines as 5HT2A Inverse-Agonists, (2005) ACS, 229th ACS National Meeting, Medi 049, poster.
Jeon et al., The synthesis of a new pyrazolylimidazolinone via 1,3-dipolar cycloaddition reaction of N-methyl sydnone with methyl propiolate, (1998) Bull. Korean Chem. Soc. 19(7):725-726.
Jewart et al., Cognitive, Behavioral and Physiological Changes in Alzheimer Disease Patients as a Function of Incontinence Medications, (Apr. 2005) Am J Geriatr Psychiatry 13(4):324-328 (abstract).
Johnell et al., Concurrent Use of Anticholinergic Drugs and Cholinesterase Inhibitors, (2008) Drugs Aging 25 (10):871-877 (abstract).
Julius et al., The 5HT2 Receptor Defines a Family of Structurally Distinct but Functionally Conserved Serotonin Receptors, (1990) PNAS USA 87:928-932.

(56) References Cited

OTHER PUBLICATIONS

Kanayama et al., New treatment of lumbar disc herniation using 5-hydroxytryptamine.sub.2a receptor inhibitor: a randomized controlled trial, (2005) Journal of Neurosurgery: Spine 2:441-446.
Kaneniwa et al., Solubilization of Water-Insoluble Organic Powders by Ball-Milling in the Presence of Polyvinylpyrrolidone, (1975) Chem. Pharm. Bull. 23(11):2973-2986.
Katz et al., Comparison of risperidone and placebo for psychosis and behavioral disturbances associated with dementia: a randomized, double-blind trial. Risperidone Study Group, (Feb. 1999) J Clin Psychiatry. 60(2):107-15.
Kay et al., Antimuscarinic Drugs for Overactive Bladder and Their Potential Effects on Cognitive Function in Older Patients, (2005) JAGS 53:2195-2201 (abstract).
Kay et al., Preserving cognitive function for patients with overactive bladder: evidence for a differential effect with darifenacin, (Nov. 2008) Int J Clin Pract. 62(11):1792-1800.
Adams et al., Antithrombotic and Vascular effects of AR246686, a novel 5-HT2A receptor antagonist, 2007 EJM, pp. 1-22.
Affolter, H., CA2+ as Messenger of 5HT2-Receptor Stimulation in Human Blood Platelets, (1984) Naunyn Schmiedebergs Arch. Pharmacol. 325(4):337-42.
Al-Shamma, APD125: A 5-HT2A Inverse Agonist for the Treatment of Sleep Maintenance Insomnia, 2008 DDST 1-7.
Al-Shamma et al, The Selective Serotonin 5HT2A Inverse Agonist APD125 Promotes Sleep Onset and Consolidation in Male Wistar Rats During the Normal Active Phase, (2005) APSS Abstract 0005.
Al-Shamma et al., Nelotanserin, a Novel Selective Human 5-Hydroxytryptamine2A Inverse Agonist for the Treatment of Insomnia, (2010) J. Pharmacol. Exp. Ther. 332:281-290.
Al-Shamma et al; The Selective Serotonin 5HT2A Inverse Agonist APD125 Promotes Sleep Onset and Consolidation in Male Wistar Rats During the Normal Active Phase, 1994 APSS Slides, 1-5.
Andrzejewska-Buczko et al. [Serotonin in diabetic retinopathy], Klin Oczna. Feb. 1996;98(2):101-4 (abstract).
Anonymous, Prevention of Atherosclerotic Complications: Controlled Trial of Ketanserin, (1989) Br. Med. J. 298:424-430.
Antinori et al., Diagnosis of AIDS-related Focal Brain Lesions: A decision-making analysis based on clinical and neuroadiiologic characteristics combined with polymerase chain reaction assays in CSF, (1997) Neurology 48:687-694.
Arena Pharmaceuticals Announces Preliminary Results of Phase 2b Clinical Trial of APD125 for the Treatment of Insomnia, PRNewswire-FirstCall via Comtex News NetWork, Press Release dated Dec. 9, 2008.
Barluenga, Jr. et al., A New and Specific Method for the Monomethylation of Primary Amines, (1984) J. Chem. Soc. Chem. Commun. 20:1334-1335.
Batey et al., An Efficient New Protocol for the Formation of Unsymmetrical Tri- and Tretrasubstituted Ureas, (1998) Tetra. Lett. 39:6267-6270.
Berge et al., Pharmaceutical salts, (1977) J. of Pharmaceutical Sciences 66(1):1-19.
Berger et al., Progressive Multifocal Leukoencephalopathy, (1999) Seminars in Neurology 19:193-200.
Bernatowicz et al., A Comparison of Acid Labile Linkage Agents for the Synthesis of Peptide C-Terminal Amides, (1989) Tetra. Let. 30(35):4645-4648.
Blier et al., Putative mechanisms of action of antidepressant drugs in affective and anxiety disorders and pain, (2001) Journal of Psychiatry and Neuroscience 26(1):37-43.
Burger, Isosterism and bioisosterism in drug design, (1991) Prog. Drug Res. 37:287-371 (abstract).
Burla et al., SIR2004: an improved tool for crystal structure determination and refinement, (2005) J. Appl. Cryst. 38: 381-388 (abstract).
Buysse et al.,The Pittsburgh Sleep Quality Index: A New Instrument for Psychiatric Practice and Research, (1989) Psychiatry Research 28(2):193-213.

Byrn, Solid-State Chemistry of Drugs, 2nd Ed. (1999), Chapter 11—Hydrates and Solvates, 233-247 (TOC).
Byrn et al., Pharmaceutical Solids: A Strategic Approach to Regulatory Considerations, (1995) Pharm. Res. 12 (7):945-954 (abstract).
Cameron et al., The effects of 5-hydroxytryptamine 5-HT2 receptor antagonists on nerve conduction velocity and endoneurial perfusion in diabetic rats, (Jun. 2003) Naunyn Schmiedebergs Arch Pharmacol. 367(6):607-614.
Carter et al., Carbobenzoxy Chloride and Derivatives, (1995) Org. Syn. Coll. 3:167-169.
Casey et al., Constitutively active mutant 5HT2, serotonin receptors: inverse agonist activity of classical 5HTsub antagonists, (1996) Society for Neuroscience Abstracts 22:699 (abstract).
Catalan et al., New Ultraviolet Stabilizers: 3- and 5-(2'-Hydroxyphenyl)pyrazoles, (1992) J. Am. Chem. Soc. 114:5039-5048.
Cazzola et al., Central 5-HT1A Receptors and Vagal Tone to the Airways, (2000) Trends Pharmacol. Sci. 21:201-202.
Chambers et al., Translocation of the 5-Alkoxy Substituent of 2,5-Dialkoxyarylalkylamines to the 6-Position: Effect of 5-HT2A/2C Receptor Affinity, (2002) Bioog. Med. Chem. Lett. 12:1997-1999.
Chang et al., Isapirone and Ketanserin Protects Against Circulatory Shock, Intracranial Hypertension, and Cerebral Ischemia During Heatstroke, (2005) Shock 24(4): 336-340.
Chang et al., Mechanism of the ocular hypotensive action of ketanserin, (1985, Summer) J. Ocul Pharmacol. 1(2):137-147.
Cohen-Mansfield et al., Agitated behaviors in the elderly. I. A conceptual review, (Oct. 1986) J Am Geriatr Soc. 34(10):711-21.
Collier et al., Radiosynthesis and in-vivo evaluation of the pseudopeptide 6-opioid antagonist [125I]-ITIPP (PSI), (1999) Labeled Compd. Radiopharm. 42:S264-S266.
Collins et al., N-Phenylamidines as Selective Inhibitors of Human Neuronal Nitric Oxide Sythase: Structure-Activity Studies and Demonstration of in Vivo Activity, (1998) J. Med. Chem., Amer. Chem. Soc. 41(15):2858-2871.
Cooke, Glycopyrrolate in Bladder Dysfunction, Jan. 1, 1983 South African Medical Journal 63(1):3 (abstract).
CUVPOSA glycopyrrolate oral solution Product Information Sheet, Rev. Jul. 2010.
Database Beilstein [Online] Beilstein Institute for Organic Chem., Frankfurt-Main, DE; XP002535545 Database Accession No. 5926580 (BRN), the whole document.
De Bie et al., Modulation of airway hyperresponsiveness and eosinophilia by selective histamine and 5-HT receptor antagonists in a mouse model of allergic asthma, (1998) British Journal of Pharmacology 124:857-864.
Defilippi et al., Drug Interactions with Cholinesterase Inhibitors, (2003) Drugs Aging 20(6):437-444 (abstract).
Deuchar et al., The role of 5-hydroxytryptamine in the control of pulmonary vascular tone in a rabbit model of pulmonary hypertension secondary to left ventricular dysfunction, (2005) Pulm. Pharmacol. Ther. 18(1):23-31.
Diagnostic and Statistical Manual of Mental Disorders, Fourth Edition, Text Revision: DSM-IV-TR, Washington, DC, American Psychiatric Association, 2000 (abstract).
Dosa et al., Solubilized phenyl-pyrazole ureas as potent, selective 5-HT2A inverse-agonists and their application as antiplatelet agents, (2010) BMCL pp. 1-15.
Dosa et al., Synthesis and Sar of Pyridinyl-Pyrazole Derivatives as Selective 5HT2A Inverse-Agonists for Platelet Aggregation, 2008 ACS, 235th ACS National Meeting, Medi 44, poster.
Dosa et al., Synthesis and SAR of solubilized pyrazole derivatives as 5-HT2A inverse-agonists for platelet aggregation, 232nd ACS National Meeting, Sep. 2006, Medi 431, 1 page (abstract).
Dosa et al., Synthesis and SAR of Solubilized Pyrazole Derivatives as 5HT2A Inverse-Agonists for Platelet Aggregation, 2006 ACS 232nd ACS National Meeting, Medi 431, poster.
Drinka, Antimuscarinic Drugs for Overactive Bladder and Their Potential Effects on Cognitive Function in Older Patients, 2006 JAGS 54(6):1004-1005 (abstract).

(56) References Cited

OTHER PUBLICATIONS

Edwards et al., Risk of delirium with concomitant use of tolterodine and acetycholinesterase inhibitors, 2002 J Amer Geriatric Society 50(6):1165-1166 (abstract).
Elliott et al., 4-Oxospiro[benzopyran-2,4'-piperidines] as Class III Antiarrhythmic Agents. Pharmacological Studies an 3,4-Dihydro-1'-[2-(benzofurazan-5-yl)-ethyl]-6methanesulfonamidospiro[(2H-)-1-benzopyran-2,4'-piperidin]-4-one (L-691,121) (1992) J. Med. Chem. 35:3973-3976.
Elphick et al., The human polyomavirus, JCV, uses serotonin to infect cells, (2004) Science 306:1380-1383.
European Search Report for EP05025004.2 dated Jun. 30, 2006.
Ferguson, Modulation of lymphatic smooth muscle contraction responses by the endothelium, (1992) Journal of Surgical Research 52:359-363 (abstract).
Fujita et al., Sarpogrelate Treatment Reduces Restenosis After Coronary Stenting, (2003) Am. Heart J. 145:e16.
Kitagawa et al., Beckmann Rearrangement of O-4 Pentenyl Oxime through N-Bromosuccinimide-Mediated Activating Process, (1997) Chem. Pharm. Bull. 45(1) 32-35.
Konig et al., A New Method for Synthesis of Peptides: Activation of the Carboxyl Group with Dicyclohexylcarbodiimide using 1-Hydroxybenzotriazoles as Additives, (1970) Chem. Ber. 103:788-798 (English abstract included).
Koss et al., Assessing patterns of agitation in Alzheimer's disease patients with the Cohen-Mansfield Agitation Inventory. The Alzheimer's Disease Cooperative Study, (1997) Alzheimer Dis Assoc Disord. 11(Suppl 2):545-550.
Krieger et al., Novel Immunosuppressants, (2004) Pediatr. Transplantation 8:594-599.
Krystal et al., The effects of APD125, a selective serotonin 5-HT2A, on sleep quality and sleep maintenance in a subjective study in patients with primary insomnia, (2009) Sleep pp. 1-23.
Kubinyi, 3D QSAR in Drug Design: Ligand-Protein Interactions and Molecular Similarity, (1998) Springer, 800 pages. p. 2-3:243 (abstract).
Landolt et al., Serotonin-2 receptors and human sleep: effect of a selective antagonist on EEG power spectra, (1999), Neuropsychopharmacology 21(3):455-66.
Le Bas et al., Radioiodinated analogs of EP 00652218 for the exploration of the tachykinin NK1 receptor by spect, (2001) J. Labeled Compd. Radiopharm. 44:S280-S282.
Levin et al., Direct measurement of the anticholinergic activity of a series of pharmacological compounds on the canine and rabbit urinary bladder, (1982) J. Urology 128(2):396-398 (abstract).
Lewy Body Dementia Association, Inc., treatment options page, http://www.lbda.org/content/treatment-options, at least as early as Apr. 10, 2015.
Lopez et al., Predictors of progression in patients with AD and Lewy bodies, (2000) Neurology 54:1774-1779 (abstract).
Lu et al., Chronic Exposure to Anticholinergic Medications Adversely Affects the Course of Alzheimer Disease, (Jul.-Aug. 2003) Am J Geriatr Psychiatry 11(4):458-461 (abstract).
Luthringer et al., Pharmacokinetic and Pharmacodynamic Effects of the Selective 5HT.sub.2A Inverse Agonist APD125 in Healthy Adults, 2005 APSS, abstract.
Major et al., Establishment of a Line of Human Fetal Glial Cells That Supports JC Virus Multiplication, (1985) PNAS USA 82:1257-1261.
Mandel, Statistical Analysis of Experimental Data, Chapter 3, pp. 28-57, Toronto, Ontario, (1964).
Mandel, Statistical Analysis of Experimental Data, Chapter 9, pp. 204-207, Toronto, Ontario, (1964).
Marchini et al., Sodium Borohydride-Carboxylic Acid Systems. Useful Reagents for the Alkylation of Amines, (1975) J. Org. Chem. 40(23):3453-3456.
Marcos, Serotonin-Induced Smooth Muscle Hyperplasia in Various Forms of Human Pulmonary Hypertension, (2004) Circ. Res. 94(9):1263-1270.
Mastropasqua et al., Ocular hypotensive effect of ketanserin in patients with primary open angle glaucoma, (1997) Acta Ophthalmol Scand Suppl. (224):24-5.
McKeith et al., Efficacy of rivastigmine in dementia with Lewy bodies: a randomised, double-blind, placebo-controlled international study, (2000) The Lancet 356:2031-2036 (abstract).
MedlinePlus, MedlinePlus Medical Encyclopedia, 2009, pp. 1-5 (abstract).
Menzaghi et al., AR116081(or AR116082)?, A Novel Selective 5-HT2A Inverse Agonist as a Putative Atypical Antipsychotic: Comparative Studies with Clozapine and Haloperidol, 2000 CINP, poster.
Menzaghi et al., AR116081, A Novel High Affinity 5-HT2A Receptor Inverse Agonist With in Vivo Efficacy, Nov. 1999 Neuro, poster.
Menzaghi et al., Identification of Novel Selective 5-HT2A Inverse Agonists as Putative Atypical Antipsychotics Using Constitutively Activated Human 5-HT Receptors, Jun. 2000 Aspet, poster.
Menzaghi et al., Therapeutic Potential of Selective Serotonin 5HT2A Receptor Inverse Agonists: Pre-Clinical Evaluation of AR116081 as Antipsychotics in Rodents, 2002 FESN, abstract.
Mestre et al., 5-Hydroxytryptamine 2A receptor antagonists as potential treatment for psychiatric disorders, (2013) Expert Opin. Investig Drugs 22(4):411-421.
Miao et al., Ketanserin Stabilizes Blood Pressure in Conscious Spontaneously Hypertensive Rats, (2003) Clin. Exp. Pharmacol. Physiol. 30(3):189-193.
Mizuki et al., Effects of Mianserin on Negative Symptoms in Schizophrenia, (1990) Int. Clinical Psychopharmacology 5:83-95.
Morairty et al., Selective 5HT2A and 5HT6 Receptor Antagonists Promote Sleep in Rats, (2008) Sleep 31(1).
Morissette et al., High-throughput crystallization: polymorphs, salts, co-crystals and solvates of pharmaceutical solids, (2004) Advanced Drug Delivery Review 56:275-300.
Mueller, Drug Immunosuppression Therapy for Adult Heart Transplantation. Part 1: Immune Response to Allograft and Mechanism of Action of Immunosuppressents, (2004) Ann. Thorac. Surg. 77:354-362.
Muto et al., Protective effects of sarpogrelate, a 5HT2A antagonist, against postischemic myocardial dysfunction in guinea-pig hearts, (2005) Molecular and Cellular Biochemistry 272:119-32.
National Institutes of Health, National Heart, Lung and Blood Institute, Facts about Insomnia, (Oct. 1995) NIH ublication No. 95-3801:1-4.
Newton et al., Mianserin-Induced Down-Regulation of Human 5-Hydroxytryptamine2A and 5-Hydroxytryptamine2c Receptors Stably Expressed in the Human Neuroblastoma Cell Line SH-SY5Y, (1997) Journal of Neurochemistry 69:1031-1038.
Nichols et al., 2,3-Dihydrobenzofuran Analogs of Hallucinogenic Phenethylamines, (Jan. 1, 1991) J. Med. Chem. 34(1):276-281.
Nishiyama, Effects of 5HT2A receptor antagonist, sarpogrelate on thermal or inflammatory pain, (2005) European Journal of Pharmacology 516:18-22.
Nomura et al., 5-HT2A receptor antagonist increases circulating adiponectin in patients with type 2 diabetes, (2005) Blood Coagulation and Fibrinolysis 16(6):423-428.
Office Action for U.S. Appl. No. 11/883,043, dated Sep. 8, 2009.
Oken, Antihistamines, a Possible Risk Factor for Alzheimer's Disease, (1995) Medical Hypotheses 44:47-48 (abstract).
Olichney et al., Cognitive Decline is Faster in Lewy Body Variant than in Alzheimer's Disease, (1998) Neurology 51:351-357 (abstract).
Ono Pharmaceutical Co., Ltd., Launch of Rivistach.RTM. Patch, for the Treatment of Dementia of Alzheimer's Type, (2011) 2 pages.
Otwinowski et al., Processing of x-ray diffraction data collected in oscillation mode, (1997) Methods Enzymology 276:307-326 (abstract).
Pawlak et al., A Potent 5-Hydroxytryptamine Receptor (5-HT2A) Antagonist, DV-7028, Delays Arterial Thrombosis Development in Rats, (1998) Thrombosis Research 90:259-270.
Pietraszek et al., Blood serotonergic mechanisms in type 2 (non-insulin-dependent) diabetes mellitus, Thromb Res., Jun. 15, 1992;66(6):765-74.
Portegies et al., Guidelines for the Diagnosis and Management of Neurological Complications of HIV Infection, (2004) Eur. J. Neurol. 11:297-304.

(56) References Cited

OTHER PUBLICATIONS

Product Information Sheet, Detrol.RTM. LA (tolterodine tartrate) capsules, Rev. Mar. 2008.
Product Information Sheet, Enablex.RTM. (darifenacin) tablets, T2010-XX.
Product Information Sheet, Exelon.RTM. Patch (rivastigmine transdermal system), LTS Lohmann Therapie Systems AG, 2000.
Product Information Sheet, Robinul RTM. glycopyrrolate tablets, Rev. Apr. 2010.
Product Information Sheet, Sanctura.RTM. (trospium chloride), Rev. Jan. 2011.
Product Information Sheet, VESIcare.RTM. (solifenacin succinate) tablets, Rev. Apr. 2010.
Prosser et al., Selective serotonin 5-HT2A, inverse agonists promote sleep consolidation in male Wistar rats during the normal inactive phase, #29, Arena Pharmaceuticals, Inc., APSS Meeting Jun. 2004 1 page.
Przyklenk et al., Targeted inhibition of the serotonin 5HT2A receptor improves coronary patency in an in vivo model of recurrent thrombosis, (2010) J. Thromb Haemost. 8(2):331-340.
QuaSAR—Quantitative Structure Activity Relationships of Analgesics, Narcotic Antagonists, and Hallucinogens, Research Monograph 22, 1978, NIDA, Barnett and Willette (eds.), 1-487.
Querbes et al., A JC Virus-Induced Signal is Required for Infection of Glial Cells by a Clathrin- and eps15-Dependent Pathway, (2004) J. Virology 78:250-256.
Ray et al., Central Anticholinergic Hypersensitivity in Aging, (Apr.-Jun. 1992) Journal of Geriatric Psychiatry and Neurology 5:72-77 (abstract).
Remington, The Science and Practice of Pharmacy, 20th Edition, 2000 (Lippincott Williams & Wilkins) TOC.
Roche, Bioreversible Carriers in Drug Design ed (1987) (TOC only).
Roe et al., Use of Anticholinergic Medications by Older Adults with Dementia, (2002) JAGS 50:836-842 (abstract).
Rosenberg et al APD125, a selective serotonin 5-HT2A receptor inverse agonist, significantly improves the key PSG parameters of sleep maintenance in patients with primary insomnia, (2008) Sleep, poster.
Rosenberg et al., APD125, a selective serotonin 5-HT2A receptor inverse agonist, significantly improves the key parameters of sleep maintenance in patients with primary insomnia, (2007) AASM (abstract).
Rosenberg et al., APD125, a selective serotonin 5-HT2A receptor inverse agonist, significantly improves sleep maintenance in primary insomnia, (2008) APA pp. 1-37.
Roth et al., APD125, a selective serotonin 5-HT2A receptor inverse agonist, significantly improves the key parameters of sleep maintenance in patients with primary insomnia, (2008) APSS pp. 1-19.
Rudolph et al., The Anticholinergic Risk Scale and Anticholinergic Adverse Effects in Older Persons, (Mar. 10, 2008) Arch Intern Med 168(5):508-513.
Sahgal, Practical behavioural neuroscience: problems, pitfalls and suggestions, (1993) Behavioral Neuroscience: A Practical Approach, IRL Press, New York, 1:1-8.
Satomura et al., Sarpogrelate, a specific 5HT2-receptor antagonist, improves the coronary microcirculation in coronary artery disease, (Jan. 2002) Clin Cardiol. 25(1):28-32.
Sawnyok et al., Antidepressants as analgesics: an overview of central and peripheral mechanisms of action, (2001) Journal of Psychiatry and Neurosciences 26(1):21-29.
Schmidt et al., The Role of 5-HT.sub.2A Receptors in Antipsychotic Activity, (1995) Life Sciences 56(25):2209-2222.
Shan et al., Investigation of Non-Aqueous Vehicles for a Poorly Soluble Compound Intended for Softgel Dosage Form Development, 2005 APSS, abstract.
Shan et al., Physicochemical Characterization During Salt Selection Process, 2005 AAPS, poster.
Shan et al., Physicochemical Characterization During Salt Selection Process, 2006 AAPS, poster.
Sharpley et al., Slow wave sleep in humans: role of 5HT2A and 5-HT2C receptors, (Mar.-Apr. 1994) Neuropharmacology.33(3-4):467-471.
Silva et al., Chronic treatment with mianserin prevents DOCA-salt hypertension in rats—evidence for the involvement of central 5-HT2 receptors, (2005) J. Pharmacol. 518(2-3)152-157, 2005.
Singh et al., Immunosuppresive-aassociated Leukoencephalopathy in Organ Transplant Recipients, (2000) Transplantation 69:467-472.
Sink et al., Dual Use of Bladder Anticholinergics and Cholinesterase Inhibitors: Long-Term Functional and Cognitive Outcomes, (2008) JAGS 56:847-853.
Smith et al., Test-retest variability of serotonin 5-HT2A receptor binding measured with positron emission tomography and [18F]altanserin in the human brain, (1998) Synapse, Dec. 30(4):380-392.
Sorenson et al., Characterization of the 5-HT2 Receptor Antagonist MDL 100907 as Putative Atypical Antipsychotic: Behavioral, Electrophysiological and Neurochemical Studies, (1993) J. Pharacol. Exp. Ther. 266(2):684-691.
Speer et al., Intrinsic Dissolution Characterization of Different Morphic Forms of a Poorly Water Soluble Compound, 2006, AAPS, abstract.
Speer et al., Influence of Digestive Enzymes Combined with Sodium Lauryl Sulfate on Dissolution of Cross-linked Gelatin Capsules, 2005 AAPS, poster.
Speer et al., Influence of Digestive Enzymes on Dissolution of a Poorly Water Soluble Compound From Cross-Linked Gelatin Capsules in Sodium Lauryl Sulfate Medium, 2005 AAPS, abstract.
Staley et al., Comparison of [(18)F]altanserin and [(18)F]deuteroaltanserin for PET imaging of serotonin(2A) receptors in baboon brain: pharmacological studies, (Apr. 2001) Nucl Med Biol. 28(3):271-279.
Storey et al., Automation of Solid Form Screening Procedures in the Pharmaceutical Industry—How to Avoid the Bottlenecks, (2004) Crystallography Reviews 10(1):45-56.
Strah-Pleynet et al., 5HT2A Receptor Inverse Agonists: Design and SAR of Novel Pyrazole Derivatives, (2006) meeting abstract.
Strah-Pleynet et al., 5-HT2A Receptor Inverse-Agonists: Design and Structure-Activity Relationship of Novel Pyrazole Derivatives, 2005 ACS, 231st ACS National Meeting, Medi 145, poster.
Strah-Pleynet et al., Bioisosteric Modifications of Urea Derivatives as 5HT2A Inverse-Agonists, 2004 ACS, meeting abstract.
Strah-Pleynet et al., Bioisosteric Modifications of Urea Derivatives as 5HT2A Inverse-Agonists, 2005 ACS, meeting poster.
Strah-Pleynet et al., Discovery and SAR of novel 5-HT.sub.2A, inverse-agonists, 227th ACS National Meeting, MED1 270, Arena Pharmaceutical Inc. (Mar. 2004), 1 page, poster.
Strah-Pleynet et al., Discovery and SAR of Novel 5-HT2A Inverse-Agonists, 2004 ACS, 227th ACS National Meeting, Medi 270, abstract.
Street et al., Olanzapine treatment of psychotic and behavioral symptoms in patients with Alzheimer disease in nursing care facilities: a double-blind, randomized, placebo-controlled trial. The HGEU Study Group. (Oct. 2000) Arch Gen Psychiatry. 57(10):968-976.
Takahashi et al., Sarpogrelate hydrochloride, a serotonin2A receptor antagonist, reduces albuminuria in diabetic patients with early-stage diabetic nephropathy, (Nov. 2002) Diabetes Res Clin Pract. 58(2):123-129.
Takenaka et al., The effect of anplag (sarpogrelate HCI), novel selective 5-HT.sub.2 antagonist on intraocular pressure in glaucoma patients, (1995) Investig Ophthalmol Iris Sci. 36(4):S724 (abstract 3390-377).
Talvik-Lotfi et al., High 51-112A receptor occupancy in M100907-treated schizophrenic patients, (2000) Phychopharmacology 148:400-403.
Tang et al., Anilinopyrazole as selective CDK2 inhibitors: design, synthesis, biological evaluation, and x-ray crystallographic analysis, (2003) Bioorg. Med. Chem. Letters 13(18):2985-2988 (abstract).
Teegarden et al., 5HT2A Inverse-Agonists for the Treatment of Insomnia, (2008) CTMC pp. 1-28.

(56) References Cited

OTHER PUBLICATIONS

Teegarden et al., Discovery of 1-[3-(4-Bromo-2-methyl-2H-pyrazol-3-yl)-4-methoxyphenyl]-3-(2,4-difluorophenyl(urea(Nelotanserin) and Related 5-Hydroxytryptamine.sub.2A Inverse Agonists for the Treatment of Insomnia, (2003) J. Med. Chem. 53:1923-1936.

Teegarden et al., Discovery of 1-[3-(4-Bromo-2-methyl-2H-pyrazol-3-yl)-4-methoxy-phenyl]-3-(2,4-difluoro- -phenyl)-urea (APD125) and Related 5-HT.sub.2A Inverse Agonists for the Treatment of Insomnia, (2009) JMC pp. 1-50.

Teramura-Gronblad et al., Use of Anticholinergic Drugs and Cholinesterase Inhibitors and Their Association with Psychological Well-Being Among Frail Older Adults in Residential Care Facilities, (2011) Ann Pharmacotherapy 45:596-602 (abstract).

Terry et al., The Cholinergic Hypothesis of Age and Alzheimer's Disease-Related Cognitive Deficits: Recent Challenges and Their Implications for Novel Drug Development, (2003) JPET 306(3):821-827.

Topliss, A Manual Method for Applying the Hansch Approach to Drug Design, (Apr. 1, 1977) J. Med. Chem. 20(4):463-469.

Vacante et al., Extension of JC Virus Host Range to Monkey Cells by Insertion of a Simian Virus 40 Enhancer into the JC Virus Regulatory Region, Virology 170:353-361.

Van Eijk et al., Effect of rivastigmine as an adjunct to usual care with haloperidol on duration of delirium and mortality in critically ill patients: a multicentre, double-blind, placebo-controlled randomised trial, (2010) The Lancet 376:1829-1837 (abstract).

Van Zwieten, Receptors Involved in the Regulation of Vascular Tone, (1985) Arzneimittelforschung. 35(12A):1904-1909.

Vanover et al., Role of 5-HT2A receptor antagonists in the treatment of insomnia, (2010) Nature and Science of Sleep 2:139-150.

Vasilevskii, Oxidative Iodination of Substituted N-Methylpyrazoles, (1980) Bull. Acad. Sci. USSR 29(5):778-784.

Vasilevsky et al., Study of the Heterocyclization of vic-Substituted Hydrazides of Actylenylpyrazolecarboxylic Acids into N-Amino Pyrazolpyridinones, (2002) J. Hetercycl. Chem. 39:1229-1233.

Verdejo et al., Tratamiento con propantelina de la incontinencia urinaria por inestabilidad vesical en pacientes ancianos, (1992) Anales de Medicina 9(3):1160120.

Verstraete, Prevention of atherosclerotic complications: controlled trial of ketanserin, (1989) British Medical Journal 298:424-430.

Vikenes et al., Serotonin is Associated with Coronary Artery Disease and Cardiac Events, (1999) Circulation 100:483-489.

Vippagunta et al., Crystalline Solids, (2001) Advanced Drug Delivery Reviews 48:3-26.

Westkaemper et al., Application of Ligand SAR, Receptor Modeling and Receptor Mutagenesis to the Discovery and Development of a New Class of 5-HT2A Ligands, (2002) Curr. Topics Med. Chem. 2:575-598 (abstract).

White, Deamination of Amines. 2-Phenylethyl Benzoate via the Nitrosoamide Decomposition, (1973) Org. Syn. Coll. 5:336-339.

Wikstrom et al., Synthesis and Pharmacological Testing of 1, 2, 3, 4, 10, 14b-Hexahydro-6-methoxy-2-methyldibenzo[cf]pyrazino[1,2-.alpha.]azepin and Its Enantiomers in Comparison with the TWO Antidepressants Mianserin and Mirtazapine, (2002) J. Med. Chem. 45:3280-3285.

Williams et al., Survival and mortality differences between dementia with Lewy bodies vs Alzheimer disease, (1935) Neurology 67:1935-1941 (abstract).

Wilson et al., LY53857, a 5HT2 receptor antagonist, delays occlusion and inhibits platelet aggregation in a rabbit model of carotid artery occlusion, (Sep. 2, 1991) Thromb Haemost. 66(3):355-360.

Winokur et al., Acute effects of mirtazapine on sleep continuity and sleep architecture in depressed patients: a pilot study, (Jul. 1, 2000) Biol Psychiatry 48(1):75-78.

Xiong et al., Discovery and SAR of Highly Selective 5-HT.sub.2A Receptor Subtype Inverse-Agonists for Inhibition of Platelet Aggregation, 2008 ACS, 235th National Meeting, Medi 45, poster.

Xiong et al., Synthesis and in Vivo Evaluation of Phenethylpiperazine Amides: Selective 5-Hydroxytryptamine2A Receptor Antagonists for the Treatment of Insomnia, (2010) Journal of Medical Chemistry 53:5696-5706.

Yamada et al., Phase I/II trial of didanosine (2',2'-dideoxyinosine) in hemophiliac patients with AIDS or AIDS-related complex, (1993) Clin. Diagn. Virol. 1:245-256.

Yamashita et al., Conjunctive effects of the 5HT2 receptor antagonist, sarpogrelate, on thrombolysis with modified tissue plasminogen activator in different laser-induced thrombosis models, (2000) Haemostatis 30:321-332 (abstract).

Yevich et al., Second generation antimigraine 5-HT1B/D agonists: structure activity relationship and preclinical pharmacological distinctions, (1997) Curr. Med. Chem. 4(5):295-312 (abstract).

Zhu et al., Synthesis and mode of action of 125I- and 3H-labeled Thieno[2,3-c]pyridine antagonists of cell adhesion molecule expression, (2000) J. Org. Chem. 67:943-948.

Goldman et al., Finding Balance: New Strategies to Optimize Care for Patients With Parkinson's Disease Psychosis, Supplement to Neurology Reviews, Aug. 1, 2016 [retrieved on Sep. 19, 2018). Retrieved from internet: <URL: http:f/mededicus.com/downloads/Optimize_Care_Patients_Parkinson_Disease_Psychosis.pdf> pp. S1-S12.

International Search Report and Written Opinion for PCT/US2018/046363 dated Oct. 15, 2018.

\* cited by examiner

PYRAZOLE DERIVATIVES AS MODULATORS OF THE 5-HT$_{2A}$ SEROTONIN RECEPTOR USEFUL FOR THE TREATMENT OF DISORDERS RELATED THERETO

CROSS-REFERENCE TO RELATED APPLICATIONS

This application is a continuation application of U.S. application Ser. No. 14/692,807 filed Apr. 22, 2015, which is a continuation application of U.S. application Ser. No. 12/444,098 filed Apr. 27, 2009, now U.S. Pat. No. 9,434,692 issued on Sep. 6, 2016, which is a national stage application of PCT/US2007/021182 filed on Oct. 2, 2007, which claims priority from U.S. Provisional Application No. 60/849,070 filed Oct. 3, 2006, each of which are hereby incorporated herein by reference in their entireties.

FIELD OF THE INVENTION

The present invention relates to certain pyrazole derivatives of Formula (Ia) and pharmaceutical compositions thereof that modulate the activity of the 5-HT$_{2A}$ serotonin receptor. Compounds and pharmaceutical compositions thereof are directed to methods useful in the treatment of insomnia and related sleep disorders, platelet aggregation, coronary artery disease, myocardial infarction, transient ischemic attack, angina, stroke, atrial fibrillation, reducing the risk of blood clot formation, asthma or symptoms thereof, agitation or symptoms thereof, behavioral disorders, drug induced psychosis, excitative psychosis, Gilles de la Tourette's syndrome, manic disorder, organic or NOS psychosis, psychotic disorders, psychosis, acute schizophrenia, chronic schizophrenia, NOS schizophrenia and related disorders, diabetic-related disorders, progressive multifocal leukoencephalopathy and the like.

The present invention also relates to the methods for the treatment of 5-HT$_{2A}$ serotonin receptor mediated disorders in combination with other pharmaceutical agents administered separately or together.

BACKGROUND OF THE INVENTION

Serotonin Receptors

Receptors for serotonin (5-hydroxytryptamine, 5-HT) are an important class of G protein coupled receptors. Serotonin is thought to play a role in processes related to learning and memory, sleep, thermoregulation, mood, motor activity, pain, sexual and aggressive behaviors, appetite, neurodegenerative regulation, and biological rhythms. Not surprisingly, serotonin is linked to pathophysiological conditions such as anxiety, depression, obsessive compulsive disorders, schizophrenia, suicide, autism, migraine, emesis, alcoholism, and neurodegenerative disorders. With respect to antipsychotic treatment approaches focused on the serotonin receptors, these types of therapeutics can generally be divided into two classes, the "typical" and the "atypical." Both have anti-psychotic effects, but the typicals also include concomitant motor-related side effects (extra pyramidal syndromes, e.g., lip-smacking, tongue darting, locomotor movement, etc.). Such side effects are thought to be associated with the compounds interacting with other receptors, such as the human dopamine D$_2$ receptor in the nigrostriatal pathway. Therefore, an atypical treatment is preferred. Haloperidol is considered a typical anti-psychotic, and clozapine is considered an atypical anti-psychotic.

Serotonin receptors are divided into seven subfamilies, referred to as 5-HT$_1$ through 5-HT$_7$, inclusive. These subfamilies are further divided into subtypes. For example, the 5-HT$_2$ subfamily is divided into three receptor subtypes: 5-HT$_{2A}$, 5-HT$_{2B}$, and 5-HT$_{2C}$. The human 5-HT$_{2C}$ receptor was first isolated and cloned in 1987, and the human 5-HT$_{2A}$ receptor was first isolated and cloned in 1990. These two receptors are thought to be the site of action of hallucinogenic drugs. Additionally, antagonists to the 5-HT$_{2A}$ and 5-HT$_{2C}$ receptors are believed to be useful in treating depression, anxiety, psychosis, and eating disorders.

SUMMARY OF THE INVENTION

One aspect of the present invention encompasses certain pyrazole derivatives as shown in Formula (Ia):

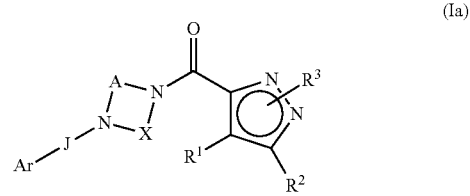

or a pharmaceutically acceptable salt, solvate or hydrate thereof;
wherein:
R$^1$ and R$^2$ are each independently selected from the group consisting of H, C$_1$-C$_6$ alkyl, C$_1$-C$_6$ alkylaryl, aryl, C$_3$-C$_7$ cycloalkyl, C$_1$-C$_6$ haloalkyl, halogen, heteroaryl, and nitro; and wherein C$_1$-C$_6$ alkyl, aryl and heteroaryl are optionally substituted with 1, 2, 3, 4 or 5 substituents selected independently from the group consisting of C$_1$-C$_6$ acyl, C$_1$-C$_6$ acyloxy, C$_2$-C$_6$ alkenyl, C$_1$-C$_6$ alkoxy, C$_1$-C$_6$ alkyl, C$_1$-C$_6$ alkylcarboxamide, C$_1$-C$_6$ alkylsulfonamide, C$_1$-C$_6$ alkylsulfinyl, C$_1$-C$_6$ alkylsulfonyl, C$_1$-C$_6$ alkylthio, C$_1$-C$_6$ alkylureyl, C$_1$-C$_6$ alkylamino, C$_2$-C$_6$ alkynyl, amino, carbo-C$_1$-C$_6$-alkoxy, carboxamide, carboxy, cyano, C$_3$-C$_7$ cycloalkyl, C$_2$-C$_6$ dialkylamino, C$_2$-C$_6$ dialkylcarboxamide, C$_2$-C$_6$ dialkylsulfonamide, C$_1$-C$_6$ haloalkoxy, C$_1$-C$_6$ haloalkyl, C$_1$-C$_6$ haloalkylsulfinyl, C$_1$-C$_6$ haloalkylsulfonyl, C$_1$-C$_6$ haloalkylthio, halogen, hydroxyl, nitro, sulfonamide and thiol; or R$^1$ and R$^2$ together with the carbon atoms to which they are bonded form a C$_3$-C$_7$ carbocyclyl or a C$_3$-C$_7$ heterocyclyl group each optionally substituted with 1, 2, 3, 4 or 5 substituents selected independently from the group consisting of C$_1$-C$_6$ acyl, C$_1$-C$_6$ acyloxy, C$_2$-C$_6$ alkenyl, C$_1$-C$_6$ alkoxy, C$_1$-C$_6$ alkyl, C$_1$-C$_6$ alkylcarboxamide, C$_1$-C$_6$ alkylsulfonamide, C$_1$-C$_6$ alkylsulfinyl, C$_1$-C$_6$ alkylsulfonyl, C$_1$-C$_6$ alkylthio, C$_1$-C$_6$ alkylureyl, C$_1$-C$_6$ alkylamino, C$_2$-C$_6$ alkynyl, amino, carbo-C$_1$-C$_6$-alkoxy, carboxamide, carboxy, cyano, C$_3$-C$_7$ cycloalkyl, C$_2$-C$_6$ dialkylamino, C$_2$-C$_6$ dialkylcarboxamide, C$_2$-C$_6$ dialkylsulfonamide, C$_1$-C$_6$ haloalkoxy, C$_1$-C$_6$ haloalkyl, C$_1$-C$_6$ haloalkylsulfinyl, C$_1$-C$_6$ haloalkylsulfonyl, C$_1$-C$_6$ haloalkylthio, halogen, hydroxyl, nitro, oxo, sulfonamide and thiol;

R$^3$ is selected from the group consisting of H, C$_1$-C$_6$ alkyl and aryl; and wherein aryl is optionally substituted with 1, 2, 3, 4 or 5 substituents selected independently from the group consisting of C$_1$-C$_6$ acyl, C$_1$-C$_6$ acyloxy, C$_2$-C$_6$ alkenyl, C$_1$-C$_6$ alkoxy, C$_1$-C$_6$ alkyl, C$_1$-C$_6$ alkylcarboxamide, C$_1$-C$_6$ alkylsulfonamide, C$_1$-C$_6$ alkylsulfinyl, C$_1$-C$_6$ alkylsulfonyl, C$_1$-C$_6$ alkylthio, C$_1$-C$_6$ alkylureyl, C$_1$-C$_6$ alkylamino, $C_2$-$C_6$ alkynyl, amino, carbo-$C_1$-$C_6$-alkoxy, carboxamide, carboxy, cyano, $C_3$-$C_7$ cycloalkyl, $C_2$-$C_6$ dialkylamino, $C_2$-$C_6$ dialkylcarboxamide, $C_2$-$C_6$ dialkylsulfonamide, $C_1$-$C_6$ haloalkoxy, $C_1$-$C_6$ haloalkyl, $C_1$-$C_6$ haloalkylsulfinyl, $C_1$-$C_6$ haloalkylsulfonyl, $C_1$-$C_6$ haloalkylthio, halogen, hydroxyl, nitro, sulfonamide and thiol;

A and X are each —$CH_2CH_2$—, each optionally substituted with 1, 2, 3 or 4 substituents selected independently from the group consisting of $C_1$-$C_4$ alkoxy, $C_1$-$C_3$ alkyl, carboxy, cyano, $C_1$-$C_3$ haloalkyl, halogen, hydroxyl and oxo;

J is —$CH_2CH_2$— or —$C(=NOMe)CH_2$— each optionally substituted with 1, 2, 3 or 4 substituents selected independently from the group consisting of $C_1$-$C_4$ alkoxy, $C_1$-$C_3$ alkyl, carboxy, cyano, $C_1$-$C_3$ haloalkyl, halogen, hydroxyl and oxo; and Ar is aryl or heteroaryl each optionally substituted with 1, 2, 3, 4 or 5 substituents selected independently from the group consisting of $C_1$-$C_6$ acyl, $C_1$-$C_6$ acyloxy, $C_2$-$C_6$ alkenyl, $C_1$-$C_6$ alkoxy, $C_1$-$C_6$ alkyl, $C_1$-$C_6$ alkylcarboxamide, $C_1$-$C_6$ alkylsulfonamide, $C_1$-$C_6$ alkylsulfinyl, $C_1$-$C_6$ alkylsulfonyl, $C_1$-$C_6$ alkylthio, $C_1$-$C_6$ alkylureyl, $C_1$-$C_6$ alkylamino, $C_2$-$C_6$ alkynyl, amino, carbo-$C_1$-$C_6$-alkoxy, carboxamide, carboxy, cyano, $C_3$-$C_7$ cycloalkyl, $C_2$-$C_6$ dialkylamino, $C_2$-$C_6$ dialkylcarboxamide, $C_2$-$C_6$ dialkylsulfonamide, $C_1$-$C_6$ haloalkoxy, $C_1$-$C_6$ haloalkyl, $C_1$-$C_6$ haloalkylsulfinyl, $C_1$-$C_6$ haloalkylsulfonyl, $C_1$-$C_6$ haloalkylthio, halogen, $C_3$-$C_7$ heterocyclyl, hydroxyl, nitro, sulfonamide and thiol.

One aspect of the present invention pertains to pharmaceutical compositions comprising a compound of the present invention and a pharmaceutically acceptable carrier.

One aspect of the present invention pertains to methods for treating 5-$HT_{2A}$ mediated disorders in an individual comprising administering to said individual in need thereof a therapeutically effective amount of a compound of the present invention or a pharmaceutical composition thereof.

One aspect of the present invention pertains to methods for treating 5-$HT_{2A}$ mediated disorders selected from the group consisting of coronary artery disease, myocardial infarction, transient ischemic attack, angina, stroke, and atrial fibrillation in an individual comprising administering to said individual in need thereof a therapeutically effective amount of a compound of the present invention or a pharmaceutical composition thereof.

One aspect of the present invention pertains to methods for treating sleep disorders in an individual comprising administering to said individual in need thereof a therapeutically effective amount of a compound of the present invention or a pharmaceutical composition thereof.

One aspect of the present invention pertains to methods for treating dyssomnias.

One aspect of the present invention pertains to methods for treating insomnia.

One aspect of the present invention pertains to methods for treating parasomnias.

One aspect of the present invention pertains to methods for increasing slow wave sleep.

One aspect of the present invention pertains to methods for improving sleep consolidation.

One aspect of the present invention pertains to methods for improving sleep maintenance.

One aspect of the present invention pertains to methods for treating conditions associated with platelet aggregation in an individual comprising administering to said individual in need thereof a therapeutically effective amount of a compound of the present invention or a pharmaceutical composition thereof.

One aspect of the present invention pertains to methods for reducing the risk of blood clot formation in an angioplasty or coronary bypass surgery individual comprising administering to said individual in need thereof a therapeutically effective amount of a compound of the present invention or a pharmaceutical composition thereof.

One aspect of the present invention pertains to methods for reducing the risk of blood clot formation in an individual suffering from atrial fibrillation, comprising administering to said individual in need thereof a therapeutically effective amount of a compound of the present invention or a pharmaceutical composition thereof.

One aspect of the present invention pertains to methods for treating diabetic-related disorders in an individual comprising administering to said individual in need thereof a therapeutically effective amount of a compound of the present invention or a pharmaceutical composition thereof.

One aspect of the present invention pertains to methods for treating progressive multifocal leukoencephalopathy in an individual comprising administering to said individual in need thereof a therapeutically effective amount of a compound of the present invention or a pharmaceutical composition thereof.

One aspect of the present invention pertains to methods for treating hypertension in an individual comprising administering to the individual in need thereof a therapeutically effective amount of a compound of the present invention or a pharmaceutical composition thereof.

One aspect of the present invention pertains to methods for treating pain in an individual comprising administering to the individual in need thereof a therapeutically effective amount of a compound of the present invention or a pharmaceutical composition thereof.

One aspect of the present invention pertains to use of compounds of the present invention for the manufacture of a medicament for the treatment of a sleep disorder.

One aspect of the present invention pertains to use of compounds of the present invention for the manufacture of a medicament for the treatment of a dyssomnia.

One aspect of the present invention pertains to use of compounds of the present invention for the manufacture of a medicament for the treatment of insomnia.

One aspect of the present invention pertains to use of compounds of the present invention for the manufacture of a medicament for the treatment of a parasomnia.

One aspect of the present invention pertains to use of compounds of the present invention for the manufacture of a medicament for increasing slow wave sleep.

One aspect of the present invention pertains to use of compounds of the present invention for the manufacture of a medicament for improving sleep consolidation.

One aspect of the present invention pertains to use of compounds of the present invention for the manufacture of a medicament for improving sleep maintenance.

One aspect of the present invention pertains to use of compounds of the present invention for the manufacture of a medicament for the treatment of a 5-$HT_{2A}$ mediated disorder.

One aspect of the present invention pertains to use of compounds of the present invention for the manufacture of a medicament for the treatment of a 5-$HT_{2A}$ mediated disorder selected from the group consisting of coronary artery disease, myocardial infarction, transient ischemic attack, angina, stroke, and atrial fibrillation.

One aspect of the present invention pertains to use of compounds of the present invention for the manufacture of a medicament for the treatment of a condition associated with platelet aggregation.

One aspect of the present invention pertains to use of compounds of the present invention for the manufacture of a medicament for the reduction of the risk of blood clot formation in an angioplasty or coronary bypass surgery individual.

One aspect of the present invention pertains to use of compounds of the present invention for the manufacture of a medicament for the reduction of the risk of blood clot formation in an individual.

One aspect of the present invention pertains to use of compounds of the present invention for the manufacture of a medicament for the reduction of the risk of blood clot formation in an individual suffering from atrial fibrillation.

One aspect of the present invention pertains to use of compounds of the present invention for the manufacture of a medicament for the treatment of a diabetic-related disorder.

One aspect of the present invention pertains to use of compounds of the present invention for the manufacture of a medicament for the treatment of progressive multifocal leukoencephalopathy.

One aspect of the present invention pertains to use of compounds of the present invention for the manufacture of a medicament for the treatment of hypertension.

One aspect of the present invention pertains to use of compounds of the present invention for the manufacture of a medicament for the treatment of pain.

One aspect of the present invention pertains to use of compounds of the present invention for use in a method of treatment of the human or animal body by therapy.

One aspect of the present invention pertains to use of compounds of the present invention for use in a method for the treatment of a 5-HT$_{2A}$ mediated disorder in the human or animal body by therapy.

One aspect of the present invention pertains to use of compounds of the present invention for use in a method for the treatment of a 5-HT$_{2A}$ mediated disorder selected from the group consisting of coronary artery disease, myocardial infarction, transient ischemic attack, angina, stroke, and atrial fibrillation.

One aspect of the present invention pertains to use of compounds of the present invention for use in a method for the treatment of a sleep disorder in the human or animal body by therapy.

One aspect of the present invention pertains to use of compounds of the present invention for use in a method for the treatment of a dyssomnia.

One aspect of the present invention pertains to use of compounds of the present invention for use in a method for the treatment of insomnia.

One aspect of the present invention pertains to use of compounds of the present invention for use in a method for the treatment of a parasomnia.

One aspect of the present invention pertains to use of compounds of the present invention for use in a method for increasing slow wave sleep.

One aspect of the present invention pertains to use of compounds of the present invention for use in a method for improving sleep consolidation.

One aspect of the present invention pertains to use of compounds of the present invention for use in a method for improving sleep maintenance.

One aspect of the present invention pertains to use of compounds of the present invention for use in a method for the treatment of a condition associated with platelet aggregation.

One aspect of the present invention pertains to use of compounds of the present invention for use in a method of reducing the risk of blood clot formation in an angioplasty or coronary bypass surgery individual.

One aspect of the present invention pertains to use of compounds of the present invention for use in a method of reducing the risk of blood clot formation in an individual.

One aspect of the present invention pertains to use of compounds of the present invention for use in a method of reducing the risk of blood clot formation in an individual suffering from atrial fibrillation.

One aspect of the present invention pertains to use of compounds of the present invention for use in a method for the treatment of a diabetic-related disorder in the human or animal body by therapy.

One aspect of the present invention pertains to use of compounds of the present invention for use in a method for the treatment of progressive multifocal leukoencephalopathy in the human or animal body by therapy.

One aspect of the present invention pertains to use of compounds of the present invention for use in a method for the treatment of hypertension.

One aspect of the present invention pertains to use of compounds of the present invention for use in a method for the treatment of pain.

One aspect of the present invention pertains to processes for preparing a composition comprising admixing a compound of the present invention and a pharmaceutically acceptable carrier.

These and other aspects of the invention disclosed herein will be set forth in greater detail as the patent disclosure proceeds.

DETAILED DESCRIPTION OF THE INVENTION

Definitions

Figure 1:
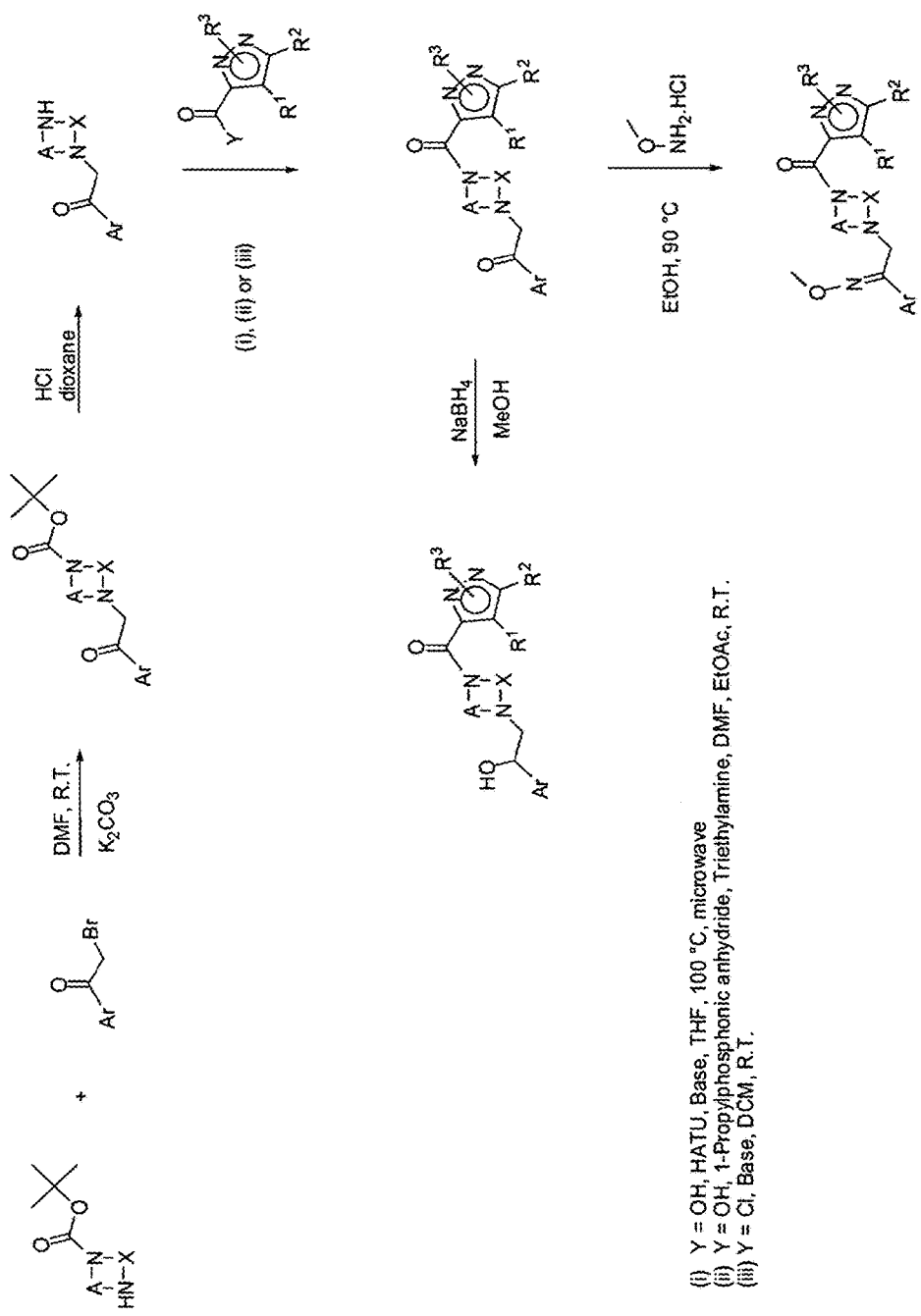
FIG. 1 shows a general synthetic scheme for preparation of compounds of Formula (Ia). A mono Boc-protected piperazine derivative is reacted with an α-bromo ketone, the Boc-group is removed and the piperazine is subsequently acylated with a pyrazole derivative. The ketone can then undergo further transformation to the alcohol or the oxime.
Figure 2:
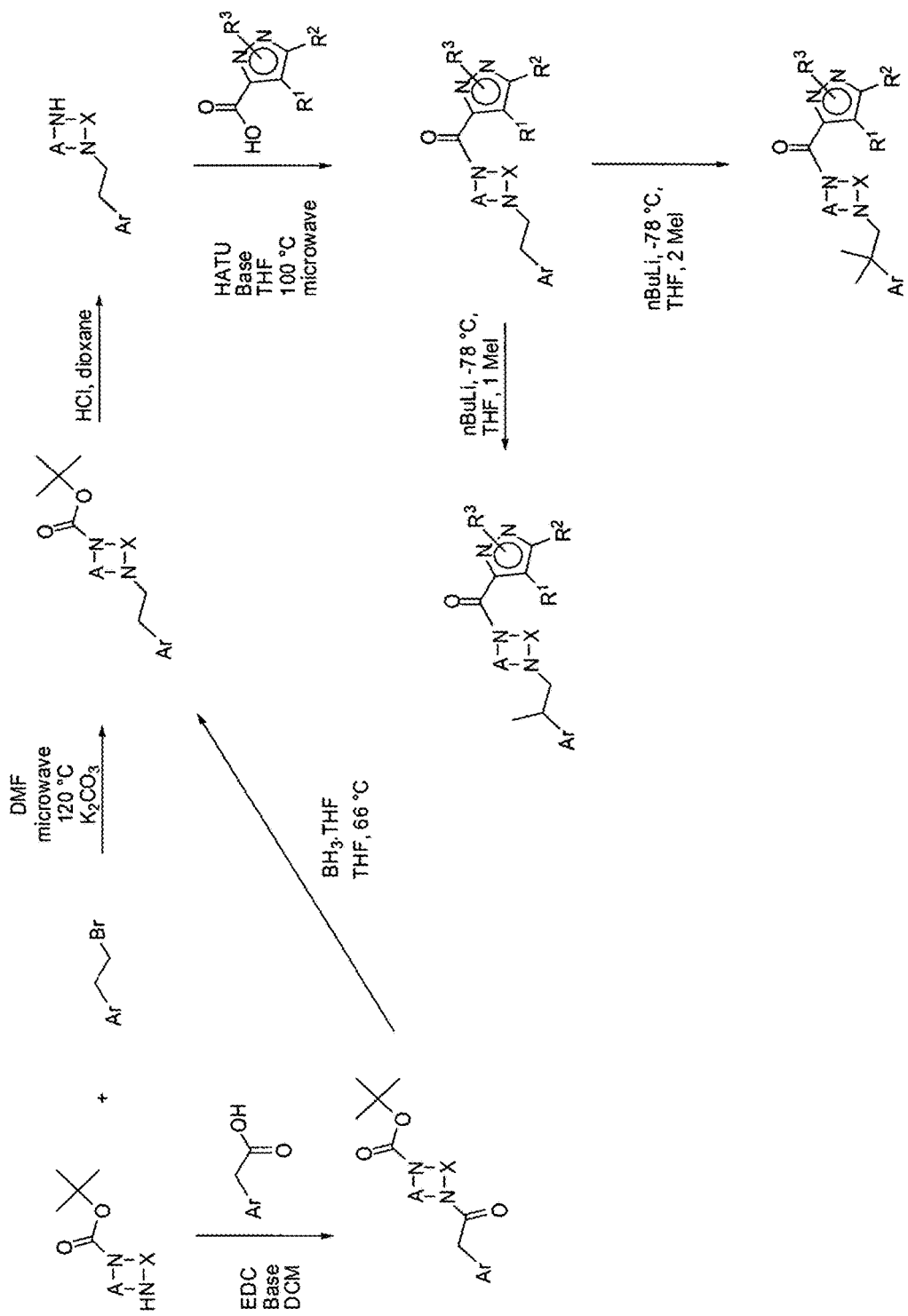
FIG. 2 shows a second general synthetic scheme for preparation of compounds of Formula (Ia). The mono Boc-protected piperazine derivative can be alkylated with an alkyl bromide or reacted with a carboxylic acid and subsequently reduced to give the N-alkylpiperazine. On removal of the Boc-protecting group, compounds of Formula (Ia) are prepared by acylation of the piperazine nitrogen with a pyrazole carboxylic acid derivative in the presence of HATU. These compounds may be alkylated by treatment with n-butyllithium and methyl iodide.
Figure 3:
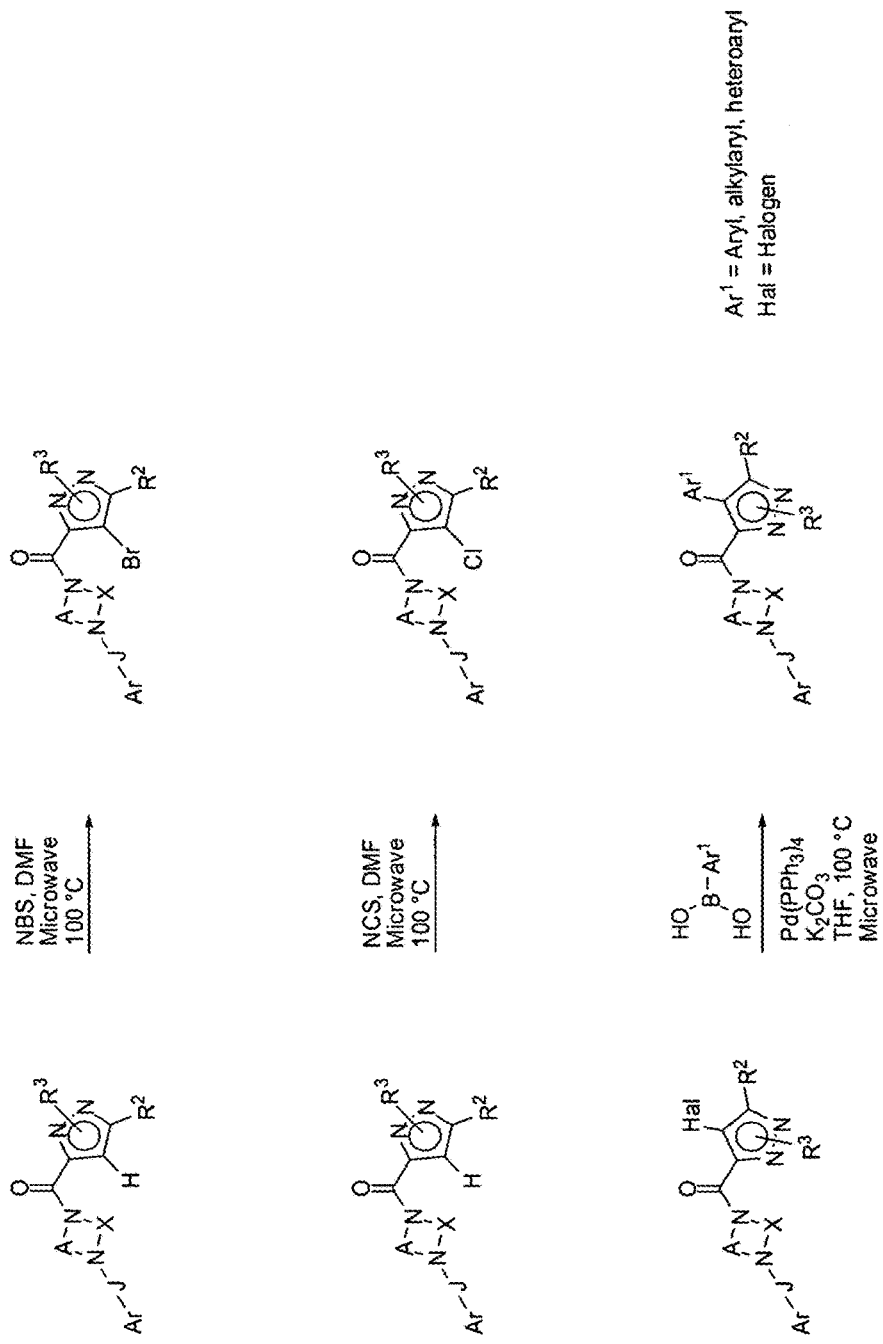
FIG. 3 shows bromination or chlorination of certain pyrazole derivatives of Formula (Ia) by treatment with N-bromosuccinimide or N-chlorosuccinimide respectively. Also shown is a Suzuki coupling between a 4-halopyrazole and an aromatic boronic acid.
Figure 4:
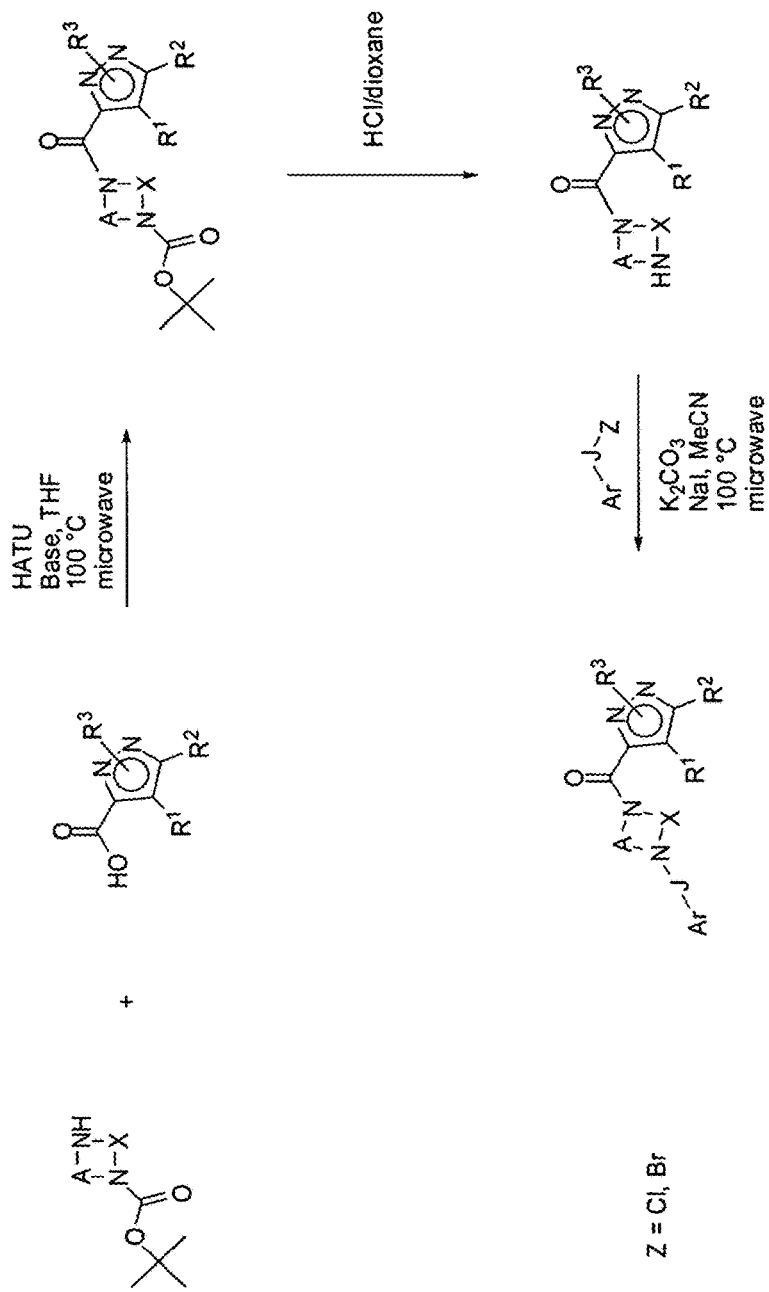
FIG. 4 shows a third general synthetic scheme for preparation of compounds of Formula (Ia). Here, the mono Boc-protected piperazine derivative is first acylated with a pyrazole carboxylic acid derivative in the presence of HATU. Acid catalyzed deprotection of the N-Boc group is followed by alkylation of the second piperazine nitrogen with an alkyl halide.

For clarity and consistency, the following definitions will be used throughout this patent document.

The term "agonists" is intended to mean moieties that interact and activate the receptor, such as the 5-HT$_{2A}$ serotonin receptor, and initiate a physiological or pharmacological response characteristic of that receptor. For example, when moieties activate the intracellular response upon binding to the receptor, or enhance GTP binding to membranes.

The term "antagonists" is intended to mean moieties that competitively bind to the receptor at the same site as agonists (for example, the endogenous ligand), but which do not activate the intracellular response initiated by the active form of the receptor, and can thereby inhibit the intracellular responses by agonists or partial agonists. Antagonists do not diminish the baseline intracellular response in the absence of an agonist or partial agonist.

The term "contact or contacting" is intended to mean bringing the indicated moieties together, whether in an in vitro system or an in vivo system. Thus, "contacting" a 5-HT$_{2A}$ serotonin receptor with a compound of the invention includes the administration of a compound of the present invention to an individual, preferably a human, having a 5-HT$_{2A}$ serotonin receptor, as well as, for example, introducing a compound of the invention into a sample containing a cellular or more purified preparation containing a 5-HT$_{2A}$ serotonin receptor.

The term "in need of treatment" and the term "in need thereof" when referring to treatment are used interchangeably to mean a judgment made by a caregiver (e.g. physician, nurse, nurse practitioner, etc. in the case of humans; veterinarian in the case of animals, including non-human mammals) that an individual or animal requires or will benefit from treatment. This judgment is made based on a variety of factors that are in the realm of a caregiver's expertise, but that includes the knowledge that the individual or animal is ill, or will become ill, as the result of a disease, condition or disorder that is treatable by the compounds of the invention. Accordingly, the compounds of the invention can be used in a protective or preventive manner; or compounds of the invention can be used to alleviate, inhibit or ameliorate the disease, condition or disorder.

The term "individual" is intended to mean any animal, including mammals, preferably mice, rats, other rodents, rabbits, dogs, cats, swine, cattle, sheep, horses, or primates, and most preferably humans.

The term "inverse agonists" is intended to mean moieties that bind to the endogenous form of the receptor or to the constitutively activated form of the receptor, and which inhibit the baseline intracellular response initiated by the active form of the receptor below the normal base level of activity which is observed in the absence of agonists or partial agonists, or decrease GTP binding to membranes. Preferably, the baseline intracellular response is inhibited in the presence of the inverse agonist by at least 30%, more preferably by at least 50%, and most preferably by at least 75%, as compared with the baseline response in the absence of the inverse agonist.

The term "modulate or modulating" is intended to mean an increase or decrease in the amount, quality, response or effect of a particular activity, function or molecule.

The term "pharmaceutical composition" is intended to mean a composition comprising at least one active ingredient; including but not limited to, salts, solvates and hydrates of compounds of the present invention; whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

The term "therapeutically effective amount" is intended to mean the amount of active compound or pharmaceutical agent that elicits the biological or medicinal response in a tissue, system, animal, individual or human that is being sought by a researcher, veterinarian, medical doctor or other clinician or caregiver; or by an individual, which includes one or more of the following:

(1) Preventing the disease; for example, preventing a disease, condition or disorder in an individual that may be predisposed to the disease, condition or disorder but does not yet experience or display the pathology or symptomatology of the disease, (2) Inhibiting the disease; for example, inhibiting a disease, condition or disorder in an individual that is experiencing or displaying the pathology or symptomatology of the disease, condition or disorder (i.e., arresting further development of the pathology and/or symptomatology), and (3) Ameliorating the disease; for example, ameliorating a disease, condition or disorder in an individual that is experiencing or displaying the pathology or symptomatology of the disease, condition or disorder (i.e., reversing the pathology and/or symptomatology).

Chemical Group, Moiety or Radical

The term "$C_1$-$C_6$ acyl" is intended to mean a $C_1$-$C_6$ alkyl radical attached to the carbon of a carbonyl group wherein the definition of alkyl has the same definition as described herein; some examples include, but are not limited to, acetyl, propionyl, n-butanoyl, iso-butanoyl, sec-butanoyl, t-butanoyl (i.e., pivaloyl), pentanoyl, and the like.

The term "$C_1$-$C_6$ acyloxy" is intended to mean an acyl radical attached to an oxygen atom wherein acyl has the same definition as described herein; some embodiments are when acyloxy is $C_1$-$C_5$ acyloxy, some embodiments are when acyloxy is $C_1$-$C_4$ acyloxy. Some examples include, but are not limited to, acetyloxy, propionyloxy, butanoyloxy, iso-butanoyloxy, sec-butanoyloxy, t-butanoyloxy, pentanoyloxy, hexanoyloxy, and the like.

The term "$C_2$-$C_6$ alkenyl" is intended to mean a radical containing 2 to 6 carbons wherein at least one carbon-carbon double bond is present, some embodiments are 2 to 5 carbons, some embodiments are 2 to 4 carbons, some embodiments are 2 to 3 carbons, and some embodiments have 2 carbons. Both E and Z isomers are embraced by the term "alkenyl." Furthermore, the term "alkenyl" includes di- and tri-alkenyls. Accordingly, if more than one double bond is present then the bonds may be all E or all Z or a mixture thereof. Examples of an alkenyl include vinyl, allyl, 2-butenyl, 3-butenyl, 2-pentenyl, 3-pentenyl, 4-pentenyl, 2-hexenyl, 3-hexenyl, 4-hexenyl, 5-hexenyl, 2,4-hexadienyl and the like.

The term "$C_1$-$C_6$ alkoxy" is intended to mean a $C_1$-$C_6$ alkyl radical, as defined herein, attached directly to an oxygen atom, some embodiments are 1 to 5 carbons, some embodiments are 1 to 4 carbons, some embodiments are 1 to 3 carbons, and some embodiments are 1 or 2 carbons. Examples include methoxy, ethoxy, n-propoxy, iso-propoxy, n-butoxy, t-butoxy, iso-butoxy, sec-butoxy and the like.

The term "$C_1$-$C_6$ alkyl" is intended to mean a straight or branched carbon radical containing 1 to 6 carbons, some embodiments are 1 to 5 carbons, some embodiments are 1 to 4 carbons, some embodiments are 1 to 3 carbons, and some embodiments are 1 or 2 carbons. Examples of an alkyl include, but not limited to, methyl, ethyl, n-propyl, iso-propyl, n-butyl, sec-butyl, iso-butyl, t-butyl, pentyl, iso-pentyl, t-pentyl, neo-pentyl, 1-methylbutyl [i.e., —CH(CH$_3$)CH$_2$CH$_2$CH$_3$], 2-methylbutyl [i.e., —CH$_2$CH(CH$_3$)CH$_2$CH$_3$], n-hexyl and the like.

The term "$C_1$-$C_6$ alkylaryl" is intended to mean a $C_1$-$C_6$ alkyl radical attached to an aromatic ring radical containing 6 to 10 ring carbons wherein the alkyl radical and the aryl radical have the same definitions as described herein. Examples include, but are not limited to tolyl and xylyl.

The term "$C_1$-$C_6$ alkylcarboxamido" or "$C_1$-$C_6$ alkylcarboxamide" is intended to mean a single $C_1$-$C_6$ alkyl group attached to either the carbon or the nitrogen of an amide group, wherein alkyl has the same definition as found herein. The $C_1$-$C_6$ alkylcarboxamido may be represented the following

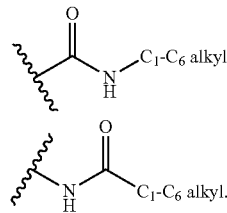

Examples include, but are not limited to, N-methylcarboxamide, N-ethylcarboxamide, N-n-propylcarboxamide, N-iso-propylcarboxamide, N-n-butylcarboxamide, N-sec-butylcarboxamide, N-iso-butylcarboxamide, N-t-butylcarboxamide and the like.

The term "$C_1$-$C_6$ alkylsulfinyl" is intended to mean a $C_1$-$C_6$ alkyl radical attached to the sulfur of a sulfoxide radical having the formula: —S(O)— wherein the alkyl radical has the same definition as described herein. Examples include, but are not limited to, methylsulfinyl, ethylsulfinyl, n-propylsulfinyl, iso-propylsulfinyl, n-butylsulfinyl, sec-butylsulfinyl, iso-butylsulfinyl, t-butylsulfinyl, and the like.

The term "$C_1$-$C_6$ alkylsulfonamide" is intended to mean the groups shown below:

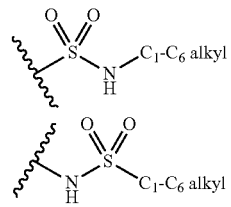

wherein $C_1$-$C_6$ alkyl has the same definition as described herein.

The term "$C_1$-$C_6$ alkylsulfonyl" is intended to mean a $C_1$-$C_6$ alkyl radical attached to the sulfur of a sulfone radical having the formula: —S(O)$_2$— wherein the alkyl radical has the same definition as described herein. Examples include, but are not limited to, methylsulfonyl, ethylsulfonyl, n-propylsulfonyl, iso-propylsulfonyl, n-butylsulfonyl, sec-butylsulfonyl, iso-butylsulfonyl, t-butylsulfonyl, and the like.

The term "$C_1$-$C_6$ alkylthio" is intended to mean a $C_1$-$C_6$ alkyl radical attached to a sulfur atom (i.e., —S—) wherein the alkyl radical has the same definition as described herein. Examples include, but are not limited to, methylsulfanyl (i.e., CH$_3$S—), ethylsulfanyl, n-propylsulfanyl, iso-propylsulfanyl, n-butylsulfanyl, sec-butylsulfanyl, iso-butylsulfanyl, t-butylsulfanyl, and the like.

The term "$C_1$-$C_6$ alkylureyl" is intended to mean the group of the formula: —NC(O)N— wherein one are both of the nitrogens are substituted with the same or different $C_1$-$C_6$ alkyl group wherein alkyl has the same definition as described herein. Examples of an alkylureyl include, but are not limited to, CH$_3$NHC(O)NH—, NH$_2$C(O)NCH$_3$—, (CH$_3$)$_2$NC(O)NH—, (CH$_3$)$_2$NC(O)NCH$_3$—, CH$_3$CH$_2$NHC(O)NH—, CH$_3$CH$_2$NHC(O)NCH$_3$—, and the like.

The term "$C_2$-$C_6$ alkynyl" is intended to mean a radical containing 2 to 6 carbons and at least one carbon-carbon triple bond, some embodiments have 2 to 4 carbons, some embodiments have 2 to 3 carbons, and some embodiments have 2 carbons. Examples of an alkynyl include, but are not limited to, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and the like. The term "alkynyl" includes di- and tri-ynes.

The term "amino" is intended to mean the group —NH$_2$.

The term "$C_1$-$C_6$ alkylamino" is intended to mean one alkyl radical attached to a —NH— radical wherein the alkyl radical has the same meaning as described herein. Some examples include, but are not limited to, methylamino, ethylamino, n-propylamino, iso-propylamino, n-butylamino, sec-butylamino, iso-butylamino, t-butylamino, and the like. Some embodiments are "$C_1$-$C_2$ alkylamino."

The term "aryl" is intended to mean an aromatic ring radical containing 6 to 10 ring carbons. Examples include phenyl and naphthyl.

The term "carbo-$C_1$-$C_6$-alkoxy" is intended to mean a $C_1$-$C_6$ alkyl ester of a carboxylic acid, wherein the alkyl group is as defined herein. Examples include, but are not limited to, carbomethoxy [—C(=O)OCH$_3$], carboethoxy, carbopropoxy, carboisopropoxy, carbobutoxy, carbo-sec-butoxy, carbo-iso-butoxy, carbo-t-butoxy, carbo-n-pentoxy, carbo-iso-pentoxy, carbo-t-pentoxy, carbo-neo-pentoxy, carbo-n-hexyloxy, and the like.

The term "$C_3$-$C_7$ carbocyclyl" or "$C_3$-$C_7$ carbocyclic" is intended to mean a non-aromatic carbon ring (i.e., $C_3$-$C_7$ cycloalkyl or $C_4$-$C_7$ cycloalkenyl as defined herein).

The term "carboxamide" is intended to mean the group —CONH$_2$.

The term "carboxy" or "carboxyl" is intended to mean the group —CO$_2$H; also referred to as a carboxylic acid group.

The term "cyano" is intended to mean the group —CN.

The term "$C_4$-$C_7$ cycloalkenyl" is intended to mean a non-aromatic ring radical containing 4 to 7 ring carbons and at least one double bond; some embodiments contain 4 carbons; some embodiments contain 5 carbons; some embodiments contain 6 carbons; some embodiments contain 7 carbons. Examples include cyclobutenyl, cyclopentenyl, cyclohexenyl, cycloheptenyl and the like.

The term "$C_3$-$C_7$ cycloalkyl" is intended to mean a saturated ring radical containing 3 to 7 carbons; some embodiments contain 3 to 6 carbons; some embodiments contain 3 to 5 carbons; some embodiments contain 5 to 7 carbons; some embodiments contain 3 to 4 carbons. Examples include cyclopropyl, cyclobutyl, cyclopentyl, cyclohexyl, cycloheptyl and the like.

The term "$C_2$-$C_6$ dialkylamino" is intended to mean an amino substituted with two of the same or different $C_1$-$C_3$ alkyl radicals wherein alkyl radical has the same definition as described herein. Some examples include, but are not limited to, dimethylamino, methylethylamino, diethylamino, methylpropylamino, methylisopropylamino, ethylpropylamino, ethylisopropylamino, dipropylamino, propylisopropylamino and the like. Some embodiments are "$C_2$-$C_4$ dialkylamino."

The term "$C_2$-$C_6$ dialkylcarboxamido" or "$C_2$-$C_6$ dialkylcarboxamide" is intended to mean two alkyl radicals, that are the same or different, attached to an amide group, wherein alkyl has the same definition as described herein. A $C_2$-$C_6$ dialkylcarboxamido may be represented by the following groups:

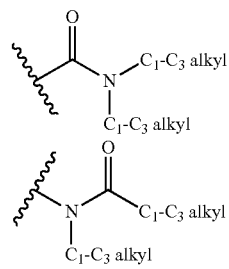

wherein $C_1$-$C_3$ has the same definition as described herein. Examples of a dialkylcarboxamide include, but are not limited to, N,N-dimethylcarboxamide, N-methyl-N-ethylcarboxamide, N,N-diethylcarboxamide, N-methyl-N-isopropylcarboxamide, and the like.

The term "$C_2$-$C_6$ dialkylsulfonamide" is intended to mean one of the following groups shown below:

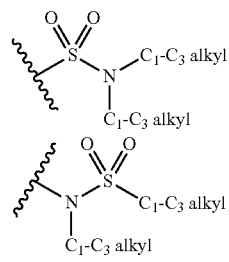

wherein $C_1$-$C_3$ has the same definition as described herein, for example but not limited to, methyl, ethyl, n-propyl, isopropyl, and the like.

The term "$C_1$-$C_6$ haloalkoxy" is intended to mean a $C_1$-$C_6$ haloalkyl, as defined herein, which is directly attached to an oxygen atom. Examples include, but are not limited to, difluoromethoxy, trifluoromethoxy, 2,2,2-trifluoroethoxy, pentafluoroethoxy and the like.

The term "$C_1$-$C_6$ haloalkyl" is intended to mean an $C_1$-$C_6$ alkyl group, defined herein, wherein the alkyl is substituted with one halogen up to fully substituted and a fully substituted $C_1$-$C_6$ haloalkyl can be represented by the formula $C_nL_{2n+1}$ wherein L is a halogen and "n" is 1, 2, 3, 4, 5 or 6; when more than one halogen is present then they may be the same or different and selected from the group consisting of F, Cl, Br and I, preferably F, some embodiments are 1 to 5 carbons, some embodiments are 1 to 4 carbons, some embodiments are 1 to 3 carbons, and some embodiments are 1 or 2 carbons. Examples of haloalkyl groups include, but are not limited to, fluoromethyl, difluoromethyl, trifluoromethyl, chlorodifluoromethyl, 2,2,2-trifluoroethyl, pentafluoroethyl and the like.

The term "$C_1$-$C_6$ haloalkylsulfinyl" is intended to mean a $C_1$-$C_6$ haloalkyl radical attached to the sulfur atom of a sulfoxide group having the formula: —S(O)— wherein the haloalkyl radical has the same definition as described herein. Examples include, but are not limited to, trifluoromethylsulfinyl, 2,2,2-trifluoroethylsulfinyl, 2,2-difluoroethylsulfinyl and the like.

The term "$C_1$-$C_6$ haloalkylsulfonyl" is intended to mean a $C_1$-$C_6$ haloalkyl radical attached to the sulfur atom of a sulfone group having the formula: —S(O)$_2$— wherein haloalkyl has the same definition as described herein. Examples include, but are not limited to, trifluoromethylsulfonyl, 2,2,2-trifluoroethylsulfonyl, 2,2-difluoroethylsulfonyl and the like.

The term "$C_1$-$C_6$ haloalkylthio" is intended to mean a $C_1$-$C_6$ haloalkyl radical directly attached to a sulfur wherein the haloalkyl has the same meaning as described herein. Examples include, but are not limited to, trifluoromethylthio (i.e., $CF_3S$—, also referred to as trifluoromethylsulfanyl), 1,1-difluoroethylthio, 2,2,2-trifluoroethylthio and the like.

The term "halogen" or "halo" is intended to mean to a fluoro, chloro, bromo or iodo group.

The term "heteroaryl" is intended to mean an aromatic ring system that may be a single ring, two fused rings or three fused rings wherein at least one ring carbon is replaced with a heteroatom selected from, for example, but not limited to, the group consisting of O, S and N wherein the N can be optionally substituted with H, $C_1$-$C_4$ acyl or $C_1$-$C_4$ alkyl. Examples of heteroaryl groups include, but are not limited to, pyridyl, benzofuranyl, pyrazinyl, pyridazinyl, pyrimidinyl, triazinyl, quinolinyl, benzoxazolyl, benzothiazolyl, 1H-benzimidazolyl, isoquinolinyl, quinazolinyl, quinoxalinyl and the like. In some embodiments, the heteroatom is selected from, for example, but not limited to, the group consisting of O, S and N, wherein N is substituted with H (i.e., NH), examples include, but are not limited to, pyrrolyl, indolyl, 1H-benzoimidazol-2-yl, and the like.

The term "$C_3$-$C_7$ heterocyclic" or "$C_3$-$C_7$ heterocyclyl" is intended to mean a non-aromatic carbon ring (i.e., $C_3$-$C_7$ cycloalkyl or $C_4$-$C_7$ cycloalkenyl as defined herein) wherein one, two or three ring carbons are replaced by a heteroatom selected from, for example, but not limited to, the group consisting of O, S, S(=O), S(=O)$_2$, NH, wherein the N can be optionally substituted as described herein. In some embodiments, the nitrogen is optionally substituted with $C_1$-$C_4$ acyl or $C_1$-$C_4$ alkyl, and ring carbon atoms are optionally substituted with oxo or a thiooxo thus forming a carbonyl or thiocarbonyl group. The heterocyclic group can be attached/bonded to any available ring atom, for example, ring carbon, ring nitrogen, and the like. The heterocyclic group is a 3-, 4-, 5-, 6- or 7-membered ring. Examples of a heterocyclic group include, but are not limited to, aziridin-1-yl, aziridin-2-yl, azetidin-1-yl, azetidin-2-yl, azetidin-3-yl, piperidin-1-yl, piperidin-2-yl, piperidin-3-yl, piperidin-4-yl, morpholin-2-yl, morpholin-3-yl, morpholin-4-yl, piperzin-1-yl, piperzin-2-yl, piperzin-3-yl, piperzin-4-yl, pyrrolidin-1-yl, pyrrolidin-2-yl, pyrrolidin-3-yl, [1,3]-dioxolan-2-yl, thiomorpholin-$C_4$-yl, [1,4]oxazepan-4-yl, 1,1-dioxothiomorpholin-4-yl, azepan-1-yl, azepan-2-yl, azepan-3-yl, azepan-4-yl, tetrahydrofuran-2-yl, tetrahydrofuran-3-yl, and the like.

The term "hydroxyl" is intended to mean the group —OH.
The term "nitro" is intended to mean the group —NO$_2$.
The term "oxo" is intended to mean the substituent =O, accordingly, as a result, when a carbon is substituted by an "oxo" group the new group resulting from the carbon and oxo together is a carbonyl group.
The term "sulfonamide" is intended to mean the group —SO$_2$NH$_2$.
The term "thiol" is intended to mean the group —SH.

Compounds of the Invention:

One aspect of the present invention pertains to certain compounds as shown in Formula (Ia):

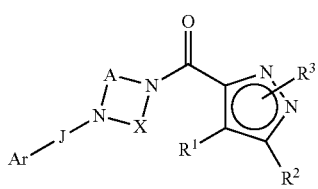

or a pharmaceutically acceptable salt, hydrate or solvate thereof; wherein R$^1$, R$^2$, R$^3$, Ar, A, X and J have the same definitions as described herein, supra and infra.

In some embodiments, the compounds of the present invention are other than 1-(4-(1H-pyrazole-3-carbonyl)piperazin-1-yl)-2-(4-fluoro-1H-indol-3-yl)ethane-1,2-dione, represented by the formula below:

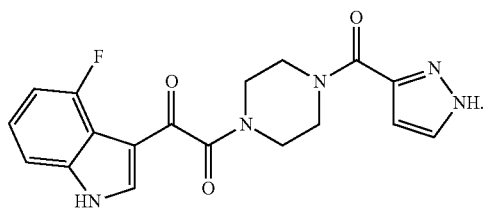 [SMILES: O=C(C(=O)N1CCN(C(=O)c2cc[nH]n2)CC1)c1c[nH]c2cccc(F)c12]

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination. All combinations of the embodiments pertaining to the chemical groups represented by the variables (e.g., R$^1$, R$^2$, R$^3$, Ar, A, X and J) contained within the generic chemical formulae described herein, for example, (Ia, Ic and Ie) are specifically embraced by the present invention just as if they were explicitly disclosed, to the extent that such combinations embrace compounds that result in stable compounds (i.e., compounds that can be isolated, characterized and tested for biological activity). In addition, all subcombinations of the chemical groups listed in the embodiments describing such variables, as well as all subcombinations of uses and medical indications described herein, are also specifically embraced by the present invention just as if each of such subcombination of chemical groups and subcombination of uses and medical indications were explicitly disclosed herein.

As used herein, "substituted" indicates that at least one hydrogen atom of the chemical group is replaced by a non-hydrogen substituent or group, the non-hydrogen substituent or group can be monovalent or divalent. When the substituent or group is divalent, then it is understood that this group is further substituted with another substituent or group. When a chemical group herein is "substituted" it may have up to the full valance of substitution; for example, a methyl group can be substituted by 1, 2, or 3 substituents, a methylene group can be substituted by 1 or 2 substituents, a phenyl group can be substituted by 1, 2, 3, 4, or 5 substituents, a naphthyl group can be substituted by 1, 2, 3, 4, 5, 6, or 7 substituents and the like. Likewise, "substituted with one or more substituents" refers to the substitution of a group with one substituent up to the total number of substituents physically allowed by the group. Further, when a group is substituted with more than one group they can be identical or they can be different.

Compounds of the invention can also include tautomeric forms, such as keto-enol tautomers, and the like. Tautomeric forms can be in equilibrium or sterically locked into one form by appropriate substitution. It is understood that the various tautomeric forms are within the scope of the compounds of the present invention.

Compounds of the invention can also include all isotopes of atoms occurring in the intermediates and/or final compounds. Isotopes include those atoms having the same atomic number but different mass numbers. For example, isotopes of hydrogen include deuterium and tritium.

It is understood and appreciated that compounds of Formula (Ia) and formulae related therefrom may have one or more chiral centers, and therefore can exist as enantiomers and/or diastereomers. The invention is understood to extend to and embrace all such enantiomers, diastereomers and mixtures thereof, including but not limited to racemates. It is understood that compounds of Formula (Ia) and formulae used throughout this disclosure are intended to represent all individual enantiomers and mixtures thereof, unless stated or shown otherwise.

Some embodiments of the present invention pertain to compounds of Formula (Ic):

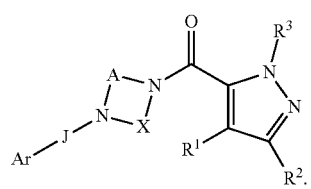

Some embodiments of the present invention pertain to compounds of Formula (Ie):

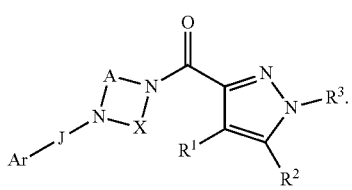

In some embodiments, each R$^1$ and R$^2$ is selected independently from the group consisting of H, C$_1$-C$_6$ alkyl, C$_1$-C$_6$ alkylaryl, aryl, C$_3$-C$_7$ cycloalkyl, C$_1$-C$_6$ haloalkyl, halogen, heteroaryl, and nitro.

In some embodiments, R$^1$ and R$^2$ is selected independently from the group consisting of H, methyl, ethyl, isopropyl, t-butyl, 2-methylphenyl, phenyl, cyclopropyl, trifluoromethyl, fluoro, chloro, bromo, iodo, furan-2-yl and nitro.

In some embodiments, $R^1$ is H, halogen or $C_1$-$C_6$ alkylaryl; and $R^2$ is H, $C_1$-$C_6$ alkyl, aryl, $C_3$-$C_7$ cycloalkyl, $C_1$-$C_6$ haloalkyl, heteroaryl or nitro.

In some embodiments, $R^1$ is H, fluoro, chloro, bromo, iodo or 2-methylphenyl and $R^2$ is H, methyl, ethyl, isopropyl, t-butyl, phenyl, cyclopropyl, trifluoromethyl, furan-2-yl or nitro.

In some embodiments, $R^1$ and $R^2$ together with the carbon atoms to which they are bonded form a $C_3$-$C_7$ carbocyclyl.

In some embodiments, $R^1$ and $R^2$ together with the carbon atoms to which they are bonded form a $C_5$ carbocyclyl.

In some embodiments, $R^3$ is selected from the group consisting of H, $C_1$-$C_6$ alkyl and aryl; and wherein aryl is optionally substituted with $C_1$-$C_6$ alkoxy.

In some embodiments, $R^3$ is selected from the group consisting of H, $C_1$-$C_6$ alkyl and aryl; and wherein aryl is optionally substituted with methoxy.

In some embodiments, $R^3$ is selected from the group consisting of H, methyl, ethyl, t-butyl, phenyl and 4-methoxyphenyl.

In some embodiments, A and X are each —$CH_2CH_2$—, each optionally substituted with $C_1$-$C_3$ alkyl.

In some embodiments, A and X are each —$CH_2CH_2$—, each optionally substituted with methyl.

In some embodiments, A and X are each independently —$CH_2CH_2$— or —$CH(CH_3)CH_2$—.

In some embodiments, J is —$CH_2CH_2$— optionally substituted with 1, 2, 3 or 4 substituents selected independently from the group consisting of $C_1$-$C_3$ alkyl, hydroxyl, oxo and =NO—$C_1$-$C_3$ alkyl.

In some embodiments, J is —$CH_2CH_2$— optionally substituted with 1, 2, 3 or 4 substituents selected independently from the group consisting of methyl, hydroxyl, oxo and =$NOCH_3$.

In some embodiments, J is —$CH_2CH_2$—, —C(=$NOCH_3$)$CH_2$—, —C=$OCH_2$—, —CH($CH_3$)$CH_2$—, —C($CH_3$)$_2CH_2$—, or —$CHOHCH_2$—.

In some embodiments, Ar is aryl or heteroaryl each optionally substituted with 1, 2, 3, 4 or 5 substituents selected independently from the group consisting of $C_1$-$C_6$ alkoxy, $C_1$-$C_6$ alkylsulfonyl, $C_1$-$C_6$ haloalkoxy, $C_1$-$C_6$ haloalkyl, halogen and heterocyclyl.

In some embodiments, Ar is aryl or heteroaryl each optionally substituted with 1, 2, 3, 4 or 5 substituents selected independently from the group consisting of methoxy, methanesulfonyl, trifluoromethoxy, trifluoromethyl, fluoro, chloro and pyrrolidin-1-yl.

In some embodiments, Ar is naphthyl, 2-methoxyphenyl, 4-methoxyphenyl, 4-methanesulfonylphenyl, 4-trifluoromethoxyphenyl, 4-trifluoromethylphenyl, 2-fluorophenyl, 3-fluorophenyl, 4-fluorophenyl, 2,4-difluorophenyl, 3,4-difluorophenyl, 2-chlorophenyl, 3-chlorophenyl, 4-chlorophenyl and 6-chloro-1,3-dihydro-indol-2-one.

Some embodiments of the present invention pertain to compounds of Formula (Ic):

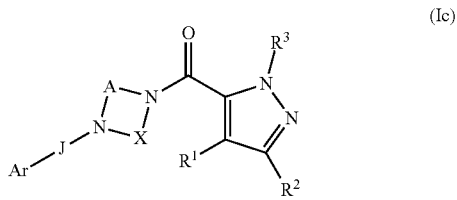

(Ic)

or a pharmaceutically acceptable salt, solvate or hydrate thereof;

wherein:
$R^1$ is H, halogen or $C_1$-$C_6$ alkylaryl;
$R^2$ is H, $C_1$-$C_6$ alkyl, aryl, $C_3$-$C_7$ cycloalkyl, $C_1$-$C_6$ haloalkyl, heteroaryl, or nitro; or
$R^1$ and $R^2$ together with the carbon atoms to which they are bonded form a $C_3$-$C_7$ carbocyclyl;
$R^3$ is H, $C_1$-$C_6$ alkyl, aryl, or aryl substituted with $C_1$-$C_6$ alkoxy;
A and X are each —$CH_2CH_2$—, each optionally substituted with $C_1$-$C_3$ alkyl;
J is —$CH_2CH_2$— optionally substituted with 1, 2, 3 or 4 substituents selected independently from the group consisting of $C_1$-$C_3$ alkyl, hydroxyl, oxo and =NO—$C_1$-$C_3$ alkyl; and
Ar is aryl or heteroaryl each optionally substituted with 1, 2, 3, 4 or 5 substituents selected independently from the group consisting of $C_1$-$C_6$ alkoxy, $C_1$-$C_6$ alkylsulfonyl, $C_1$-$C_6$ haloalkoxy, $C_1$-$C_6$ haloalkyl, halogen and heterocyclyl.

Some embodiments of the present invention pertain to compounds of Formula (Ic):

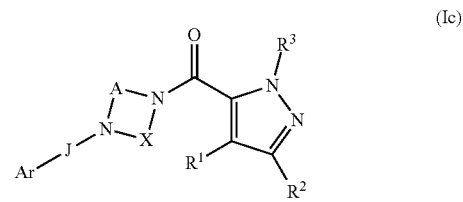

(Ic)

or a pharmaceutically acceptable salt, solvate or hydrate thereof;
wherein:
$R^1$ is H, fluoro, chloro, bromo, iodo or 2-methylphenyl;
$R^2$ is H, methyl, ethyl, isopropyl, t-butyl, phenyl, cyclopropyl, trifluoromethyl, furan-2-yl or nitro; or
$R^1$ and $R^2$ together with the carbon atoms to which they are bonded form a $C_5$ carbocyclyl;
$R^3$ is H, methyl, ethyl, t-butyl, phenyl or 4-methoxyphenyl;
A and X are each independently —$CH_2CH_2$— or —CH($CH_3$)$CH_2$—;
J is —$CH_2CH_2$—, —C(=NOMe)$CH_2$—, —C=$OCH_2$—, —CH($CH_3$)$CH_2$—, —C($CH_3$)$_2CH_2$—, or —$CHOHCH_2$—; and
Ar is naphthyl, 2-methoxyphenyl, 4-methoxyphenyl, 4-methanesulfonylphenyl, 4-trifluoromethoxyphenyl, 4-trifluoromethylphenyl, 2-fluorophenyl, 3-fluorophenyl, 4-fluorophenyl, 2,4-difluorophenyl, 3,4-difluorophenyl, 2-chlorophenyl, 3-chlorophenyl, 4-chlorophenyl and 6-chloro-1,3-dihydro-indol-2-one.

Some embodiments of the present invention pertain to compounds of Formula (Ie):

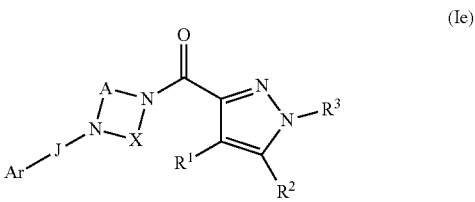

(Ie)

or a pharmaceutically acceptable salt, solvate or hydrate thereof;

wherein:

$R^1$ is H, halogen or $C_1$-$C_6$ alkylaryl;

$R^2$ is H, $C_1$-$C_6$ alkyl, aryl, $C_3$-$C_7$ cycloalkyl, $C_1$-$C_6$ haloalkyl, heteroaryl, or nitro; or $R^1$ and $R^2$ together with the carbon atoms to which they are bonded form a $C_3$-$C_7$ carbocyclyl;

$R^3$ is H, $C_1$-$C_6$ alkyl, aryl, or aryl substituted with $C_1$-$C_6$ alkoxy;

A and X are each —$CH_2CH_2$—, each optionally substituted with $C_1$-$C_3$ alkyl;

J is —$CH_2CH_2$— optionally substituted with 1, 2, 3 or 4 substituents selected independently from the group consisting of $C_1$-$C_3$ alkyl, hydroxyl, oxo and =NO—$C_1$-$C_3$ alkyl; and Ar is aryl or heteroaryl each optionally substituted with 1, 2, 3, 4 or 5 substituents selected independently from the group consisting of $C_1$-$C_6$ alkoxy, $C_1$-$C_6$ alkylsulfonyl, $C_1$-$C_6$ haloalkoxy, $C_1$-$C_6$ haloalkyl, halogen and heterocyclyl.

Some embodiments of the present invention pertain to compounds of Formula (Ie):

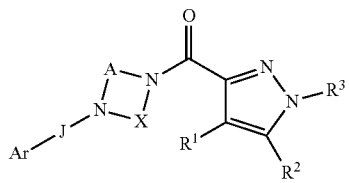

(Ie)

or a pharmaceutically acceptable salt, solvate or hydrate thereof;

wherein:

$R^1$ is H, fluoro, chloro, bromo, iodo or 2-methylphenyl;

$R^2$ is H, methyl, ethyl, isopropyl, t-butyl, phenyl, cyclopropyl, trifluoromethyl, furan-2-yl or nitro; or $R^1$ and $R^2$ together with the carbon atoms to which they are bonded form a $C_5$ carbocyclyl;

$R^3$ is H, methyl, ethyl, t-butyl, phenyl or 4-methoxyphenyl;

A and X are each independently —$CH_2CH_2$— or —$CH(CH_3)CH_2$—;

J is —$CH_2CH_2$—, —C(=NOMe)$CH_2$—, —C=O$CH_2$—, —$CH(CH_3)CH_2$—, —$C(CH_3)_2CH_2$—, or —$CHOHCH_2$—; and Ar is naphthyl, 2-methoxyphenyl, 4-methoxyphenyl, 4-methanesulfonylphenyl, 4-trifluoromethoxyphenyl, 4-trifluoromethylphenyl, 2-fluorophenyl, 3-fluorophenyl, 4-fluorophenyl, 2,4-difluorophenyl, 3,4-difluorophenyl, 2-chlorophenyl, 3-chlorophenyl, 4-chlorophenyl and 6-chloro-1,3-dihydro-indol-2-one.

In some embodiments, where $R^1$, $R^2$ and $R^3$ are all H; and A and X are both —$CH_2CH_2$—; and J is $(CO)_2$; then Ar is a moiety other than heteroaryl substituted with halogen.

Some embodiments of the present invention include every combination of one or more compounds selected from the following group shown in TABLE A.

TABLE A

| Cmpd No. | Chemical Structure | Chemical Name |
|---|---|---|
| 1 | 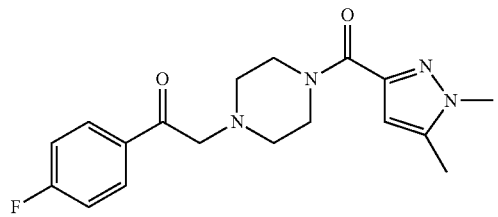 [SMILES: Cc1cc(C(=O)N2CCN(CC(=O)c3ccc(F)cc3)CC2)nn1C] | 2-[4-(1,5-Dimethyl-1H-pyrazole-3-carbonyl)-piperazin-1-yl]-1-(4-fluoro-phenyl)-ethanone |
| 2 | 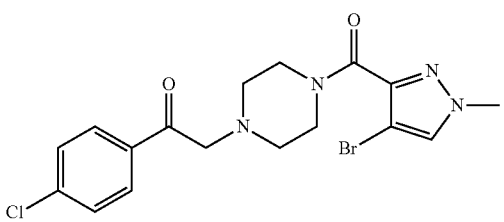 [SMILES: Cn1cc(Br)c(C(=O)N2CCN(CC(=O)c3ccc(Cl)cc3)CC2)n1] | (4-Bromo-1-methyl-1H-pyrazol-3-yl)-{4-[2-(4-chloro-phenyl)-ethyl]-piperazin-1-yl}-methanone |
| 3 | 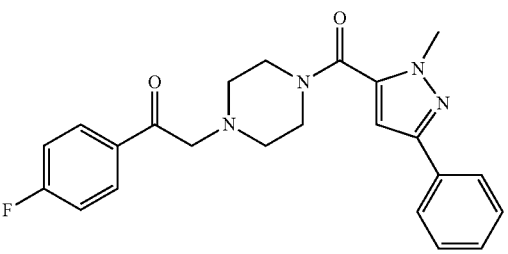 [SMILES: Cn1nc(-c2ccccc2)cc1C(=O)N1CCN(CC(=O)c2ccc(F)cc2)CC1] | 1-(4-Fluoro-phenyl)-2-[4-(2-methyl-5-phenyl-2H-pyrazole-3-carbonyl)-piperazin-1-yl]-ethanone |

TABLE A-continued

| Cmpd No. | Chemical Structure | Chemical Name |
|---|---|---|
| 4 | 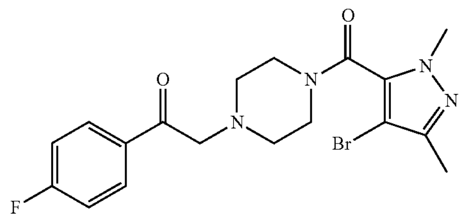 [SMILES: Cc1nn(C)c(C(=O)N2CCN(CC(=O)c3ccc(F)cc3)CC2)c1Br] | 2-[4-(4-Bromo-2,5-dimethyl-2H-pyrazole-3-carbonyl)-piperazin-1-yl]-1-(4-fluoro-phenyl)-ethanone |
| 5 | 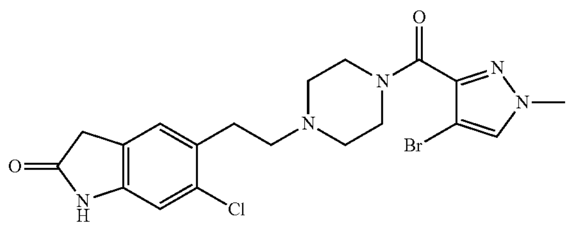 [SMILES: Cn1cc(Br)c(C(=O)N2CCN(CCc3cc4c(cc3Cl)NC(=O)C4)CC2)n1] | 5-{2-[4-(4-Bromo-1-methyl-1H-pyrazole-3-carbonyl)-piperazin-1-yl]-ethyl}-6-chloro-1,3-dihydro-indol-2-one |
| 6 | 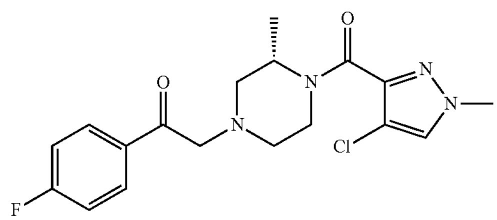 [SMILES: C[C@H]1CN(CC(=O)c2ccc(F)cc2)CCN1C(=O)c1nn(C)cc1Cl] | 2-{(S)-4-(4-Chloro-1-methyl-1H-pyrazole-3-carbonyl)-3-methyl-piperazin-1-yl]-1-(4-fluoro-phenyl)-ethanone |
| 7 | 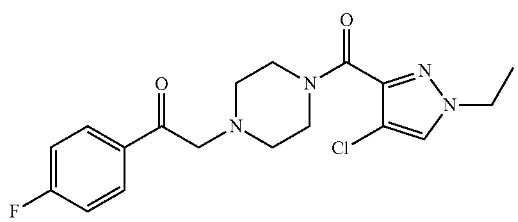 [SMILES: CCn1cc(Cl)c(C(=O)N2CCN(CC(=O)c3ccc(F)cc3)CC2)n1] | 2-[4-(4-Chloro-1-ethyl-1H-pyrazole-3-carbonyl)-piperazin-1-yl]-1-(4-fluoro-phenyl)-ethanone |
| 8 | 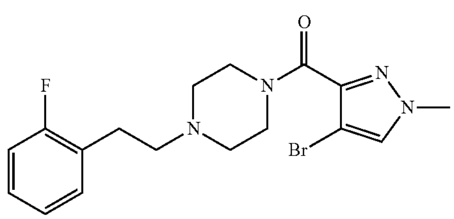 [SMILES: Cn1cc(Br)c(C(=O)N2CCN(CCc3ccccc3F)CC2)n1] | (4-Bromo-1-methyl-1H-pyrazol-3-yl)-{4-[2-(2-fluoro-phenyl)-ethyl]-piperazin-1-yl}-methanone |
| 9 | 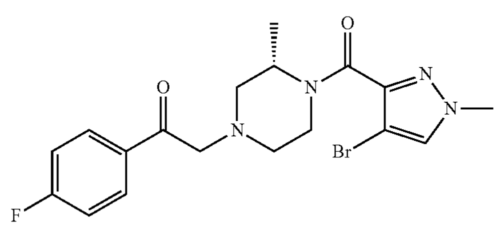 [SMILES: C[C@H]1CN(CC(=O)c2ccc(F)cc2)CCN1C(=O)c1nn(C)cc1Br] | 2-[(S)-4-(4-Bromo-1-methyl-1H-pyrazole-3-carbonyl)-3-methyl-piperazin-1-yl]-1-(4-fluoro-phenyl)-ethanone |
| 10 | 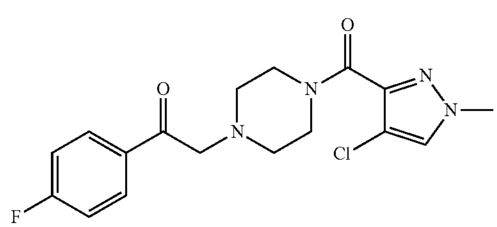 [SMILES: Cn1cc(Cl)c(C(=O)N2CCN(CC(=O)c3ccc(F)cc3)CC2)n1] | 2-[4-(4-Chloro-1-methyl-1H-pyrazole-3-carbonyl)-piperazin-1-yl]-1-(4-fluoro-phenyl)-ethanone |

TABLE A-continued

| Cmpd No. | Chemical Structure | Chemical Name |
| --- | --- | --- |
| 11 | 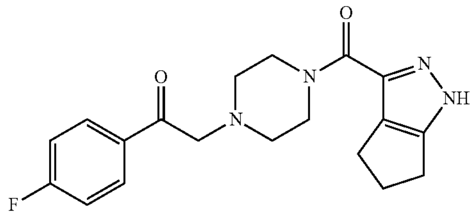 [SMILES: O=C(CN1CCN(C(=O)c2n[nH]c3c2CCC3)CC1)c1ccc(F)cc1] | 1-(4-Fluoro-phenyl)-2-[4-(1,4,5,6-tetrahydro-cyclopentapyrazole-3-carbonyl)-piperazin-1-yl]-ethanone |
| 12 | 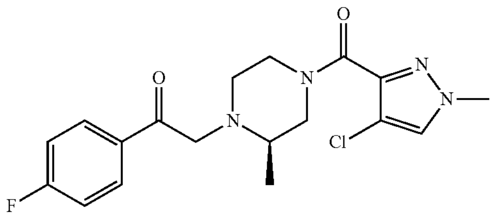 [SMILES: C[C@@H]1CN(C(=O)c2nn(C)cc2Cl)CCN1CC(=O)c1ccc(F)cc1] | 2-[(R)-4-(4-Chloro-1-methyl-1H-pyrazole-3-carbonyl)-2-methyl-piperazin-1-yl]-1-(4-fluoro-phenyl)-ethanone |
| 13 | 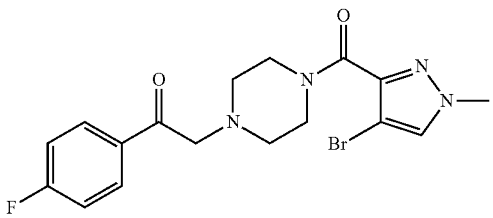 [SMILES: Cn1cc(Br)c(C(=O)N2CCN(CC(=O)c3ccc(F)cc3)CC2)n1] | 2-[4-(4-Bromo-1-methyl-1H-pyrazole-3-carbonyl)-piperazin-1-yl]-1-(4-fluoro-phenyl)-ethanone |
| 14 | 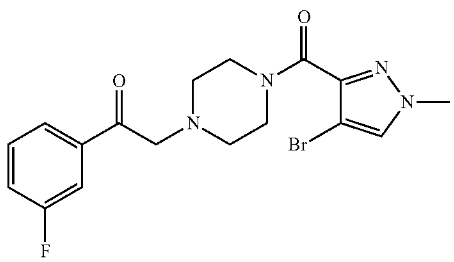 [SMILES: Cn1cc(Br)c(C(=O)N2CCN(CC(=O)c3cccc(F)c3)CC2)n1] | 2-[4-(4-Bromo-1-methyl-1H-pyrazole-3-carbonyl)-piperazin-1-yl]-1-(3-fluoro-phenyl)-ethanone |
| 15 | 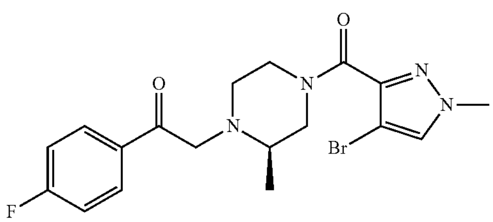 [SMILES: C[C@@H]1CN(C(=O)c2nn(C)cc2Br)CCN1CC(=O)c1ccc(F)cc1] | 2-[(R)-4-(4-Bromo-1-methyl-1H-pyrazole-3-carbonyl)-2-methyl-piperazin-1-yl]-1-(4-fluoro-phenyl)-ethanone |
| 16 | 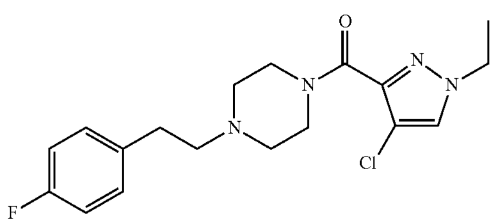 [SMILES: CCn1cc(Cl)c(C(=O)N2CCN(CCc3ccc(F)cc3)CC2)n1] | (4-Chloro-1-ethyl-1H-pyrazol-3-yl)-{4-[2-(4-fluoro-phenyl)-ethyl]-piperazin-1-yl}-methanone |
| 17 | 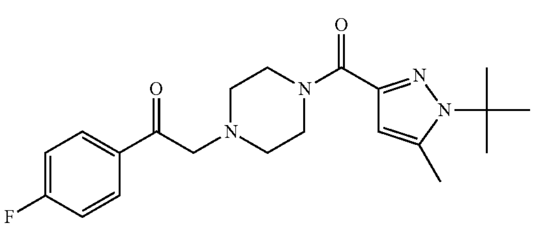 [SMILES: Cc1cc(C(=O)N2CCN(CC(=O)c3ccc(F)cc3)CC2)nn1C(C)(C)C] | 2-[4-(1-tert-Butyl-5-methyl-1H-pyrazole-3-carbonyl)-piperazin-1-yl]-1-(4-fluoro-phenyl)-ethanone |

TABLE A-continued

| Cmpd No. | Chemical Structure | Chemical Name |
|---|---|---|
| 18 | 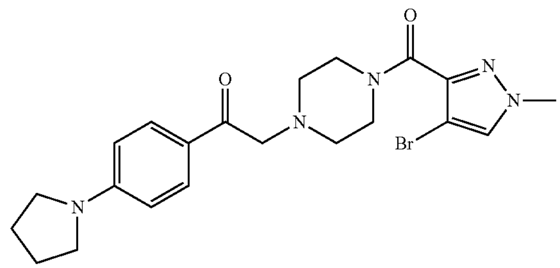 [SMILES: Cn1cc(Br)c(C(=O)N2CCN(CC(=O)c3ccc(N4CCCC4)cc3)CC2)n1] | 2-[4-(4-Bromo-1-methyl-1H-pyrazole-3-carbonyl)-piperazin-1-yl]-1-(4-pyrrolidin-1-yl-phenyl)-ethanone |
| 19 | 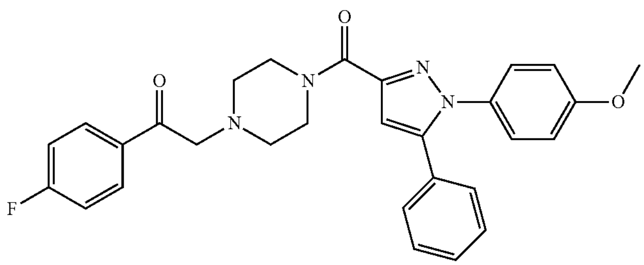 [SMILES: COc1ccc(-n2nc(C(=O)N3CCN(CC(=O)c4ccc(F)cc4)CC3)cc2-c2ccccc2)cc1] | 1-(4-Fluoro-phenyl)-2-{4-[1-(4-methoxy-phenyl)-5-phenyl-1H-pyrazole-3-carbonyl]-piperazin-1-yl}-ethanone |
| 20 | 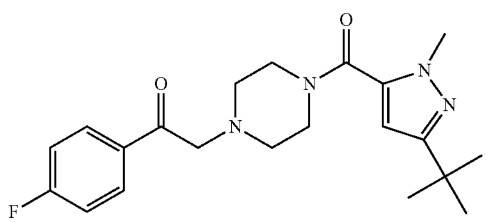 [SMILES: Cn1nc(C(C)(C)C)cc1C(=O)N1CCN(CC(=O)c2ccc(F)cc2)CC1] | 2-[4-(5-tert-Butyl-2-methyl-2H-pyrazole-3-carbonyl)-piperazin-1-yl]-1-(4-fluoro-phenyl)-ethanone |
| 21 | 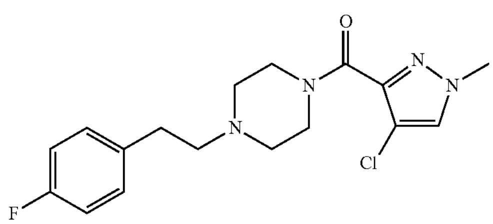 [SMILES: Cn1cc(Cl)c(C(=O)N2CCN(CCc3ccc(F)cc3)CC2)n1] | (4-Chloro-1-methyl-1H-pyrazol-3-yl)-{4-[2-(4-fluoro-phenyl)-ethyl]-piperazin-1-yl}-methanone |
| 22 | 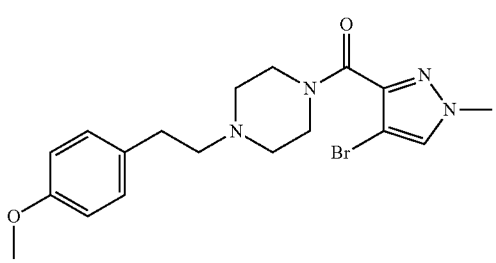 [SMILES: COc1ccc(CCN2CCN(C(=O)c3nn(C)cc3Br)CC2)cc1] | (4-Bromo-1-methyl-1H-pyrazol-3-yl)-{4-[2-(4-methoxy-phenyl)-ethyl]-piperazin-1-yl}-methanone |
| 23 | 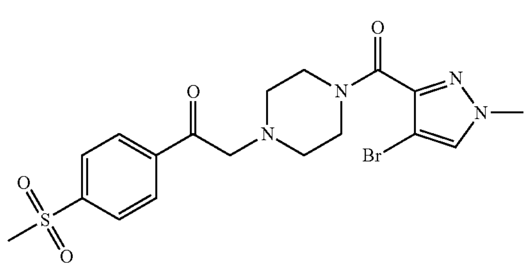 | 2-[4-(4-Bromo-1-methyl-1H-pyrazole-3-carbonyl)-piperazin-1-yl]-1-(4-methanesulfonyl-phenyl)-ethanone |

TABLE A-continued

| Cmpd No. | Chemical Structure | Chemical Name |
|---|---|---|
| 24 | 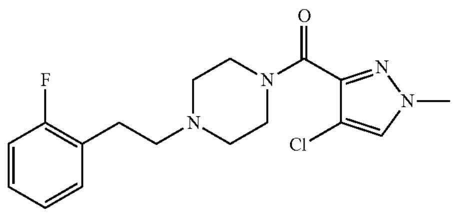 [SMILES: Cn1cc(Cl)c(C(=O)N2CCN(CCc3ccccc3F)CC2)n1] | (4-Chloro-1-methyl-1H-pyrazol-3-yl)-{4-[2-(2-fluoro-phenyl)-ethyl]-piperazin-1-yl}-methanone |
| 25 | 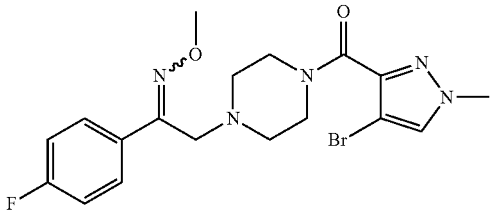 [SMILES: CON=C(CN1CCN(C(=O)c2nn(C)cc2Br)CC1)c1ccc(F)cc1] | 2-[4-(4-Bromo-1-methyl-1H-pyrazole-3-carbonyl)-piperazin-1-yl]-1-(4-fluoro-phenyl)-ethanone O-methyl-oxime |
| 26 | 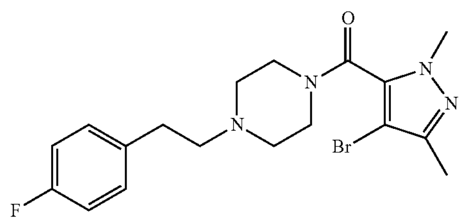 [SMILES: Cc1nn(C)c(C(=O)N2CCN(CCc3ccc(F)cc3)CC2)c1Br] | (4-Bromo-2,5-dimethyl-2H-pyrazol-3-yl)-{4-[2-(4-fluoro-phenyl)-ethyl]-piperazin-1-yl}-methanone |
| 27 | 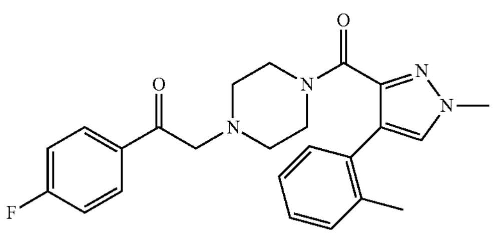 [SMILES: Cc1ccccc1-c1cn(C)nc1C(=O)N1CCN(CC(=O)c2ccc(F)cc2)CC1] | 1-(4-Fluoro-phenyl)-2-[4-(1-methyl-4-o-tolyl-1H-pyrazole-3-carbonyl)-piperazin-1-yl]-ethanone |
| 28 | 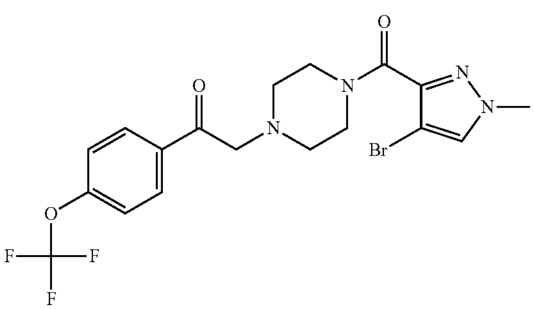 [SMILES: Cn1cc(Br)c(C(=O)N2CCN(CC(=O)c3ccc(OC(F)(F)F)cc3)CC2)n1] | 2-[4-(4-Bromo-1-methyl-1H-pyrazole-3-carbonyl)-piperazin-1-yl]-1-(4-trifluoromethoxy-phenyl)-ethanone |
| 29 | 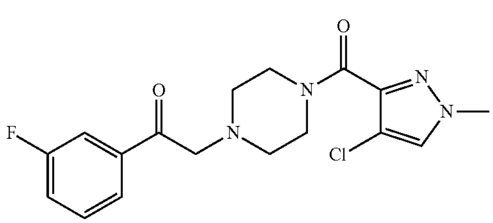 [SMILES: Cn1cc(Cl)c(C(=O)N2CCN(CC(=O)c3cccc(F)c3)CC2)n1] | 2-[4-(4-Chloro-1-methyl-1H-pyrazole-3-carbonyl)-piperazin-1-yl]-1-(3-fluoro-phenyl)-ethanone |

TABLE A-continued

| Cmpd No. | Chemical Structure | Chemical Name |
|---|---|---|
| 30 | 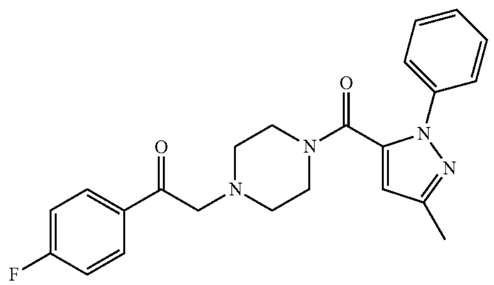 [SMILES: Cc1cc(C(=O)N2CCN(CC(=O)c3ccc(F)cc3)CC2)n(-c2ccccc2)n1] | 1-(4-Fluoro-phenyl)-2-[4-(5-methyl-2-phenyl-2H-pyrazole-3-carbonyl)-piperazin-1-yl]-ethanone |
| 31 | 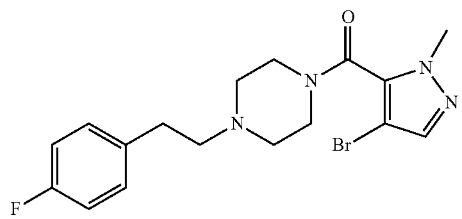 [SMILES: Cn1ncc(Br)c1C(=O)N1CCN(CCc2ccc(F)cc2)CC1] | (4-Bromo-2-methyl-2H-pyrazol-3-yl)-{4-[2-(4-fluoro-phenyl)-ethyl]-piperazin-1-yl}-methanone |
| 32 | 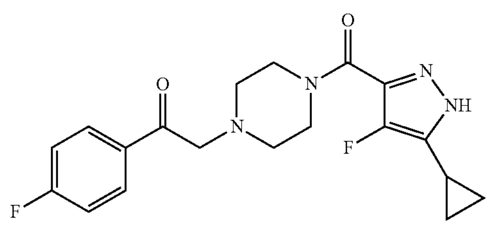 [SMILES: O=C(CN1CCN(C(=O)c2n[nH]c(C3CC3)c2F)CC1)c1ccc(F)cc1] | 2-[4-(5-Cyclopropyl-4-fluoro-1H-pyrazole-3-carbonyl)-piperazin-1-yl]-1-(4-fluoro-phenyl)-ethanone |
| 33 | 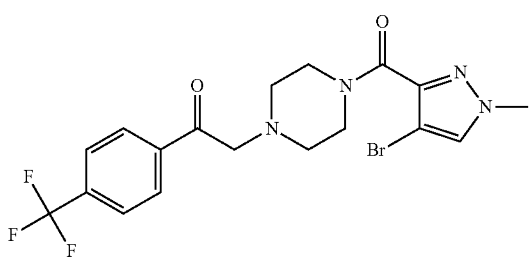 [SMILES: Cn1cc(Br)c(C(=O)N2CCN(CC(=O)c3ccc(C(F)(F)F)cc3)CC2)n1] | 2-[4-(4-Bromo-1-methyl-1H-pyrazole-3-carbonyl)-piperazin-1-yl]-1-(4-trifluoromethyl-phenyl)-ethanone |
| 34 | 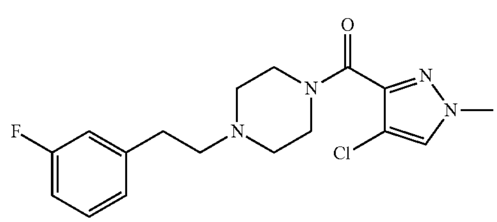 [SMILES: Cn1cc(Cl)c(C(=O)N2CCN(CCc3cccc(F)c3)CC2)n1] | (4-Chloro-1-methyl-1H-pyrazol-3-yl)-{4-[2-(3-fluoro-phenyl)-ethyl]-piperazin-1-yl}-methanone |
| 35 | 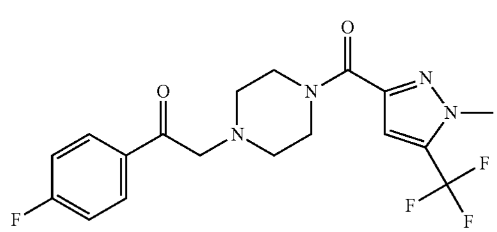 [SMILES: Cn1nc(C(=O)N2CCN(CC(=O)c3ccc(F)cc3)CC2)cc1C(F)(F)F] | 1-(4-Fluoro-phenyl)-2-[4-(1-methyl-5-trifluoromethyl-1H-pyrazole-3-carbonyl)-piperazin-1-yl]-ethanone |

TABLE A-continued

| Cmpd No. | Chemical Structure | Chemical Name |
|---|---|---|
| 36 | 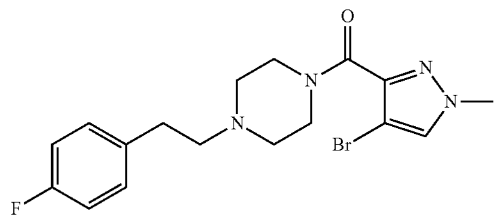 [SMILES: Cn1cc(Br)c(C(=O)N2CCN(CCc3ccc(F)cc3)CC2)n1] | (4-Bromo-1-methyl-1H-pyrazol-3-yl)-{4-[2-(4-fluoro-phenyl)-ethyl]-piperazin-1-yl}-methanone |
| 37 | 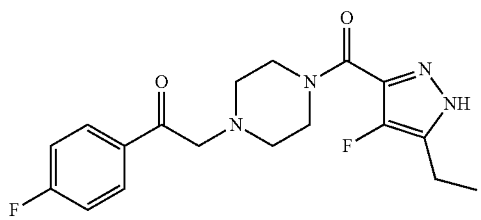 [SMILES: CCc1[nH]nc(C(=O)N2CCN(CC(=O)c3ccc(F)cc3)CC2)c1F] | 2-[4-(5-Ethyl-4-fluoro-1H-pyrazole-3-carbonyl)-piperazin-1-yl]-1-(4-fluoro-phenyl)-ethanone |
| 38 | 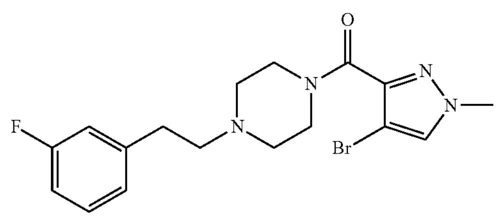 [SMILES: Cn1cc(Br)c(C(=O)N2CCN(CCc3cccc(F)c3)CC2)n1] | (4-Bromo-1-methyl-1H-pyrazol-3-yl)-{4-[2-(3-fluoro-phenyl)-ethyl]-piperazin-1-yl}-methanone |
| 39 | 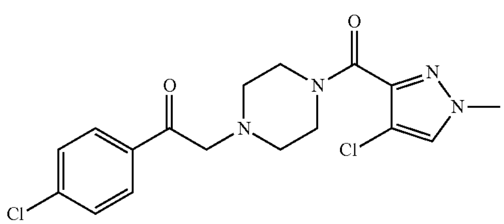 [SMILES: Cn1cc(Cl)c(C(=O)N2CCN(CC(=O)c3ccc(Cl)cc3)CC2)n1] | 2-[4-(4-Chloro-1-methyl-1H-pyrazole-3-carbonyl)-piperazin-1-yl]-1-(4-chloro-phenyl)-ethanone |
| 40 | 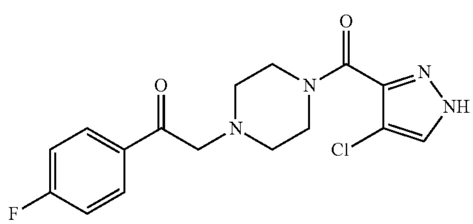 [SMILES: O=C(CN1CCN(C(=O)c2n[nH]cc2Cl)CC1)c1ccc(F)cc1] | 2-[4-(4-Chloro-1H-pyrazole-3-carbonyl)-piperazin-1-yl]-1-(4-fluoro-phenyl)-ethanone |
| 41 | 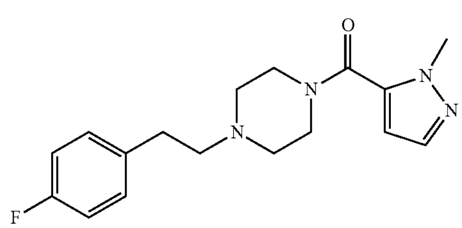 [SMILES: Cn1nccc1C(=O)N1CCN(CCc2ccc(F)cc2)CC1] | {4-[2-(4-Fluoro-phenyl)-ethyl]-piperazin-1-yl}-(2-methyl-2H-pyrazol-3-yl)-methanone |
| 42 | 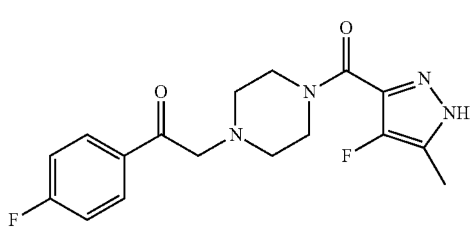 [SMILES: Cc1[nH]nc(C(=O)N2CCN(CC(=O)c3ccc(F)cc3)CC2)c1F] | 2-[4-(4-Fluoro-5-methyl-1H-pyrazole-3-carbonyl)-piperazin-1-yl]-1-(4-fluoro-phenyl)-ethanone |

TABLE A-continued

| Cmpd No. | Chemical Structure | Chemical Name |
|---|---|---|
| 43 | 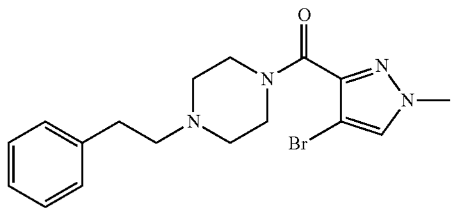 [SMILES: Cn1cc(Br)c(C(=O)N2CCN(CCc3ccccc3)CC2)n1] | (4-Bromo-1-methyl-1H-pyrazol-3-yl)-(4-phenethyl-piperazin-1-yl)-methanone |
| 44 | 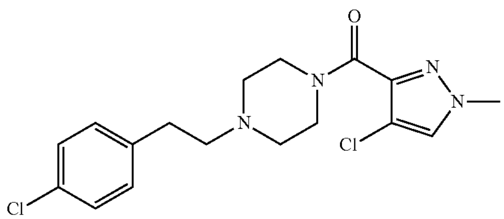 [SMILES: Cn1cc(Cl)c(C(=O)N2CCN(CCc3ccc(Cl)cc3)CC2)n1] | (4-Chloro-1-methyl-1H-pyrazol-3-yl)-{4-[2-(4-chloro-phenyl)-ethyl]-piperazin-1-yl}-methanone |
| 45 | 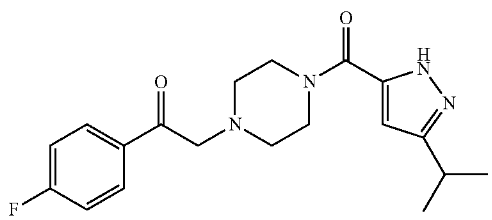 [SMILES: CC(C)c1cc(C(=O)N2CCN(CC(=O)c3ccc(F)cc3)CC2)[nH]n1] | 1-(4-Fluoro-phenyl)-2-[4-(5-isopropyl-2H-pyrazole-3-carbonyl)-piperazin-1-yl]-ethanone |
| 46 | 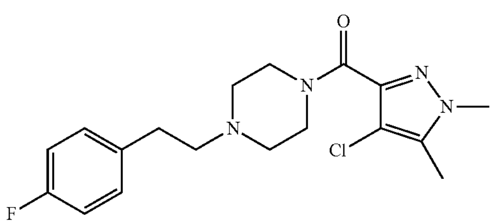 [SMILES: Cc1c(Cl)c(C(=O)N2CCN(CCc3ccc(F)cc3)CC2)nn1C] | (4-Chloro-1,5-dimethyl-1H-pyrazol-3-yl)-{4-[2-(4-fluoro-phenyl)-ethyl]-piperazin-1-yl}-methanone |
| 47 | 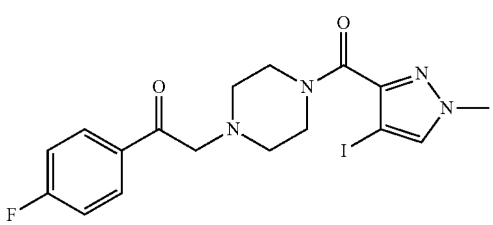 [SMILES: Cn1cc(I)c(C(=O)N2CCN(CC(=O)c3ccc(F)cc3)CC2)n1] | 1-(4-Fluoro-phenyl)-2-[4-(4-iodo-1-methyl-1H-pyrazole-3-carbonyl)-piperazin-1-yl]-ethanone |
| 48 | 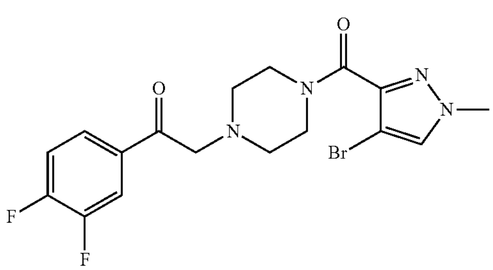 [SMILES: Cn1cc(Br)c(C(=O)N2CCN(CC(=O)c3ccc(F)c(F)c3)CC2)n1] | 2-[4-(4-Bromo-1-methyl-1H-pyrazole-3-carbonyl)-piperazin-1-yl]-1-(3,4-difluoro-phenyl)-ethanone |

TABLE A-continued

| Cmpd No. | Chemical Structure | Chemical Name |
|---|---|---|
| 49 | 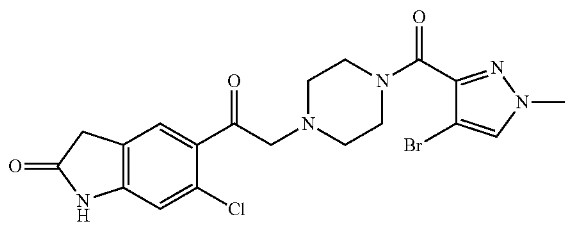 [SMILES: Cn1cc(Br)c(C(=O)N2CCN(CC(=O)c3cc4c(cc3Cl)NC(=O)C4)CC2)n1] | 5-{2-[4-(4-Bromo-1-methyl-1H-pyrazole-3-carbonyl)-piperazin-1-yl]-acetyl}-6-chloro-1,3-dihydro-indol-2-one |
| 50 | 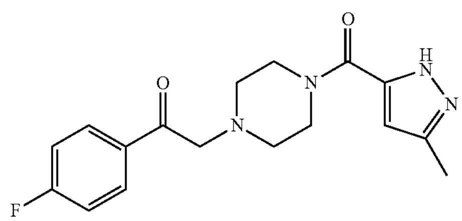 [SMILES: Cc1cc(C(=O)N2CCN(CC(=O)c3ccc(F)cc3)CC2)[nH]n1] | 1-(4-Fluoro-phenyl)-2-[4-(5-methyl-2H-pyrazole-3-carbonyl)-piperazin-1-yl]-ethanone |
| 51 | 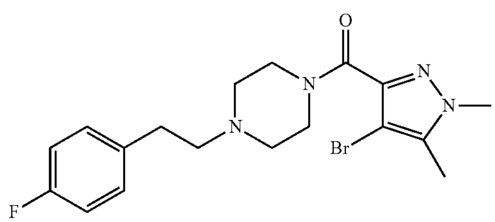 [SMILES: Cc1c(Br)c(C(=O)N2CCN(CCc3ccc(F)cc3)CC2)nn1C] | (4-Bromo-1,5-dimethyl-1H-pyrazol-3-yl)-{4-[2-(4-fluoro-phenyl)-ethyl]-piperazin-1-yl}-methanone |
| 52 | 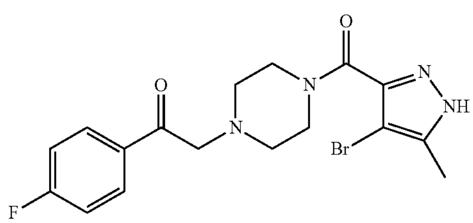 [SMILES: Cc1[nH]nc(C(=O)N2CCN(CC(=O)c3ccc(F)cc3)CC2)c1Br] | 2-[4-(4-Bromo-5-methyl-1H-pyrazole-3-carbonyl)-piperazin-1-yl]-1-(4-fluoro-phenyl)-ethanone |
| 53 | 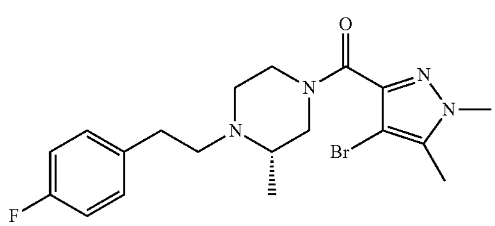 [SMILES: Cc1c(Br)c(C(=O)N2CCN(CCc3ccc(F)cc3)[C@@H](C)C2)nn1C] | (4-Bromo-1,5-dimethyl-1H-pyrazol-3-yl)-{(S)-4-[2-(4-fluoro-phenyl)-ethyl]-3-methyl-piperazin-1-yl}-methanone |
| 54 | 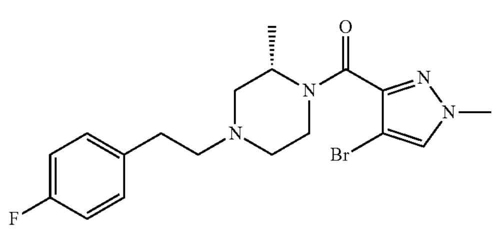 [SMILES: C[C@H]1CN(CCc2ccc(F)cc2)CCN1C(=O)c1nn(C)cc1Br] | (4-Bromo-1-methyl-1H-pyrazol-3-yl)-{(S)-4-[2-(4-fluoro-phenyl)-ethyl]-2-methyl-piperazin-1-yl}-methanone |
| 55 | 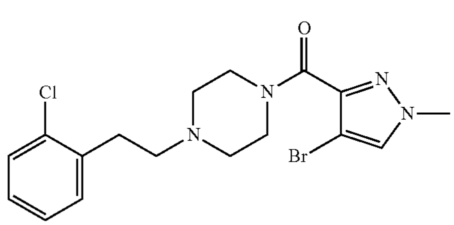 [SMILES: Cn1cc(Br)c(C(=O)N2CCN(CCc3ccccc3Cl)CC2)n1] | (4-Bromo-1-methyl-1H-pyrazol-3-yl)-{4-[2-(2-chloro-phenyl)-ethyl]-piperazin-1-yl}-methanone |

TABLE A-continued

| Cmpd No. | Chemical Structure | Chemical Name |
|---|---|---|
| 56 | 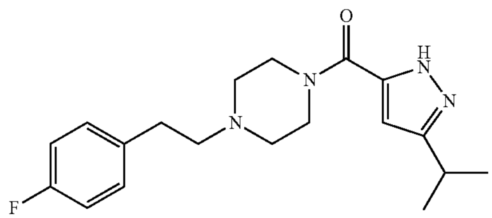 [SMILES: CC(C)c1cc(C(=O)N2CCN(CCc3ccc(F)cc3)CC2)[nH]n1] | {4-[2-(4-Fluoro-phenyl)-ethyl]-piperazin-1-yl}-(5-isopropyl-2H-pyrazol-3-yl)-methanone |
| 57 | 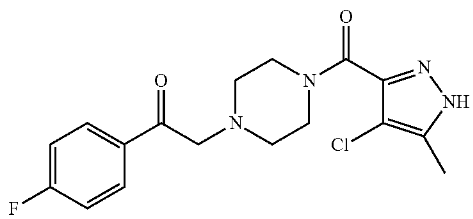 [SMILES: Cc1[nH]nc(C(=O)N2CCN(CC(=O)c3ccc(F)cc3)CC2)c1Cl] | 2-[4-(4-Chloro-5-methyl-1H-pyrazole-3-carbonyl)-piperazin-1-yl]-1-(4-fluoro-phenyl)-ethanone |
| 58 | 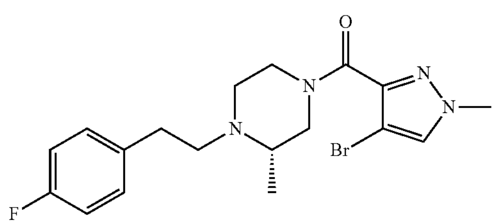 [SMILES: C[C@H]1CN(C(=O)c2nn(C)cc2Br)CCN1CCc1ccc(F)cc1] | (4-Bromo-1-methyl-1H-pyrazol-3-yl)-{(S)-4-[2-(4-fluoro-phenyl)-ethyl]-3-methyl-piperazin-1-yl}-methanone |
| 59 | 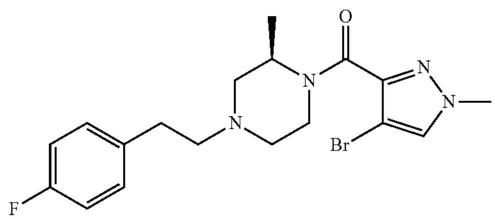 [SMILES: C[C@@H]1CN(CCc2ccc(F)cc2)CCN1C(=O)c1nn(C)cc1Br] | (4-Bromo-1-methyl-1H-pyrazol-3-yl)-{(R)-4-[2-(4-fluoro-phenyl)-ethyl]-2-methyl-piperazin-1-yl}-methanone |
| 60 | 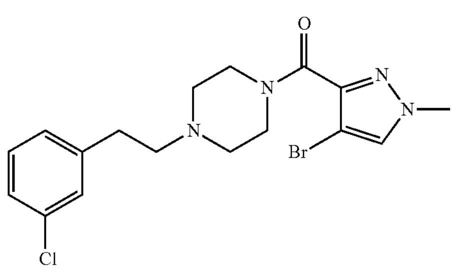 [SMILES: Cn1cc(Br)c(C(=O)N2CCN(CCc3cccc(Cl)c3)CC2)n1] | (4-Bromo-1-methyl-1H-pyrazol-3-yl)-{4-[2-(3-chloro-phenyl)-ethyl]-piperazin-1-yl}-methanone |
| 61 | 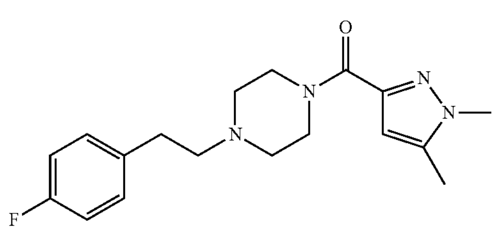 [SMILES: Cc1cc(C(=O)N2CCN(CCc3ccc(F)cc3)CC2)nn1C] | (1,5-Dimethyl-1H-pyrazol-3-yl)-{4-[2-(4-fluoro-phenyl)-ethyl]-piperazin-1-yl}-methanone |

TABLE A-continued

| Cmpd No. | Chemical Structure | Chemical Name |
|---|---|---|
| 62 | 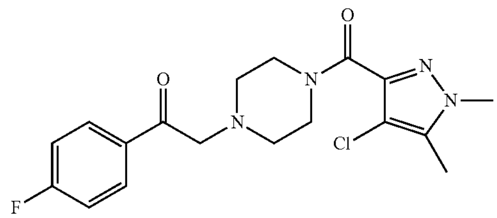 [SMILES: Cc1c(Cl)c(C(=O)N2CCN(CC(=O)c3ccc(F)cc3)CC2)nn1C] | 2-[4-(4-Chloro-1,5-dimethyl-1H-pyrazole-3-carbonyl)-piperazin-1-yl]-1-(4-fluoro-phenyl)-ethanone |
| 63 | 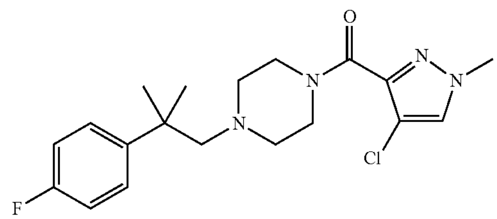 [SMILES: Cn1cc(Cl)c(C(=O)N2CCN(CC(C)(C)c3ccc(F)cc3)CC2)n1] | (4-Chloro-1-methyl-1H-pyrazol-3-yl)-{4-[2-(4-fluoro-phenyl)-2-methyl-propyl]-piperazin-1-yl}-methanone |
| 64 | 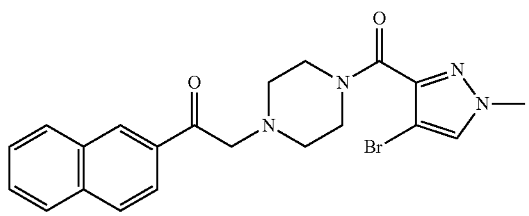 [SMILES: Cn1cc(Br)c(C(=O)N2CCN(CC(=O)c3ccc4ccccc4c3)CC2)n1] | 2-[4-(4-Bromo-1-methyl-1H-pyrazole-3-carbonyl)-piperazin-1-yl]-1-naphthalen-2-yl-ethanone |
| 65 | 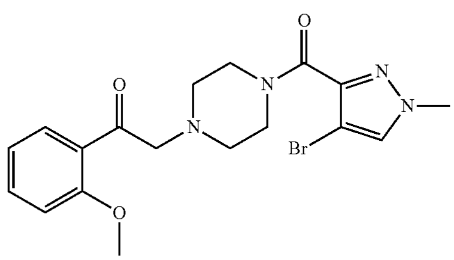 [SMILES: COc1ccccc1C(=O)CN1CCN(C(=O)c2nn(C)cc2Br)CC1] | 2-[4-(4-Bromo-1-methyl-1H-pyrazole-3-carbonyl)-piperazin-1-yl]-1-(2-methoxy-phenyl)-ethanone |
| 66 | 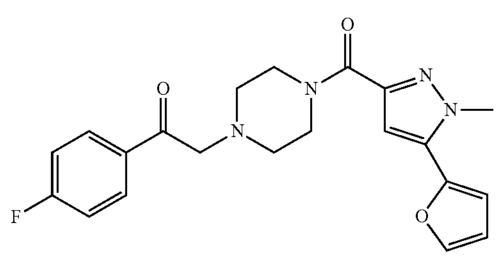 [SMILES: Cn1nc(C(=O)N2CCN(CC(=O)c3ccc(F)cc3)CC2)cc1-c1ccco1] | 1-(4-Fluoro-phenyl)-2-[4-(5-furan-2-yl-1-methyl-1H-pyrazole-3-carbonyl)-piperazin-1-yl]-ethanone |
| 67 | 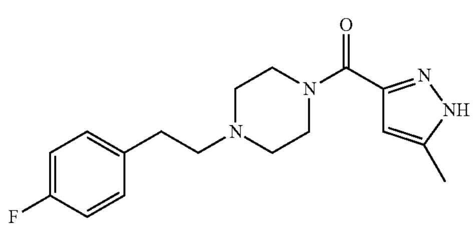 [SMILES: Cc1cc(C(=O)N2CCN(CCc3ccc(F)cc3)CC2)n[nH]1] | {4-[2-(4-Fluoro-phenyl)-ethyl]-piperazin-1-yl}-(5-methyl-1H-pyrazol-3-yl)-methanone |

TABLE A-continued

| Cmpd No. | Chemical Structure | Chemical Name |
|---|---|---|
| 68 | 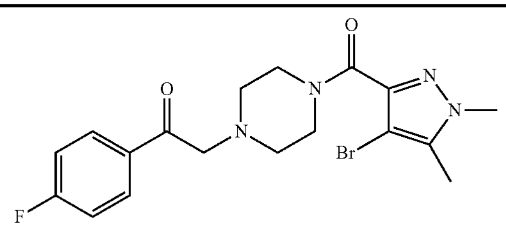 | 2-[4-(4-Bromo-1,5-dimethyl-1H-pyrazole-3-carbonyl)-piperazin-1-yl]-1-(4-fluoro-phenyl)-ethanone |
| 69 | 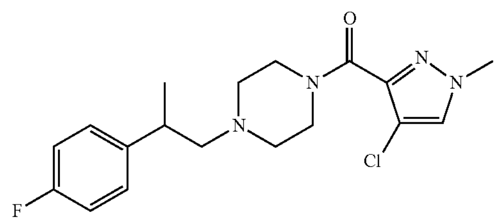 [SMILES: CC(CN1CCN(C(=O)c2nn(C)cc2Cl)CC1)c1ccc(F)cc1] | (4-Chloro-1-methyl-1H-pyrazol-3-yl)-{4-[2-(4-fluoro-phenyl)-propyl]-piperazin-1-yl}-methanone |
| 70 | 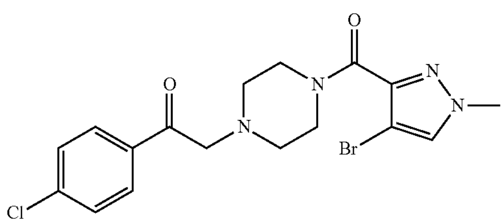 [SMILES: Cn1cc(Br)c(C(=O)N2CCN(CC(=O)c3ccc(Cl)cc3)CC2)n1] | 2-[4-(4-Bromo-1-methyl-1H-pyrazole-3-carbonyl)-piperazin-1-yl]-1-(4-chloro-phenyl)-ethanone |
| 71 | 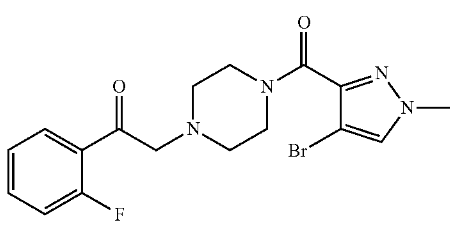 [SMILES: Cn1cc(Br)c(C(=O)N2CCN(CC(=O)c3ccccc3F)CC2)n1] | 2-[4-(4-Bromo-1-methyl-1H-pyrazole-3-carbonyl)-piperazin-1-yl]-1-(2-fluoro-phenyl)-ethanone |
| 72 | 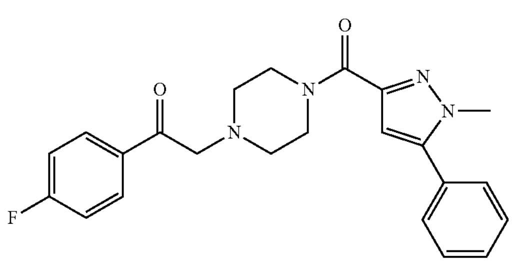 [SMILES: Cn1nc(C(=O)N2CCN(CC(=O)c3ccc(F)cc3)CC2)cc1-c1ccccc1] | 1-(4-Fluoro-phenyl)-2-[4-(1-methyl-5-phenyl-1H-pyrazole-3-carbonyl)-piperazin-1-yl]-ethanone |
| 73 | 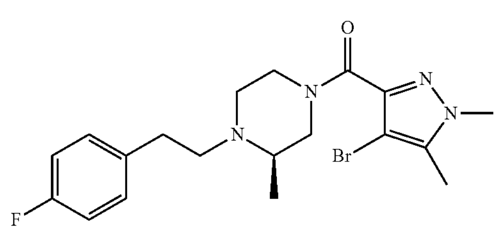 [SMILES: Cc1c(Br)c(C(=O)N2CCN(CCc3ccc(F)cc3)[C@H](C)C2)nn1C] | (4-Bromo-1,5-dimethyl-1H-pyrazol-3-yl)-{(R)-2-[2-(4-fluoro-phenyl)-ethyl]-3-methyl-piperazin-1-yl}-methanone |
| 74 | 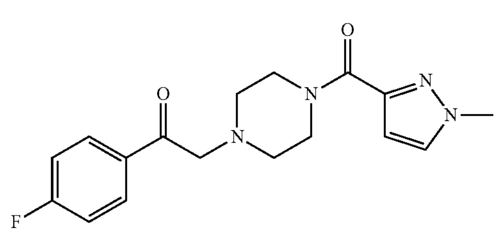 [SMILES: Cn1ccc(C(=O)N2CCN(CC(=O)c3ccc(F)cc3)CC2)n1] | 1-(4-Fluoro-phenyl)-2-[4-(1-methyl-1H-pyrazole-3-carbonyl)-piperazin-1-yl]-ethanone |

TABLE A-continued

| Cmpd No. | Chemical Structure | Chemical Name |
|---|---|---|
| 75 | 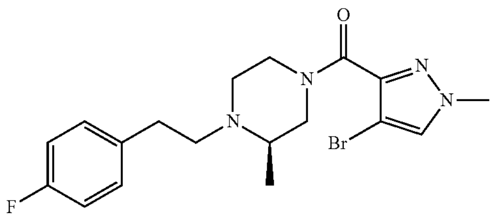 [SMILES: C[C@@H]1CN(C(=O)c2nn(C)cc2Br)CCN1CCc1ccc(F)cc1] | (4-Bromo-1-methyl-1H-pyrazol-3-yl)-{(R)-4-[2-(4-fluoro-phenyl)-ethyl]-3-methyl-piperazin-1-yl}-methanone |
| 76 | 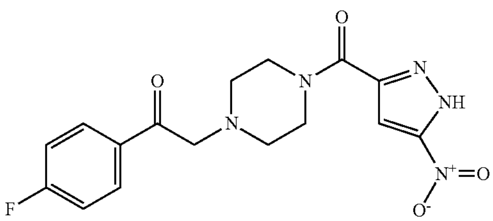 [SMILES: O=C(CN1CCN(C(=O)c2cc([N+](=O)[O-])[nH]n2)CC1)c1ccc(F)cc1] | 1-(4-Fluoro-phenyl)-2-[4-(5-nitro-1H-pyrazole-3-carbonyl)-piperazin-1-yl]-ethanone |
| 77 | 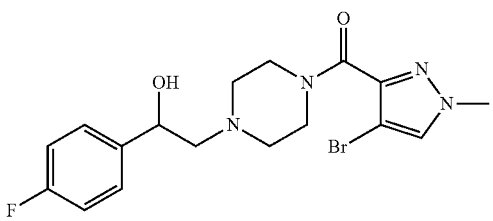 [SMILES: Cn1cc(Br)c(C(=O)N2CCN(CC(O)c3ccc(F)cc3)CC2)n1] | (4-Bromo-1-methyl-1H-pyrazol-3-yl)-{4-[2-(4-fluoro-phenyl)-2-hydroxy-ethyl]-piperazin-1-yl}-methanone |
| 78 | 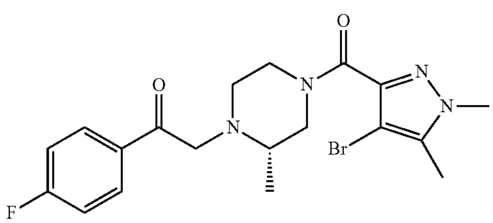 [SMILES: Cc1c(Br)c(C(=O)N2CCN(CC(=O)c3ccc(F)cc3)[C@@H](C)C2)nn1C] | 2-[(S)-4-(4-Bromo-1,5-dimethyl-1H-pyrazole-3-carbonyl)-2-methyl-piperazin-1-yl]-1-(4-fluoro-phenyl)-ethanone |
| 79 | 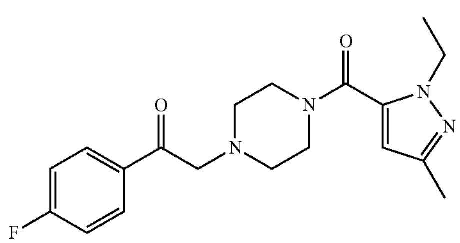 [SMILES: CCn1nc(C)cc1C(=O)N1CCN(CC(=O)c2ccc(F)cc2)CC1] | 2-[4-(2-Ethyl-5-methyl-2H-pyrazole-3-carbonyl)-piperazin-1-yl]-1-(4-fluoro-phenyl)-ethanone |
| 80 | 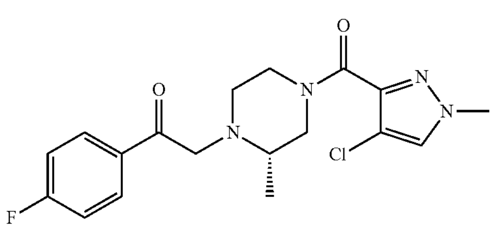 [SMILES: C[C@H]1CN(C(=O)c2nn(C)cc2Cl)CCN1CC(=O)c1ccc(F)cc1] | 2-[(S)-4-(4-Chloro-1-methyl-1H-pyrazole-3-carbonyl)-2-methyl-piperazin-1-yl]-1-(4-fluoro-phenyl)-ethanone |
| 81 | 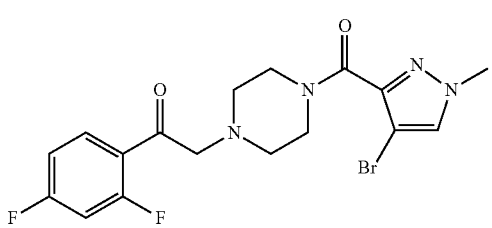 [SMILES: Cn1cc(Br)c(C(=O)N2CCN(CC(=O)c3ccc(F)cc3F)CC2)n1] | 2-[4-(4-Bromo-1-methyl-1H-pyrazole-3-carbonyl)-piperazin-1-yl]-1-(2,4-difluoro-phenyl)-ethanone |

TABLE A-continued

| Cmpd No. | Chemical Structure | Chemical Name |
|---|---|---|
| 82 | 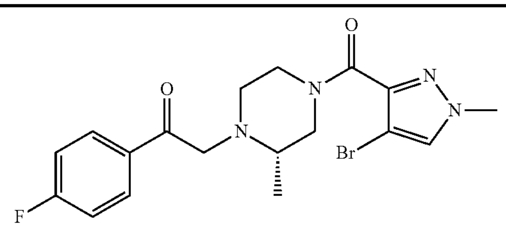 | 2-[(S)-4-(4-Bromo-1-methyl-1H-pyrazole-3-carbonyl)-2-methyl-piperazin-1-yl]-1-(4-fluoro-phenyl)-ethanone |
| 83 | 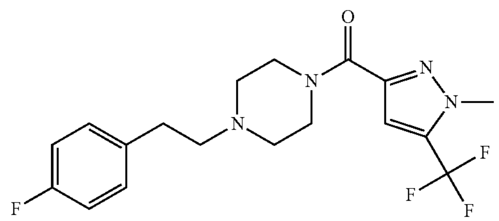 [SMILES: Cn1nc(C(=O)N2CCN(CCc3ccc(F)cc3)CC2)cc1C(F)(F)F] | {4-[2-(4-Fluoro-phenyl)-ethyl]-piperazin-1-yl}-(1-methyl-5-trifluoromethyl-1H-pyrazol-3-yl)-methanone |
| 84 | 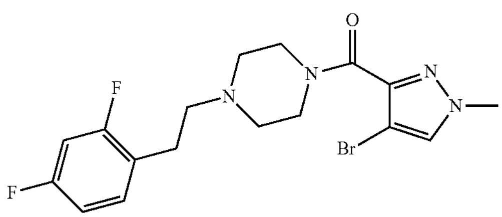 [SMILES: Cn1cc(Br)c(C(=O)N2CCN(CCc3ccc(F)cc3F)CC2)n1] | (4-Bromo-1-methyl-1H-pyrazol-3-yl)-{4-[2-(2,4-difluoro-phenyl)-ethyl]-piperazin-1-yl}-methanone |
| 85 | 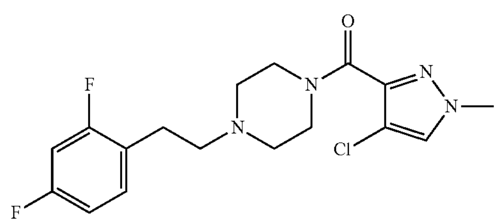 [SMILES: Cn1cc(Cl)c(C(=O)N2CCN(CCc3ccc(F)cc3F)CC2)n1] | (4-Chloro-1-methyl-1H-pyrazol-3-yl)-{4-[2-(2,4-difluoro-phenyl)-ethyl]-piperazin-1-yl}-methanone |

Additionally, individual compounds and chemical genera of the present invention, for example those compounds found in TABLE A including diastereomers and enantiomers thereof, encompass all pharmaceutically acceptable salts, solvates, and particularly hydrates, thereof.

The compounds of the Formula (Ia) of the present invention may be prepared according to relevant published literature procedures that are used by one skilled in the art. Exemplary reagents and procedures for these reactions appear hereinafter in the working Examples. Protection and deprotection may be carried out by procedures generally known in the art (see, for example, Greene, T. W. and Wuts, P. G. M., *Protecting Groups in Organic Synthesis*, 3$^{rd}$ Edition, 1999 [Wiley]; incorporated herein by reference in its entirety).

It is understood that the present invention embraces each diastereomer, each enantiomer and mixtures thereof of each compound and generic formulae disclosed herein just as if they were each individually disclosed with the specific stereochemical designation for each chiral carbon. Separation of the individual isomers (such as, chiral HPLC, recrystallization of diastereomeric mixtures, and the like) or selective synthesis (such as, enantiomeric selective syntheses, and the like) of the individual isomers is accomplished by application of various methods which are well known to practitioners in the art.

Indications and Methods of Treatment

In addition to the foregoing beneficial uses for the modulators of 5-HT2A serotonin receptor activity disclosed herein, the compounds disclosed herein are believed to be useful in the treatment of several additional diseases and disorders, and in the amelioration of symptoms thereof. Without limitation, these include the following:

1. Sleep Disorders

It is reported in the National Sleep Foundation's 2002 Sleep In America Poll, more than one-half of the adults surveyed (58%) report having experienced one or more symptoms of insomnia at least a few nights a week in the past year. Additionally, about three in ten (35%) say they have experienced insomnia-like symptoms every night or almost every night.

The normal sleep cycle and sleep architecture can be disrupted by a variety of organic causes as well as environmental influences. According to the International Classification of Sleep Disorders, there are over 80 recognized sleep disorders. Of these, compounds of the present invention are effective, for example, in any one or more of the following sleep disorders (ICSD—International Classification of Sleep Disorders: Diagnostic and Coding Manual. *Diagnostic Classification Steering Committee*, American Sleep Disorders Association, 1990):

A. Dyssomnias
   a. Intrinsic Sleep Disorders:
   Psychophysiological insomnia, sleep state misperception, idiopathic insomnia, obstructive sleep apnea syndrome, central sleep apnea syndrome, central alveolar hypoventilation syndrome, periodic limb movement disorder, restless leg syndrome and intrinsic sleep disorder NOS (not otherwise specified).
   b. Extrinsic Sleep Disorders:
   Inadequate sleep hygiene, environmental sleep disorder, altitude insomnia, adjustment sleep disorder, insufficient sleep syndrome, limit-setting sleep disorder, sleep onset association disorder, nocturnal eating (drinking) syndrome, hypnotic-dependent sleep disorder, stimulant-dependent sleep disorder, alcohol-dependent sleep disorder, toxin-induced sleep disorder and extrinsic sleep disorder NOS.
   c. Circadian Rhythm Sleep Disorders:
   Time zone change (jet lag) syndrome, shift work sleep disorder, irregular sleep-wake pattern, delayed sleep phase syndrome, advanced sleep phase syndrome, non-24-hour sleep-wake disorder and circadian rhythm sleep disorder NOS.
B. Parasomnias
   a. Arousal Disorders:
   Confusional arousals, sleepwalking and sleep terrors.
   b. Sleep-Wake Transition Disorders:
   Rhythmic movement disorder, sleep starts, sleep talking and nocturnal leg cramps.
C. Sleep Disorders Associated with Medical/Psychiatric Disorders
   a. Associated with Mental Disorders:
   Psychoses, mood disorders, anxiety disorders, panic disorders and alcoholism.
   b. Associated with Neurological Disorders:
   Cerebral degenerative disorders, dementia, Parkinsonism, fatal familial insomnia, sleep-related epilepsy, electrical status epilepticus of sleep and sleep-related headaches.
   c. Associated with Other Medical Disorders:
   Sleeping sickness, nocturnal cardiac ischemia, chronic obstructive pulmonary disease, sleep-related asthma, sleep-related gastroesophageal reflux, peptic ulcer disease, fibrositis syndrome, osteoarthritis, rheumatoid arthritis, fibromyalgia and post-surgical.

The effects of sleep deprivation are more than excessive daytime sleepiness. Chronic insomniacs report elevated levels of stress, anxiety, depression and medical illnesses (National Institutes of Health, National Heart, Lung, and Blood Institute, *Insomnia Facts Sheet*, October 1995). Preliminary evidence suggests that having a sleep disorder that causes significant loss of sleep may contribute to increased susceptibility to infections due to immunosuppression, cardiovascular complications such as hypertension, cardiac arrhythmias, stroke, and myocardial infarction, compromised glucose tolerance, increased obesity and metabolic syndrome. Compounds of the present invention are useful to prevent or alleviate these complications by improving sleep quality.

The most common class of medications for the majority of sleep disorders are the benzodiazepines, but the adverse effect profile of benzodiazepines include daytime sedation, diminished motor coordination, and cognitive impairments. Furthermore, the National Institutes of Health Consensus conference on Sleeping Pills and Insomnia in 1984 have developed guidelines discouraging the use of such sedative-hypnotics beyond 4-6 weeks because of concerns raised over drug misuse, dependency, withdrawal and rebound insomnia. Therefore, it is desirable to have a pharmacological agent for the treatment of insomnia, which is more effective and/or has fewer side effects than those currently used. In addition, benzodiazepines are used to induce sleep, but have little to no effect on the maintenance of sleep, sleep consolidation or slow wave sleep. Therefore, sleep maintenance disorders are not currently well treated.

Clinical studies with agents of a similar mechanism of action as are compounds of the present invention have demonstrated significant improvements on objective and subjective sleep parameters in normal, healthy volunteers as well as patients with sleep disorders and mood disorders [Sharpley A. L., et al. Slow Wave Sleep in Humans: Role of $5\text{-HT}_{2A}$ and $5\text{HT}_{2C}$ Receptors. *Neuropharmacology*, 1994, Vol. 33(3/4):467-71; Winokur A., et al. Acute Effects of Mirtazapine on Sleep Continuity and Sleep Architecture in Depressed Patients: A Pilot Study. *Soc. of Biol. Psych.*, 2000, Vol. 48:75-78; and Landolt H. P., et al. Serotonin-2 Receptors and Human Sleep: Effect of Selective Antagonist on EEG Power Spectra. *Neuropsychopharmacology*, 1999, Vol. 21(3):455-66].

Some sleep disorders are sometimes found in conjunction with other conditions and accordingly those conditions are treatable by compounds of Formula (Ia). For example, but not limited to, patients suffering from mood disorders typically suffer from a sleep disorder that can be treatable by compounds of Formula (Ia). Having one pharmacological agent which treats two or more existing or potential conditions, as does the present invention, is more cost effective, leads to better compliance and has fewer side effects than taking two or more agents.

It is an object of the present invention to provide a therapeutic agent for the use in treating sleep disorders. It is another object of the present invention to provide one pharmaceutical agent, which may be useful in treating two or more conditions wherein one of the conditions is a sleep disorder. Compounds of the present invention described herein may be used alone or in combination with a mild sleep inducer (i.e. antihistamine).

Sleep Architecture:

Sleep comprises two physiological states: Non rapid eye movement (NREM) and rapid eye movement (REM) sleep. NREM sleep consists of four stages, each of which is characterized by progressively slower brain wave patterns, with the slower patterns indicating deeper sleep. So called delta sleep, stages 3 and 4 of NREM sleep, is the deepest and most refreshing type of sleep. Many patients with sleep disorders are unable to adequately achieve the restorative sleep of stages 3 and 4. In clinical terms, patients' sleep patterns are described as fragmented, meaning the patient spends a lot of time alternating between stages 1 and 2 (semi-wakefulness) and being awake and very little time in deep sleep. As used herein, the term "fragmented sleep architecture" means an individual, such as a sleep disorder patient, spends the majority of their sleep time in NREM sleep stages 1 and 2, lighter periods of sleep from which the individual can be easily aroused to a waking state by limited external stimuli. As a result, the individual cycles through frequent bouts of light sleep interrupted by frequent awakenings throughout the sleep period. Many sleep disorders are characterized by a fragmented sleep architecture. For example, many elderly patients with sleep complaints have difficulty achieving long bouts of deep, refreshing sleep (NREM stages 3 and 4) and instead spend the majority of their sleep time in NREM sleep stages 1 and 2.

In contrast to fragmented sleep architecture, as used herein the term "sleep consolidation" means a state in which the number of NREM sleep bouts, particularly Stages 3 and 4, and the length of those sleep bouts are increased, while the number and length of waking bouts are decreased. In essence, the architecture of the sleep disorder patient is consolidated to a sleeping state with increased periods of sleep and fewer awakenings during the night and more time is spent in slow wave sleep (stages 3 and 4) with fewer oscillation stage 1 and 2 sleep. Compounds of the present invention can be effective in consolidating sleep patterns so that the patient with previously fragmented sleep can now achieve restorative, delta-wave sleep for longer, more consistent periods of time.

As sleep moves from stage 1 into later stages, heart rate and blood pressure drop, metabolic rate and glucose consumption fall, and muscles relax. In normal sleep architecture, NREM sleep makes up about 75% of total sleep time; stage 1 accounting for 5-10% of total sleep time, stage 2 for about 45-50%, stage 3 approximately 12%, and stage 4 13-15%. About 90 minutes after sleep onset, NREM sleep gives way to the first REM sleep episode of the night. REM makes up approximately 25% of total sleep time. In contrast to NREM sleep, REM sleep is characterized by high pulse, respiration, and blood pressure, as well as other physiological patterns similar to those seen in the active waking stage. Hence, REM sleep is also known as "paradoxical sleep." Sleep onset occurs during NREM sleep and takes 10-20 minutes in healthy young adults. The four stages of NREM sleep together with a REM phase form one complete sleep cycle that is repeated throughout the duration of sleep, usually four or five times. The cyclical nature of sleep is regular and reliable: a REM period occurs about every 90 minutes during the night. However, the first REM period tends to be the shortest, often lasting less than 10 minutes, whereas the later REM periods may last up to 40 minutes. With aging, the time between retiring and sleep onset increases and the total amount of night-time sleep decreases because of changes in sleep architecture that impair sleep maintenance as well as sleep quality. Both NREM (particularly stages 3 and 4) and REM sleep are reduced. However, stage 1 NREM sleep, which is the lightest sleep, increases with age.

As used herein, the term "delta power" means a measure of the duration of EEG activity in the 0.5 to 3.5 Hz range during NREM sleep and is thought to be a measure of deeper, more refreshing sleep. Delta power is hypothesized to be a measure of a theoretical process called Process S and is thought to be inversely related to the amount of sleep an individual experiences during a given sleep period. Sleep is controlled by homeostatic mechanisms; therefore, the less one sleeps the greater the drive to sleep. It is believed that Process S builds throughout the wake period and is discharged most efficiently during delta power sleep. Delta power is a measure of the magnitude of Process S prior to the sleep period. The longer one stays awake, the greater Process S or drive to sleep and thus the greater the delta power during NREM sleep. However, individuals with sleep disorders have difficulty achieving and maintaining delta wave sleep, and thus have a large build-up of Process S with limited ability to discharge this buildup during sleep. $5\text{-}HT_{2A}$ agonists tested preclinically and clinically mimic the effect of sleep deprivation on delta power, suggesting that subjects with sleep disorders treated with a $5\text{-}HT_{2A}$ inverse agonist or antagonist will be able to achieve deeper sleep that is more refreshing. These same effects have not been observed with currently marketed pharmacotherapies. In addition, currently marketed pharmacotherapies for sleep have side effects such as hangover effects or addiction that are associated with the GABA receptor. $5\text{-}HT_{2A}$ inverse agonists do not target the GABA receptor and so these side effects are not a concern.

Subjective and Objective Determinations of Sleep Disorders:

There are a number of ways to determine whether the onset, duration or quality of sleep (e.g. non-restorative or restorative sleep) is impaired or improved. One method is a subjective determination of the patient, e.g., do they feel drowsy or rested upon waking. Other methods involve the observation of the patient by another during sleep, e.g., how long it takes the patient to fall asleep, how many times the patient wakes up during the night, how restless is the patient during sleep, etc. Another method is to measure the stages of sleep objectively using polysomnography.

Polysomnography is the monitoring of multiple electrophysiological parameters during sleep and generally includes measurement of EEG activity, electroculographic activity and electromyographic activity, as well as other measurements. These results, along with observations, can measure not only sleep latency (the amount of time required to fall asleep), but also sleep continuity (overall balance of sleep and wakefulness) and sleep consolidation (percent of sleeping time spent in delta-wave or restorative sleep) which may be an indication of the quality of sleep.

There are five distinct sleep stages, which can be measured by polysomnography: rapid eye movement (REM) sleep and four stages of non-rapid eye movement (NREM) sleep (stages 1, 2, 3 and 4). Stage 1 NREM sleep is a transition from wakefulness to sleep and occupies about 5% of time spent asleep in healthy adults. Stage 2 NREM sleep, which is characterized by specific EEG waveforms (sleep spindles and K complexes), occupies about 50% of time spent asleep. Stages 3 and 4 NREM sleep (also known collectively as slow-wave sleep and delta-wave sleep) are the deepest levels of sleep and occupy about 10-20% of sleep time. REM sleep, during which the majority of vivid dreams occur, occupies about 20-25% of total sleep.

These sleep stages have a characteristic temporal organization across the night. NREM stages 3 and 4 tend to occur in the first one-third to one-half of the night and increase in duration in response to sleep deprivation. REM sleep occurs cyclically through the night. Alternating with NREM sleep about every 80-100 minutes. REM sleep periods increase in duration toward the morning. Human sleep also varies characteristically across the life span. After relative stability with large amounts of slow-wave sleep in childhood and early adolescence, sleep continuity and depth deteriorate across the adult age range. This deterioration is reflected by increased wakefulness and stage 1 sleep and decreased stages 3 and 4 sleep.

In addition, the compounds of the invention can be useful for the treatment of the sleep disorders characterized by excessive daytime sleepiness such as narcolepsy. Inverse agonists at the serotonin $5\text{-}HT_{2A}$ receptor improve the quality of sleep at nighttime which can decrease excessive daytime sleepiness.

Accordingly, another aspect of the present invention relates to the therapeutic use of compounds of the present invention for the treatment of sleep disorders. Compounds of the present invention are potent inverse agonists at the serotonin $5\text{-}HT_{2A}$ receptor and can be effective in the treatment of sleep disorders by promoting one or more of the following: reducing the sleep onset latency period (measure of sleep induction), reducing the number of nighttime awakenings, and prolonging the amount of time in delta-wave sleep (measure of sleep quality enhancement and sleep consolidation) without effecting REM sleep. In addition, compounds of the present invention can be effective either as a monotherapy or in combination with sleep inducing agents, for example but not limited to, antihistamines.

Pharmacodynamic Effects of the Selective 5-HT$_{2A}$ Inverse Agonist APD125 in Healthy Adults:

APD125, a potent and selective 5-HT$_{2A}$ serotonin receptor inverse agonist is a member of the genus disclosed in the European Patent EP1558582. In Phase 1 trials, APD125 showed vigilance-lowering effects on waking EEG, with maximal effects at 40-80 mg; peak effects were observed at 2-4 h after dosing. In the afternoon nap model of insomnia in normal volunteers, APD125 increased slow wave sleep and associated parameters in a dose-dependent manner, primarily during the early part of sleep. These effects occurred at the expense of REM sleep. Sleep onset latency was not decreased by APD125. In the afternoon nap model, APD125 decreased microarousals, the number of sleep stage shifts, and number of awakenings after sleep onset.

In conclusion, APD125, a 5-HT$_{2A}$ serotonin receptor inverse agonist, improved parameters of sleep consolidation and maintenance in humans. Thus, compounds of the present invention, also highly selective 5-HT$_{2A}$ serotonin receptor inverse agonists, will offer similar improvements in sleep parameters.

2. Antiplatelet Therapies (Conditions Related to Platelet Aggregation):

Antiplatelet agents (antiplatelets) are prescribed for a variety of conditions. For example, in coronary artery disease they are used to help prevent myocardial infarction or stroke in patients who are at risk of developing obstructive blood clots (e.g., coronary thrombosis).

In a myocardial infarction (heart attack), the heart muscle does not receive enough oxygen-rich blood because of a blockage in the coronary blood vessels. If taken while an attack is in progress or immediately afterward (preferably within 30 minutes), antiplatelets can reduce the damage to the heart.

A transient ischemic attack ("TIA" or "mini-stroke") is a brief interruption of oxygen flow to the brain due to decreased blood flow through arteries, usually due to an obstructing blood clot. Antiplatelet drugs have been found to be effective in preventing TIAs.

Angina is a temporary and often recurring chest pain, pressure or discomfort caused by inadequate oxygen-rich blood flow (ischemia) to some parts of the heart. In patients with angina, antiplatelet therapy can reduce the effects of angina and the risk of myocardial infarction.

Stroke is an event in which the brain does not receive enough oxygen-rich blood, usually due to blockage of a cerebral blood vessel by a blood clot. In high-risk patients, taking antiplatelets regularly has been found to prevent the formation of blood clots that cause first or second strokes.

Angioplasty is a catheter-based technique used to open arteries obstructed by a blood clot. Whether or not stenting is performed immediately after this procedure to keep the artery open, antiplatelets can reduce the risk of forming additional blood clots following the procedure(s).

Coronary bypass surgery is a surgical procedure in which an artery or vein is taken from elsewhere in the body and grafted to a blocked coronary artery, rerouting blood around the blockage and through the newly attached vessel. After the procedure, antiplatelets can reduce the risk of secondary blood clots.

Atrial fibrillation is the most common type of sustained irregular heart rhythm (arrhythmia). Atrial fibrillation affects about two million Americans every year. In atrial fibrillation, the atria (the heart's upper chambers) rapidly fire electrical signals that cause them to quiver rather than contract normally. The result is an abnormally fast and highly irregular heartbeat. When given after an episode of atrial fibrillation, antiplatelets can reduce the risk of blood clots forming in the heart and traveling to the brain (embolism).

5-HT$_{2A}$ serotonin receptors are expressed on smooth muscle of blood vessels and 5-HT secreted by activated platelets causes vasoconstriction as well as activation of additional platelets during clotting. There is evidence that a 5-HT$_{2A}$ inverse agonist will inhibit platelet aggregation and thus be a potential treatment as an antiplatelet therapy (see Satimura, K., et al., *Clin. Cardiol.* 2002 Jan. 25 (1):28-32; and Wilson, H. C. et al., *Thromb. Haemost.* 1991 Sep. 2; 66(3):355-60).

5-HT$_{2A}$ inverse agonists can be used to treat, for example, claudication or peripheral artery disease as well as cardiovascular complications (see *Br. Med. J.* 298: 424-430, 1989), arterial thrombosis (see, Pawlak, D. et al. *Thrombosis Research* 90: 259-270, 1998), atherosclerosis (see, Hayashi, T. et al. Atherosclerosis 168: 23-31, 2003), vasoconstriction caused by serotonin (see, Fujiwara, T. and Chiba, S. *Journal of Cardiovascular Pharmacology* 26: 503-510, 1995), restenosis of arteries following angioplasty or stent placement (see, Fujita, M. et al. *Am. Heart J.* 145:e16, 2003). It can also be used alone or in combination with thrombolytic therapy, for example, tissue plasminogen activator (tPA) (see, Yamashita, T. et al. *Haemostasis* 30:321-332, 2000), to provide cardioprotection following MI or postischemic myocardial dysfunction (see, Muto, T. et al. *Mol. Cell. Biochem.* 272: 119-132, 2005) or protection from ischemic injury during percutaneous coronary intervention (see, Horibe, E. *Circulation Research* 68: 68-72, 2004), and the like, including complications resulting therefrom.

5-HT$_{2A}$ inverse antagonists can increase circulating adiponectin in patients, suggesting that they would also be useful in protecting patients against indications that are linked to adiponectin, for example, myocardial ischemia reperfusion injury and atherosclerosis (see Nomura et al. *Blood Coagulation and Fibrinolysis* 2005, 16, 423-428).

The 5-HT$_{2A}$ inverse agonists disclosed herein provide beneficial improvement in microcirculation to patients in need of antiplatelet therapy by antagonizing the vasoconstrictive products of the aggregating platelets in, for example and not limited to the indications described above. Accordingly, in some embodiments, the present invention provides methods for reducing platelet aggregation in a patient in need thereof comprising administering to the patient a composition comprising a 5-HT$_{2A}$ inverse agonist disclosed herein. In further embodiments, the present invention provides methods for treating coronary artery disease, myocardial infarction, transient ischemic attack, angina, stroke, atrial fibrillation, or a symptom of any of the foregoing in a patient in need of the treatment, comprising administering to the patient a composition comprising a 5-HT$_{2A}$ inverse agonist disclosed herein.

In further embodiments, the present invention provides methods for reducing risk of blood clot formation in an angioplasty or coronary bypass surgery patient, or a patient suffering from atrial fibrillation, comprising administering to the patient a composition comprising a 5-HT$_{2A}$ inverse agonist disclosed herein at a time where such risk exists.

3. Asthma

5-HT (5-hydroxytryptamine) has been linked to the pathophysiology of acute asthma (see Cazzola, M. and Matera, M. G., *Trends Pharmacol. Sci.* 21: 201-202, 2000; and De Bie, J. J. et al., *British J. Pharm.,* 1998, 124, 857-864). The compounds of the present invention disclosed herein are useful in the treatment of asthma, and the treatment of the symptoms thereof. Accordingly, in some embodiments, the present invention provides methods for treating asthma in a patient in need of the treatment, comprising administering to the patient a composition comprising a 5-HT$_{2A}$ inverse agonist disclosed herein. In further embodiments, methods are provided for treating a symptom of asthma in a patient in need of the treatment, comprising administering to the patient a composition comprising a 5-HT$_{2A}$ inverse agonist disclosed herein.

4. Agitation

Agitation is a well-recognized behavioral syndrome with a range of symptoms, including hostility, extreme excitement, poor impulse control, tension and uncooperativeness (See Cohen-Mansfield J., and Billig, N., (1986), Agitated Behaviors in the Elderly. I. A Conceptual Review. *J. Am. Geriatr. Soc.* 34(10): 711-721).

Agitation is a common occurrence in the elderly and is often associated with dementia such as those caused by Alzheimer's disease, Lewy Body, Parkinson's, and Huntington's, which are degenerative diseases of the nervous system. Diseases that affect blood vessels, such as stroke, or multi-infarct dementia, which is caused by multiple strokes in the brain can also induce agitation. Alzheimer's disease accounts for approximately 50 to 70% of all dementias (See Koss E., et al., (1997), Assessing patterns of agitation in Alzheimer's disease patients with the Cohen-Mansfield Agitation Inventory. The Alzheimer's Disease Cooperative Study. *Alzheimer Dis. Assoc. Disord.* 11(suppl 2):S45-S50).

An estimated 5% of people aged 65 and older and up to 20% of those aged 80 and older are affected by dementia; of these sufferers, nearly half exhibit behavioral disturbances, such as agitation, wandering and violent outbursts.

Agitated behaviors can also be manifested in cognitively intact elderly people and by those with psychiatric disorders other than dementia.

Agitation is often treated with antipsychotic medications such as haloperidol in nursing home and other assisted care settings. There is emerging evidence that agents acting at the 5-HT$_{2A}$ serotonin receptors in the brain have the effects of reducing agitation in patients, including Alzheimer's dementia (See Katz, I. R., et al., *J. Clin. Psychiatry* 1999 February, 60(2): 107-115; and Street, J. S., et al., *Arch. Gen. Psychiatry* 2000 October, 57(10):968-976).

The compounds of the invention disclosed herein are useful for treating agitation and symptoms thereof. Thus, in some embodiments, the present invention provides methods for treating agitation in a patient in need of such treatment comprising administering to the patient a composition comprising a 5-HT$_{2A}$ inverse agonist disclosed herein. In some embodiments, the agitation is due to a psychiatric disorder other than dementia. In some embodiments, the present invention provides methods for treatment of agitation or a symptom thereof in a patient suffering from dementia comprising administering to the patient a composition comprising a 5-HT$_{2A}$ inverse agonist disclosed herein. In some embodiments of such methods, the dementia is due to a degenerative disease of the nervous system, for example and without limitation, Alzheimer's disease, Lewy Body, Parkinson's disease, and Huntington's disease, or dementia due to diseases that affect blood vessels, including, without limitation, stroke and multi-infarct dementia. In some embodiments, methods are provided for treating agitation or a symptom thereof in a patient in need of such treatment, where the patient is a cognitively intact elderly patient, comprising administering to the patient a composition comprising a 5-HT$_{2A}$ inverse agonist disclosed herein.

5. Add-on Therapy to Haloperidol in the Treatment of Schizophrenia and Other Disorders:

Schizophrenia is a psychopathic disorder of unknown origin, which usually appears for the first time in early adulthood and is marked by a number of characteristics, psychotic symptoms, progression, phasic development and deterioration in social behavior and professional capability in the region below the highest level ever attained. Characteristic psychotic symptoms are disorders of thought content (multiple, fragmentary, incoherent, implausible or simply delusional contents or ideas of persecution) and of mentality (loss of association, flight of imagination, incoherence up to incomprehensibility), as well as disorders of perceptibility (hallucinations), of emotions (superficial or inadequate emotions), of self-perception, of intentions and impulses, of interhuman relationships, and finally psychomotoric disorders (such as catatonia). Other symptoms are also associated with this disorder: see, *American Statistical and Diagnostic Handbook*.

Haloperidol (Haldol) is a potent dopamine D$_2$ receptor antagonist. It is widely prescribed for acute schizophrenic symptoms, and is very effective for the positive symptoms of schizophrenia. However, Haldol is not effective for the negative symptoms of schizophrenia and may actually induce negative symptoms as well as cognitive dysfunction. In accordance with some methods of the invention, adding a 5-HT$_{2A}$ inverse agonist concomitantly with Haldol will provide benefits including the ability to use a lower dose of Haldol without losing its effects on positive symptoms, while reducing or eliminating its inductive effects on negative symptoms, and prolonging relapse to the patient's next schizophrenic event.

Haloperidol is used for treatment of a variety of behavioral disorders, drug induced psychosis, excitative psychosis, Gilles de la Tourette's syndrome, manic disorders, psychosis (organic and NOS), psychotic disorder, psychosis, schizophrenia (acute, chronic and NOS). Further uses include in the treatment of infantile autism, Huntington's chorea, and nausea and vomiting from chemotherapy and chemotherapeutic antibodies. Administration of 5-HT$_{2A}$ inverse agonists disclosed herein with haloperidol also will provide benefits in these indications.

In some embodiments, the present invention provides methods for treating a behavioral disorder, drug induced psychosis, excitative psychosis, Gilles de la Tourette's syndrome, manic disorders, psychosis (organic and NOS), psychotic disorder, psychosis, schizophrenia (acute, chronic and NOS) comprising administering to the patient a dopamine D$_2$ receptor antagonist and a 5-HT$_{2A}$ inverse agonist disclosed herein.

In some embodiments, the present invention provides methods for treating a behavioral disorder, drug induced psychosis, excitative psychosis, Gilles de la Tourette's syndrome, manic disorders, psychosis (organic and NOS), psychotic disorder, psychosis, schizophrenia (acute, chronic and NOS) comprising administering to the patient haloperidol and a 5-HT$_{2A}$ inverse agonist disclosed herein.

In some embodiments, the present invention provides methods for treating infantile autism, Huntington's chorea, or nausea and vomiting from chemotherapy or chemotherapeutic antibodies comprising administering to the patient a dopamine D$_2$ receptor antagonist and a 5-HT$_{2A}$ inverse agonist disclosed herein.

In some embodiments, the present invention provides methods for treating infantile autism, Huntington's chorea, or nausea and vomiting from chemotherapy or chemotherapeutic antibodies comprising administering to the patient haloperidol and a 5-HT$_{2A}$ inverse agonist disclosed herein.

In further embodiments, the present invention provides methods for treating schizophrenia in a patient in need of the treatment comprising administering to the patient a dopamine D$_2$ receptor antagonist and a 5-HT$_{2A}$ inverse agonist disclosed herein. Preferably, the dopamine D$_2$ receptor antagonist is haloperidol.

The administration of the dopamine D$_2$ receptor antagonist can be concomitant with administration of the 5-HT$_{2A}$ inverse agonist, or they can be administered at different times. Those of skill in the art will easily be able to determine appropriate dosing regimes for the most efficacious reduction or elimination of deleterious haloperidol effects. In some embodiments, haloperidol and the 5-HT$_{2A}$ inverse agonist are administered in a single dosage form, and in other embodiments, they are administered in separate dosage forms.

The present invention further provides methods of alleviating negative symptoms of schizophrenia induced by the administration of haloperidol to a patient suffering from schizophrenia, comprising administering to the patient a 5-HT$_{2A}$ inverse agonist as disclosed herein.

6. Diabetic-Related Pathologies:

Although hyperglycemia is the major cause for the pathogenesis of diabetic complications such as diabetic peripheral neuropathy (DPN), diabetic nephropathy (DN) and diabetic retinopathy (DR), increased plasma serotonin concentration in diabetic patients has also been implicated to play a role in disease progression (Pietraszek, M. H., et al. *Thrombosis Res.* 1992, 66(6), 765-74; and Andrzejewska-Buczko J., et al., *Klin. Oczna.* 1996; 98(2), 101-4). Serotonin is believed to play a role in vasospasm and increased platelet aggregability. Improving microvascular blood flow is beneficial to diabetic complications.

A recent study by Cameron and Cotter in *Naunyn Schmiedebergs Arch. Pharmacol.* 2003 June; 367(6):607-14, used a 5-HT$_{2A}$ antagonist experimental drug AT-1015, and other nonspecific 5-HT$_{2A}$ antagonists including ritanserin and sarpogrelate. These studies found that all three drugs were able to produce a marked correction (82.6-99.7%) of a 19.8% sciatic motor conduction deficit in diabetic rats. Similarly, 44.7% and 14.9% reductions in sciatic endoneurial blood flow and saphenous sensory conduction velocity were completely reversed.

In a separate patient study, sarpogrelate was evaluated for the prevention of the development or progression of diabetic nephropathy (Takahashi, T., et al., *Diabetes. Res. Clin. Pract.* 2002 November; 58(2):123-9). In the trial of 24 months of treatment, sarpogrelate significantly reduced urinary albumin excretion level.

7. Glaucoma

Topical ocular administration of 5-HT$_2$ receptor antagonists result in a decrease in intra ocular pressure (IOP) in monkeys (Chang et al., *J. Ocul. Pharmacol.* 1:137-147 (1985)) and humans (Mastropasqua et al., *Acta. Ophthalmol. Scand. Suppl.* 224:24-25 (1997)) indicating utility for similar compounds such as 5-HT$_{2A}$ inverse agonists in the treatment of ocular hypertension associated with glaucoma. The 5-HT$_2$ receptor antagonist ketanserin (Mastropasqua supra) and sarpogrelate (Takenaka et al., *Investig. Ophthalmol. Vis. Sci.* 36:S734 (1995)) have been shown to significantly lower IOP in glaucoma patients.

8. Progressive Multifocal Leukoencephalopathy

Progressive multifocal leukoencephalopathy (PML) is a lethal demyelinating disease caused by an opportunistic viral infection of oligodendrocytes in immunocompromised patients. The causative agent is JC virus, a ubiquitous papovavirus that infects the majority of the population before adulthood and establishes a latent infection in the kidney. In immunocompromised hosts, the virus can reactivate and productively infect oligodendrocytes. This previously rare condition, until 1984 reported primarily in persons with underlying lymphoproliferative disorders, is now more common because it occurs in 4% of patients with AIDS. Patients usually present with relentlessly progressive focal neurologic defects, such as hemiparesis or visual field deficits, or with alterations in mental status. On brain MRI, one or more white matter lesions are present; they are hyperintense on T2-weighted images and hypointense on T1-weighted images. There is no mass effect, and contrast enhancement is rare. Diagnosis can be confirmed by brain biopsy, with demonstration of virus by in situ hybridization or immunocytochemistry. Polymerase chain reaction amplification of JC virus sequences from the CSF can confirm diagnosis without the need for biopsy [Antinori et al., *Neurology* (1997) 48:687-694; Berger and Major, *Seminars in Neurology* (1999) 19:193-200; and Portegies, et al., *Eur. J. Neurol.* (2004) 11:297-304]. Currently, there is no effective therapy. Survival after diagnosis is about 3 to 5 months in AIDS patients.

JC virus enters cells by receptor-mediated clathrin-dependent endocytosis. Binding of JC virus to human glial cells (e.g., oligodendrocytes) induces an intracellular signal that is critical for entry and infection by a ligand-inducible clathrin-dependent mechanism [Querbes et al., *J. Virology* (2004) 78:250-256]. Recently, 5-HT$_{2A}$ was shown to be the receptor on human glial cells mediating infectious entry of JC virus by clathrin-dependent endocytosis [Elphick et al., *Science* (2004) 306:1380-1383]. 5-HT$_{2A}$ antagonists, including ketanserin and ritanserin, inhibited JC virus infection of human glial cells. Ketanserin and ritanserin have inverse agonist activity at 5-HT$_{2A}$.

5-HT$_{2A}$ antagonists including inverse agonists have been contemplated to be useful in the treatment of PML [Elphick et al., *Science* (2004) 306:1380-1383]. Prophylactic treatment of HIV-infected patients with 5-HT$_{2A}$ antagonists is envisioned to prevent the spread of JC virus to the central nervous system and the development of PML. Aggressive therapeutic treatment of patients with PML is envisioned to reduce viral spread within the central nervous system and prevent additional episodes of demyelination.

One aspect of the present invention encompasses methods for the treatment of progressive multifocal leukoencephalopathy in an individual comprising administering to the individual in need thereof a therapeutically effective amount of a compound according to any of the embodiments described herein or a pharmaceutical composition.

In some embodiments, the individual in need thereof has a lymphoproliferative disorder. In some embodiments, the lymphoproliferative disorder is leukemia or lymphoma. In some embodiments, the leukemia or lymphoma is chronic lymphocytic leukemia, Hodgkin's disease, or the like.

In some embodiments, the individual in need thereof has a myeloproliferative disorder.

In some embodiments, the individual in need thereof has carcinomatosis.

In some embodiments, the individual in need thereof has a granulomatous or inflammatory disease. In some embodiments, the granulomatous or inflammatory disease is tuberculosis or sarcoidosis.

In some embodiments, the individual in need thereof is immunocompromised. In some embodiments, the immunocompromised individual has impaired cellular immunity. In some embodiments, the impaired cellular immunity comprises impaired T-cell immunity.

In some embodiments, the individual in need thereof is infected with HIV. In some embodiments, the HIV-infected individual has a CD4+ cell count of ≤200/mm³. In some embodiments, the HIV-infected individual has AIDS. In some embodiments, the HIV-infected individual has AIDS-related complex (ARC). In certain embodiments, ARC is defined as the presence of two successive CD4+ cell counts below 200/mm³ and at least two of the following signs or symptoms: oral hairy leukoplakia, recurrent oral candidiasis, weight loss of at least 15 lb or 10% of body weight within last six months, multidermatomal herpes zoster, temperature above 38.5° C. for more than 14 consecutive days or more than 15 days in a 30-day period, or diarrhea with more than three liquid stools per day for at least 30 days [see, e.g., Yamada et al., *Clin. Diagn. Virol.* (1993) 1:245-256].

In some embodiments, the individual in need thereof is undergoing immunosuppressive therapy. In some embodiments, the immunosuppressive therapy comprises administering an immunosuppressive agent [see, e.g., Mueller, *Ann. Thorac. Surg.* (2004) 77:354-362; and Krieger and Emre, *Pediatr. Transplantation* (2004) 8:594-599]. In some embodiments, the immunosuppressive therapy comprises administering an immunosuppressive agent selected from the group consisting of: corticosteroids (for example, prednisone and the like), calcineurin inhibitors (for example, cyclosporine, tacrolimus, and the like), antiproliferative agents (for example, azathioprine, mycophenolate mofetil, sirolimus, everolimus, and the like), T-cell depleting agents (for example, OKT®3 monoclonal antibody (mAb), anti-CD3 immunotoxin FN18-CRM9, Campath-1H (anti-CD52) mAb, anti-CD4 mAb, anti-T cell receptor mAb, and the like), anti-IL-2 receptor (CD25) mAb (for example, basiliximab, daclizumab, and the like), inhibitors of co-stimulation (for example, CTLA4-Ig, anti-CD154 (CD40 ligand) mAb, and the like), deoxyspergualin and analogs thereof (for example, 15-DSG, LF-08-0299, LF14-0195, and the like), leflunomide and analogs thereof (for example, leflunomide, FK778, FK779, and the like), FTY720, anti-alpha-4-integrin monoclonal antibody, and anti-CD45 RB monoclonal antibody. In some embodiments, the immunosuppressive agent and said compound or pharmaceutical composition are administered in separate dosage forms. In some embodiments, the immunosuppressive agent and said compound or pharmaceutical composition are administered in a single dosage form.

In some embodiments, the individual in need thereof is undergoing immunosuppressive therapy after organ transplantation. In some embodiments, the organ is liver, kidney, lung, heart, or the like [see, e.g., Singh et al., *Transplantation* (2000) 69:467-472].

In some embodiments, the individual in need thereof is undergoing treatment for a rheumatic disease. In some embodiments, the rheumatic disease is systemic lupus erythematosus or the like.

In some embodiments, the compound or the pharmaceutical composition inhibits JC virus infection of human glial cells 9. Hypertension Serotonin has been observed to play an important role in the regulation of vascular tone, vasoconstriction, and pulmonary hypertension (Deuchar, G. et al. *Pulm. Pharmacol. Ther.* 18(1):23-31. 2005; and Marcos, E. et al. *Circ. Res.* 94(9):1263-70 2004). Ketanserin, a $5\text{-HT}_{2A}$ inverse agonist, have been demonstrated to protect against circulatory shocks, intracranial hypertension, and cerebral ischemia during heatstroke (Chang, C. et al. *Shock* 24(4): 336-340 2005); and to stabilize blood pressure in spontaneously hypertensive rats (Miao, C. *Clin. Exp. Pharmacol. Physiol.* 30(3): 189-193). Mainserin, a $5\text{-HT}_{2A}$ inverse agonist, has been shown to prevent DOCA-salt induced hypertension in rats (Silva, A. *Eur. J. Pharmacol.* 518(2-3): 152-7 2005).

10. Pain $5\text{-HT}_{2A}$ inverse agonists are also effective for the treatment of pain. Sarpogrelate has been observed to provide a significant analgesic effect both on thermal induced pain in rats after intraperitoneal administration and on inflammatory pain in rats after either intrathecal or intraperitoneal administration (Nishiyama, T. *Eur. J. Pharmacol.* 516:18-22 2005). This same $5\text{-HT}_{2A}$ inverse agonist in humans has been shown to be an effective treatment for lower back pain, leg pain and numbness associated with sciatica brought on by lumbar disc herniation (Kanayama, M. et al. *J. Neurosurg.: Spine* 2:441-446 2005).

Pharmaceutical Compositions

A further aspect of the present invention pertains to pharmaceutical compositions comprising one or more compounds as described herein and one or more pharmaceutically acceptable carriers. Some embodiments pertain to pharmaceutical compositions comprising a compound of the present invention and a pharmaceutically acceptable carrier.

Some embodiments of the present invention include a method of producing a pharmaceutical composition comprising admixing at least one compound according to any of the compound embodiments disclosed herein and a pharmaceutically acceptable carrier.

Formulations may be prepared by any suitable method, typically by uniformly mixing the active compound(s) with liquids or finely divided solid carriers, or both, in the required proportions, and then, if necessary, forming the resulting mixture into a desired shape.

Conventional excipients, such as binding agents, fillers, acceptable wetting agents, tabletting lubricants, and disintegrants may be used in tablets and capsules for oral administration. Liquid preparations for oral administration may be in the form of solutions, emulsions, aqueous or oily suspensions, and syrups. Alternatively, the oral preparations may be in the form of dry powder that can be reconstituted with water or another suitable liquid vehicle before use. Additional additives such as suspending or emulsifying agents, non-aqueous vehicles (including edible oils), preservatives, and flavorings and colorants may be added to the liquid preparations. Parenteral dosage forms may be prepared by dissolving the compound of the invention in a suitable liquid vehicle and filter sterilizing the solution before filling and sealing an appropriate vial or ampule. These are just a few examples of the many appropriate methods well known in the art for preparing dosage forms.

A compound of the present invention can be formulated into pharmaceutical compositions using techniques well known to those in the art. Suitable pharmaceutically-acceptable carriers, outside those mentioned herein, are known in the art; for example, see Remington, *The Science and Practice of Pharmacy,* 20th Edition, 2000, Lippincott Williams & Wilkins, (Editors: Gennaro et al.).

While it is possible that, for use in the prophylaxis or treatment, a compound of the invention may, in an alternative use, be administered as a raw or pure chemical, it is preferable however to present the compound or active ingredient as a pharmaceutical formulation or composition further comprising a pharmaceutically acceptable carrier.

The invention thus further provides pharmaceutical formulations comprising a compound of the invention or a pharmaceutically acceptable salt or derivative thereof together with one or more pharmaceutically acceptable carriers thereof and/or prophylactic ingredients. The carrier(s) must be "acceptable" in the sense of being compatible with the other ingredients of the formulation and not overly deleterious to the recipient thereof.

Pharmaceutical formulations include those suitable for oral, rectal, nasal, topical (including buccal and sub-lingual), vaginal or parenteral (including intramuscular, subcutaneous and intravenous) administration or in a form suitable for administration by inhalation, insufflation or by a transdermal patch. Transdermal patches dispense a drug at a controlled rate by presenting the drug for absorption in an efficient manner with a minimum of degradation of the drug. Typically, transdermal patches comprise an impermeable backing layer, a single pressure sensitive adhesive and a removable protective layer with a release liner. One of ordinary skill in the art will understand and appreciate the techniques appropriate for manufacturing a desired efficacious transdermal patch based upon the needs of the artisan.

The compounds of the invention, together with a conventional adjuvant, carrier, or diluent, may thus be placed into the form of pharmaceutical formulations and unit dosages thereof, and in such form may be employed as solids, such as tablets or filled capsules, or liquids such as solutions, suspensions, emulsions, elixirs, gels or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are capsules, tablets, powders, granules or a suspension, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate. The active ingredient may also be administered by injection as a composition wherein, for example, saline, dextrose or water may be used as a suitable pharmaceutically acceptable carrier.

Compounds of the present invention or a solvate or physiologically functional derivative thereof can be used as active ingredients in pharmaceutical compositions, specifically as 5-HT$_{2A}$ serotonin receptor modulators. By the term "active ingredient" is defined in the context of a "pharmaceutical composition" and is intended to mean a component of a pharmaceutical composition that provides the primary pharmacological effect, as opposed to an "inactive ingredient" which would generally be recognized as providing no pharmaceutical benefit.

The dose when using the compounds of the present invention can vary within wide limits, and as is customary and is known to the physician, it is to be tailored to the individual conditions in each individual case. It depends, for example, on the nature and severity of the illness to be treated, on the condition of the patient, on the compound employed or on whether an acute or chronic disease state is treated or prophylaxis is conducted or on whether further active compounds are administered in addition to the compounds of the present invention. Representative doses of the present invention include, but not limited to, about 0.001 mg to about 5000 mg, about 0.001 mg to about 2500 mg, about 0.001 mg to about 1000 mg, 0.001 mg to about 500 mg, 0.001 mg to about 250 mg, about 0.001 mg to 100 mg, about 0.001 mg to about 50 mg, and about 0.001 mg to about 25 mg. Multiple doses may be administered during the day, especially when relatively large amounts are deemed to be needed, for example 2, 3 or 4, doses. Depending on the individual and as deemed appropriate from the patient's physician or caregiver it may be necessary to deviate upward or downward from the doses described herein.

The amount of active ingredient, or an active salt or derivative thereof, required for use in treatment will vary not only with the particular salt selected but also with the route of administration, the nature of the condition being treated and the age and condition of the patient and will ultimately be at the discretion of the attendant physician or clinician. In general, one skilled in the art understands how to extrapolate in vivo data obtained in a model system, typically an animal model, to another, such as a human. In some circumstances, these extrapolations may merely be based on the weight of the animal model in comparison to another, such as a mammal, preferably a human, however, more often, these extrapolations are not simply based on weights, but rather incorporate a variety of factors. Representative factors include the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized, on whether an acute or chronic disease state is being treated or prophylaxis is conducted or on whether further active compounds are administered in addition to the compounds of the present invention and as part of a drug combination. The dosage regimen for treating a disease condition with the compounds and/or compositions of this invention is selected in accordance with a variety factors as cited above. Thus, the actual dosage regimen employed may vary widely and therefore may deviate from a preferred dosage regimen and one skilled in the art will recognize that dosage and dosage regimen outside these typical ranges can be tested and, where appropriate, may be used in the methods of this invention.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations. The daily dose can be divided, especially when relatively large amounts are administered as deemed appropriate, into several, for example 2, 3 or 4, part administrations. If appropriate, depending on individual behavior, it may be necessary to deviate upward or downward from the daily dose indicated.

The compounds of the present invention can be administrated in a wide variety of oral and parenteral dosage forms. It will be obvious to those skilled in the art that the following dosage forms may comprise, as the active component, either a compound of the invention or a pharmaceutically acceptable salt of a compound of the invention.

For preparing pharmaceutical compositions from the compounds of the present invention, the selection of a suitable pharmaceutically acceptable carrier can be either solid, liquid or a mixture of both. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted to the desire shape and size.

The powders and tablets may contain varying percentage amounts of the active compound. A representative amount in a powder or tablet may contain from 0.5 to about 90 percent of the active compound; however, an artisan would know when amounts outside of this range are necessary. Suitable carriers for powders and tablets are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as an admixture of fatty acid glycerides or cocoa butter, is first melted and the active component is dispersed homogeneously therein, as by stirring. The molten homogenous mixture is then poured into convenient sized molds, allowed to cool, and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions, and emulsions, for example, water or water-propylene glycol solutions. For example, parenteral injection liquid preparations can be formulated as solutions in aqueous polyethylene glycol solution. Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The pharmaceutical compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous formulations suitable for oral use can be prepared by dissolving or suspending the active component in water and adding suitable colorants, flavors, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

For topical administration to the epidermis the compounds according to the invention may be formulated as ointments, creams or lotions, or as a transdermal patch.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

Formulations suitable for topical administration in the mouth include lozenges comprising active agent in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multi-dose form. In the latter case of a dropper or pipette, this may be achieved by the patient administering an appropriate, predetermined volume of the solution or suspension. In the case of a spray, this may be achieved for example by means of a metering atomizing spray pump.

Administration to the respiratory tract may also be achieved by means of an aerosol formulation in which the active ingredient is provided in a pressurized pack with a suitable propellant. If the compounds of the present invention or pharmaceutical compositions comprising them are administered as aerosols, for example as nasal aerosols or by inhalation, this can be carried out, for example, using a spray, a nebulizer, a pump nebulizer, an inhalation apparatus, a metered inhaler or a dry powder inhaler. Pharmaceutical forms for administration of the compounds of the present invention as an aerosol can be prepared by processes well known to the person skilled in the art. For their preparation, for example, solutions or dispersions of the compounds of the present invention in water, water/alcohol mixtures or suitable saline solutions can be employed using customary additives, for example benzyl alcohol or other suitable preservatives, absorption enhancers for increasing the bioavailability, solubilizers, dispersants and others, and, if appropriate, customary propellants, for example include carbon dioxide, CFCs, such as, dichlorodifluoromethane, trichlorofluoromethane, or dichlorotetrafluoroethane; and the like. The aerosol may conveniently also contain a surfactant such as lecithin. The dose of drug may be controlled by provision of a metered valve.

In formulations intended for administration to the respiratory tract, including intranasal formulations, the compound will generally have a small particle size for example of the order of 10 microns or less. Such a particle size may be obtained by means known in the art, for example by micronization. When desired, formulations adapted to give sustained release of the active ingredient may be employed.

Alternatively the active ingredients may be provided in the form of a dry powder, for example, a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration are preferred compositions.

The compounds according to the invention may optionally exist as pharmaceutically acceptable salts including pharmaceutically acceptable acid addition salts prepared from pharmaceutically acceptable non-toxic acids including inorganic and organic acids. Representative acids include, but are not limited to, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfiric, tartaric, oxalic, p-toluenesulfonic and the like, such as those pharmaceutically acceptable salts listed in *Journal of Pharmaceutical Sciences*, 66:1-19 (1977); incorporated herein by reference in its entirety.

The acid addition salts may be obtained as the direct products of compound synthesis. In the alternative, the free base may be dissolved in a suitable solvent containing the appropriate acid, and the salt isolated by evaporating the solvent or otherwise separating the salt and solvent. The compounds of this invention may form solvates with standard low molecular weight solvents using methods known to the skilled artisan.

Compounds of the present invention can be converted to "pro-drugs." The term "pro-drugs" refers to compounds that have been modified with specific chemical groups known in the art and when administered into an individual these groups undergo biotransformation to give the parent compound. Pro-drugs can thus be viewed as compounds of the invention containing one or more specialized non-toxic protective groups used in a transient manner to alter or to eliminate a property of the compound. In one general aspect, the "pro-drug" approach is utilized to facilitate oral absorption. A thorough discussion is provided in T. Higuchi and V. Stella, Pro-drugs as Novel Delivery Systems Vol. 14 of the A.C.S. Symposium Series; and in *Bioreversible Carriers in Drug Design*, ed. Edward B. Roche, American Pharmaceutical Association and Pergamon Press, 1987, both of which are hereby incorporated by reference in their entirety.

Some embodiments of the present invention include a method of producing a pharmaceutical composition for "combination-therapy" comprising admixing at least one compound according to any of the compound embodiments disclosed herein, together with at least one known pharmaceutical agent as described herein and a pharmaceutically acceptable carrier.

It is noted that when the 5-$HT_{2A}$ serotonin receptor modulators are utilized as active ingredients in a pharmaceutical composition, these are not intended for use only in humans, but in other non-human mammals as well. Indeed, recent advances in the area of animal health-care mandate that consideration be given for the use of active agents, such as 5-$HT_{2A}$ serotonin receptor modulators, for the treatment of a 5-$HT_{2A}$-associated disease or disorder in domestic animals (e.g., cats and dogs) and in other domestic animals (e.g., cows, chickens, fish, etc.). Those of ordinary skill in the art are readily credited with understanding the utility of such compounds in such settings.

Other Utilities

Another object of the present invention relates to radiolabeled compounds of the present invention that would be useful not only in radio-imaging but also in assays, both in vitro and in vivo, for localizing and quantitating the 5-$HT_{2A}$ serotonin receptor in tissue samples, including human, and for identifying 5-$HT_{2A}$ serotonin receptor ligands by inhibition binding of a radio-labeled compound. It is a further object of this invention to develop novel 5-$HT_{2A}$-receptor assays of which comprise such radio-labeled compounds.

The present invention embraces isotopically-labeled compounds of the present invention. Isotopically or radio-labeled compounds are those which are identical to compounds disclosed herein, but for the fact that one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^2H$ (also written as D for deuterium), $^3H$ (also written as T for tritium), $^{11}C$, $^{13}C$, $^{14}C$, $^{13}N$, $^{15}N$, $^{15}O$, $^{17}O$, $^{18}O$, $^{18}F$, $^{3}S$, $^{36}Cl$, $^{82}Br$, $^{75}Br$, $^{76}Br$, $^{77}Br$, $^{123}I$, $^{124}I$, $^{125}I$ and $^{131}I$. The radionuclide that is incorporated in the instant radio-labeled compounds will depend on the specific application of that radio-labeled compound. For example, for in vitro 5-$HT_{2A}$ serotonin receptor labeling and competition assays, compounds that incorporate $^3H$, $^{14}C$, $^{82}Br$, $^{125}I$, $^{131}I$ or $^{35}S$ will generally be most useful. For radio-imaging applications $^{11}C$, $^{18}F$, $^{125}I$, $^{123}I$, $^{124}I$, $^{131}I$, $^{75}Br$, $^{76}Br$ or $^{77}Br$ will generally be most useful.

It is understood that a "radio-labeled" or "labeled compound" is a compound of Formula (Ia) that has incorporated at least one radionuclide; in some embodiments the radionuclide is selected from the group consisting of $^3H$, $^{14}C$, $^{125}I$, $^{35}S$ and $^{82}Br$.

Certain isotopically-labeled compounds of the present invention are useful in compound and/or substrate tissue distribution assays. In some embodiments the radionuclide $^3H$ and/or $^{14}C$ isotopes are useful in these studies. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labeled compounds of the present invention can generally be prepared by following procedures analogous to those disclosed in the Drawings and Examples infra, by substituting an isotopically labeled reagent for a non-isotopically labeled reagent. Other synthetic methods that are useful are discussed infra. Moreover, it should be understood that all of the atoms represented in the compounds of the invention can be either the most commonly occurring isotope of such atoms or the scarcer radio-isotope or nonradioactive isotope.

Synthetic methods for incorporating radio-isotopes into organic compounds are applicable to compounds of the invention and are well known in the art. These synthetic methods, for example, incorporating activity levels of tritium into target molecules, are as follows:

A. Catalytic Reduction with Tritium Gas—This procedure normally yields high specific activity products and requires halogenated or unsaturated precursors.

B. Reduction with Sodium Borohydride [$^3$H]—This procedure is rather inexpensive and requires precursors containing reducible functional groups such as aldehydes, ketones, lactones, esters, and the like.

C. Reduction with Lithium Aluminum Hydride [$^3$H]—This procedure offers products at almost theoretical specific activities. It also requires precursors containing reducible functional groups such as aldehydes, ketones, lactones, esters, and the like.

D. Tritium Gas Exposure Labeling—This procedure involves exposing precursors containing exchangeable protons to tritium gas in the presence of a suitable catalyst.

E. N-Methylation using Methyl Iodide [$^3$H]—This procedure is usually employed to prepare O-methyl or N-methyl ($^3$H) products by treating appropriate precursors with high specific activity methyl iodide ($^3$H). This method in general allows for higher specific activity, such as for example, about 70-90 Ci/mmol.

Synthetic methods for incorporating activity levels of $^{125}$I into target molecules include:

A. Sandmeyer and like reactions—This procedure transforms an aryl or heteroaryl amine into a diazonium salt, such as a tetrafluoroborate salt, and subsequently to $^{125}$I labeled compound using Na$^{125}$I. A represented procedure was reported by Zhu, G-D. and co-workers in *J. Org. Chem.*, 2002, 67, 943-948.

B. Ortho $^{125}$Iodination of phenols—This procedure allows for the incorporation of $^{125}$I at the ortho position of a phenol as reported by Collier, T. L. and co-workers in *J. Labelled Compd. Radiopharm.*, 1999, 42, S264-S266.

C. Aryl and heteroaryl bromide exchange with $^{125}$I—This method is generally a two step process. The first step is the conversion of the aryl or heteroaryl bromide to the corresponding tri-alkyltin intermediate using for example, a Pd catalyzed reaction [i.e. Pd(Ph$_3$P)$_4$] or through an aryl or heteroaryl lithium, in the presence of a tri-alkyltinhalide or hexaalkylditin [e.g., (CH$_3$)$_3$SnSn(CH$_3$)$_3$]. A representative procedure was reported by Le Bas, M.-D. and co-workers in *J. Labelled Compd. Radiopharm.* 2001, 44, S280-S282.

A radiolabeled 5-HT$_{2A}$ serotonin receptor compound of Formula (Ia) can be used in a screening assay to identify/evaluate compounds. In general terms, a newly synthesized or identified compound (i.e., test compound) can be evaluated for its ability to reduce binding of the "radio-labeled compound of Formula (Ia)" to the 5-HT$_{2A}$-receptor. Accordingly, the ability of a test compound to compete with the "radio-labeled compound of Formula (Ia)" for the binding to the 5-HT$_{2A}$ serotonin receptor directly correlates to its binding affinity.

The labeled compounds of the present invention bind to the 5-HT$_{2A}$ serotonin receptor. In one embodiment the labeled compound has an IC$_{50}$ less than about 500 μM, in another embodiment the labeled compound has an IC$_{50}$ less than about 100 μM, in yet another embodiment the labeled compound has an IC$_{50}$ less than about 10 μM, in yet another embodiment the labeled compound has an IC$_{50}$ less than about 1 μM, and in still yet another embodiment the labeled inhibitor has an IC$_{50}$ less than about 0.1 μM.

Other uses of the disclosed receptors and methods will become apparent to those in the art based upon, inter alia, a review of this disclosure.

As will be recognized, the steps of the methods of the present invention need not be performed any particular number of times or in any particular sequence. Additional objects, advantages, and novel features of this invention will become apparent to those skilled in the art upon examination of the following examples thereof, which are intended to be illustrative and not intended to be limiting.

EXAMPLES

Example 1: Syntheses of Compounds of the Present Invention

Illustrated syntheses for compounds of the present invention are shown in FIGS. 1 through 4 where the symbols have the same definitions as used throughout this disclosure.

The compounds of the invention and their syntheses are further illustrated by the following examples. The following examples are provided to further define the invention without, however, limiting the invention to the particulars of these examples. The compounds described herein, supra and infra, are named according to the CS ChemDraw Ultra Version 7.0.1, AutoNom version 2.2. In certain instances common names are used and it is understood that these common names would be recognized by those skilled in the art.

Chemistry:

Proton nuclear magnetic resonance ($^1$H NMR) spectra were recorded on a Bruker Avance-400 equipped with a QNP (Quad Nucleus Probe) or a BBI (Broad Band Inverse) and z-gradient. Chemical shifts are given in parts per million (ppm) with the residual solvent signal used as reference. NMR abbreviations are used as follows: s=singlet, d=doublet, dd=doublet of doublets, dt=doublet of triplets, t=triplet, t=triplet of doublets, q=quartet, m=multiplet, bs=broad singlet. Microwave irradiations were carried out using a Smith Synthesizer™ or an Emrys Optimizer™ (Personal Chemistry). Thin-layer chromatography (TLC) was performed on silica gel 60 F$_{254}$ (Merck), preparatory thin-layer chromatography (prep TLC) was preformed on PK6F silica gel 60 A 1 mm plates (Whatman), and column chromatography was carried out on a silica gel column using Kieselgel 60, 0.063-0.200 mm (Merck). Evaporation was done under reduced pressure on a Büchi rotary evaporator. LCMS spec: HPLC-pumps: LC-10AD VP, Shimadzu Inc.; HPLC system controller: SCL-10A VP, Shimadzu Inc; UV-Detector: SPD-10A VP, Shimadzu Inc; Autosampler: CTC HTS, PAL, Leap Scientific; Mass spectrometer: API 150EX with Turbo Ion Spray source, AB/MDS Sciex; Software: Analyst 1.2.

Example 1.1: Preparation of 2-[4-(4-Chloro-1-ethyl-1H-pyrazole-3-carbonyl)-piperazin-1-yl]-1-(4-fluoro-phenyl)-ethanone (Compound 7)

Step A: Preparation of Intermediate tert-Butyl 4-(2-(4-Fluorophenyl)-2-oxoethyl)piperazine-1-carboxylate tert-Butyl piperazine-1-carboxylate (5.00 g, 26.8 mmol) and 2-bromo-1-(4-fluorophenyl)ethanone (6.99 g, 32.2 mmol) were dissolved in DMF (5 mL) and stirred for 10 min at room temperature. The crude material was purified by column chromatography eluting with a mixture of DCM and MeOH to afford the title compound (3.50 g) as an oil. $^1$H NMR (Acetonitrile-$d_3$, 400 MHz) δ 1.42 (s, 9H) 2.47 (t, J=5.0 Hz, 4H), 3.36 (t, J=5.0 Hz, 4H), 3.77 (s, 2H), 7.20 (t, J=8.8, 2H), 8.07 (td, J=2.0, 8.8 Hz, 2H). Exact mass calculated for $C_{17}H_{23}FN_2O_3$: 322.2; Found: LCMS m/z=323.4 (M+H$^+$).

Step B: Preparation of Intermediate 1-(4-Fluorophenyl)-2-(piperazin-1-yl)ethanone The oil from Step A was dissolved in 4 M HCl in dioxane (12 mL) and stirred at 45° C. for 20 min. The solvent was removed under reduced pressure to afford the dihydrochloride salt of the title compound (1.80 g) as a white solid. $^1$H NMR (Acetonitrile-$d_3$, 400 MHz) δ 3.56 (s, 8H), 5.05 (s, 2H), 7.46 (t, J=8.8, 2H), 8.10 (td, J=2.1, 8.8 Hz, 2H). Exact mass calculated for $C_{12}H_{15}FN_2O$: 222.1; Found: LCMS m/z=223.3 (M+H$^+$).

Step C: Preparation of 2-[4-(4-Chloro-1-ethyl-1H-pyrazole-3-carbonyl)-piperazin-1-yl]-1-(4-fluoro-phenyl)-ethanone 1-(4-Fluorophenyl)-2-(piperazin-1-yl)ethanone dihydrochloride (100 mg, 339 μmol) was added to a solution of 4-chloro-1-ethyl-1H-pyrazole-3-carboxylic acid (76.9 mg, 440 μmol), O-(7-azabenzotriazol-1-yl)-N,N,N',N'-tetramethyluronium hexafluorophosphate (168 mg, 440 μmol) and triethylamine (235 μL, 1.69 mmol) in THF (3.0 mL). The reaction mixture was heated to 100° C. under microwave irradiation for 20 min. The solvent was removed under reduced pressure and the residue was purified by preparative HPLC to afford the TFA salt of the title compound (115 mg) as a solid. $^1$H NMR (Acetonitrile-$d_3$, 400 MHz) δ 1.42 (t, J=7.3 Hz, 3H) 3.39 (s, 4H), 4.05 (s, 4H), 4.14 (q, J=7.3 Hz, 2H), 4.72 (s, 2H), 7.30 (dt, J=2.5, 8.8 Hz, 2H), 7.70 (s, 1H), 8.02 (m, 2H). Exact mass calculated for $C_{18}H_{20}ClFN_4O_2$: 378.1; Found: LCMS m/z (%)=379.1 (M+H$^+$ $^{35}$Cl, 100%), 381.1 (M+H$^+$ $^{37}$Cl, 32%).

Example 1.2: Preparation of 1-(4-Fluoro-phenyl)-2-[4-(5-methyl-2H-pyrazole-3-carbonyl)-piperazin-1-yl]-ethanone (Compound 50)

To a solution of 1-(4-fluorophenyl)-2-(piperazin-1-yl)ethanone dihydrochloride (29.5 mg, 0.100 mmol, from Step B of Example 1.1), 3-methyl-1H-pyrazole-5-carboxylic acid (18.9 mg, 0.150 mmol), and triethylamine (0.139 mL, 1.00 mmol) in DMF (0.5 mL) was added 1-propylphosphonic acid anhydride solution (50 wt. % in ethyl acetate, 122 μL, 0.200 mmol). The mixture was stirred for 2 h, quenched with water and purified by preparative HPLC/MS. The resultant lyophilate was dissolved in DCM, treated with MP-carbonate resin (~100 mg). The mixture was stirred for 30 min and filtered to remove the resin. The solvent was removed under reduce pressure to afford the title compound (26.0 mg) as a white solid. $^1$H NMR (400 MHz, CDCl$_3$) δ 2.34 (s, 3H), 2.66 (bs, 4H), 3.82 (s, 2H), 3.88 (bs, 2H), 4.02 (bs, 2H), 6.38 (s, 1H), 7.14 (t, J=8.59 Hz, 2H), 7.99-8.09 (m, 2H). Exact mass calculated for $C_{17}H_{19}FN_4O_2$: 330.2; Found: LCMS m/z=331.3 (M+H$^+$).

Example 1.3: Preparation of 1-(4-Fluoro-phenyl)-2-[4-(5-isopropyl-2H-pyrazole-3-carbonyl)-piperazin-1-yl]-ethanone (Compound 45)

The title compound was prepared in a similar manner as described in Example 1.2, using 3-isopropyl-1H-pyrazole-5-carboxylic acid (23.1 mg), and 1-(4-fluorophenyl)-2-(piperazin-1-yl)ethanone dihydrochloride (29.5 mg) as starting materials, to afford the title compound (27.1 mg) as a white solid. Exact mass calculated for $C_{19}H_{23}FN_4O_2$: 358.2, Found: LCMS m/z=359.3 (M+H$^+$).

Example 1.4: Preparation of 2-[4-(4-Chloro-1H-pyrazole-3-carbonyl)-piperazin-1-yl]-1-(4-fluoro-phenyl)-ethanone (Compound 40)

The title compound was prepared in a similar manner as described in Example 1.2, using 4-chloro-1H-pyrazole-3-carboxylic acid (22.0 mg), and 1-(4-fluorophenyl)-2-(piperazin-1-yl)ethanone dihydrochloride (29.5 mg) as starting materials, to afford the title compound (22.9 mg) as a white solid. Exact mass calculated for $C_{16}H_{16}ClFN_4O_2$: 350.1; Found: LCMS m/z (%)=351.3 (M+H$^+$ $^{35}$Cl, 100%), 353.3 (M+H$^+$ $^{37}$Cl, 32%).

Example 1.5: Preparation of 1-(4-Fluoro-phenyl)-2-[4-(5-methyl-2-phenyl-2H-pyrazole-3-carbonyl)-piperazin-1-yl]-ethanone (Compound 30)

The title compound was prepared in a similar manner as described in Example 1.2, using 3-methyl-1-phenyl-1H-pyrazole-5-carboxylic acid (30.3 mg), and 1-(4-fluorophenyl)-2-(piperazin-1-yl)ethanone dihydrochloride (29.5 mg) as starting materials, to afford the title compound (31.9 mg) as a white solid. $^1$H NMR (400 MHz, CDCl$_3$) δ 2.35 (s, 3H), 2.60-2.67 (m, 2H), 2.69 (bs., 2H), 3.81 (s, 2H), 3.89 (bs, 2H), 4.16 (bs, 2H), 6.62 (s, 1H), 7.13 (t, J=8.46 Hz, 2H), 7.38-7.54 (m, 5H), 7.99-8.09 (m, 2H). Exact mass calculated for $C_{23}H_{23}FN_4O_2$: 406.2; Found: LCMS m/z=407.5 (M+H$^+$).

Example 1.6: Preparation of 2-[4-(5-tert-Butyl-2-methyl-2H-pyrazole-3-carbonyl)-piperazin-1-yl]-1-(4-fluoro-phenyl)-ethanone (Compound 20)

The title compound was prepared in a similar manner as described in Example 1.2, using 3-tert-butyl-1-methyl-1H-pyrazole-5-carboxylic acid (27.3 mg), and 1-(4-fluorophenyl)-2-(piperazin-1-yl)ethanone dihydrochloride (29.5 mg) as starting materials, to afford the title compound (35.5 mg) as a yellow solid. Exact mass calculated for $C_{21}H_{27}FN_4O_2$: 386.2; Found: LCMS m/z=387.5 (M+H$^+$).

Example 1.7: Preparation of {4-[2-(4-Fluoro-phenyl)-ethyl]-piperazin-1-yl}-(5-methyl-1H-pyrazol-3-yl)-methanone (Compound 67)

Step A: Preparation of Intermediate tert-Butyl 4-(4-fluorophenethyl)piperazine-1-carboxylate tert-Butyl piperazine-1-carboxylate (1.00 g, 5.37 mmol) was dissolved in DMF (20 mL). 1-(2-bromoethyl)-4-fluorobenzene (2.62 g, 12.9 mmol) and potassium carbonate (2.23 g, 16.1 mmol) were then added to the solution. The reaction was heated for 1 h at 120° C. under microwave irradiation in a heavy-walled sealed tube. The product was purified by HPLC (5-95% acetonitrile/water/0.1% TFA) to afford the TFA salt of the title compound (1.65 g, 84% purity) as an oil. Exact mass calculated for $C_{17}H_{25}FN_2O_2$: 308.2; Found: LCMS m/z=309.4 (M+H$^+$).

Step B: Preparation of Intermediate 1-(4-Fluorophenethyl)piperazine tert-Butyl 4-(4-fluorophenethyl)piperazine-1-carboxylate (1.65 g, 5.37 mmol) and 4 M HCl in dioxane (6 mL) were stirred at 43° C. for 1 h. The product was purified by HPLC (5-50% acetonitrile/water/0.1% TFA) to afford the TFA salt of the title compound (510 mg) as a solid. Exact mass calculated for $C_{12}H_{17}FN_2$: 208.1; Found: LCMS m/z=209.0 (M+H$^+$).

Step C: Preparation of {4-[2-(4-Fluoro-phenyl)-ethyl]-piperazin-1-yl}-(5-methyl-1H-pyrazol-3-yl)-methanone 1-(4-Fluorophenethyl)piperazine (62 mg; 0.30 mmol), 5-methyl-1H-pyrazole-3-carboxylic acid (49 mg, 0.39 mmol), O-(7-azabenzotriazol-1-yl)-N,N,N',N'-tetramethyluronium hexafluorophosphate (147 mg, 0.39 mmol), triethylamine (89 µL, 0.6 mmol) and THF (1 mL) were heated for 10 min at 100° C. under microwave irradiation in a heavy-walled sealed tube. The solvent was evaporated and the resulting oil was dissolved in acetonitrile (3 mL) and purified by preparative HPLC to afford the TFA salt of the title compound (49 mg) as a solid. $^1$H NMR (Acetonitrile-d$_3$, 400 MHz) δ 2.29 (s, 3H), 3.03-3.07 (m, 4H), 3.25-3.29 (m, 3H), 3.48-3.67 (m, 3H), 4.61-4.76 (m, 1H), 5.09-5.24 (m, 1H), 6.41 (s, 1H), 7.09 (t, J=8.84 Hz, 2H), 7.29 (dd, J=5.05, 8.84 Hz, 2H). Exact mass calculated for $C_{17}H_{21}FN_4O$: 316.2; Found: LCMS m/z=317.1 (M+H$^+$).

Example 1.8: Preparation of (1,5-Dimethyl-1H-pyrazol-3-yl)-{4-[2-(4-fluoro-phenyl)-ethyl]-piperazin-1-yl}-methanone (Compound 61)

The title compound was prepared in a similar manner as described in Example 1.7, using 1-(4-fluorophenethyl)piperazine (62 mg, 0.3 mmol), and 1,5-dimethyl-1H-pyrazole-3-carboxylic acid (54 mg, 0.39 mmol) as starting materials, to afford the TFA salt (90 mg) as a solid. $^1$H NMR (Acetonitrile-d$_3$, 400 MHz) δ 2.27 (s, 3H), 3.03-3.07 (m, 4H), 3.23-3.31 (m, 3H), 3.50-3.65 (m, 3H), 3.76 (s, 3H), 4.61-4.76 (m, 1H), 5.09-5.24 (m, 1H), 6.42 (s, 1H), 7.09 (t, J=8.84 Hz, 2H), 7.29 (dd, J=5.05, 8.84 Hz, 2H). Exact mass calculated for $C_{18}H_{23}FN_4O$: 330.2; Found: LCMS m/z=331.4 (M+H$^+$).

Example 1.9: Preparation of {4-[2-(4-Fluoro-phenyl)-ethyl]-piperazin-1-yl}-(5-isopropyl-2H-pyrazol-3-yl)-methanone (Compound 56)

The title compound was prepared in a similar manner as described in Example 1.7, using 1-(4-fluorophenethyl)piperazine (87 mg, 0.42 mmol), and 3-isopropyl-1H-pyrazole-5-carboxylic acid (64 mg, 0.42 mmol) as starting materials, to afford the TFA salt (67 mg) as a solid. $^1$H NMR (Acetonitrile-d$_3$, 400 MHz) δ 1.27 (d, J=7.07 Hz, 6H), 2.98-3.09 (m, 5H), 3.23-3.28 (m, 4H), 3.49-3.66 (m, 2H), 4.61-4.76 (m, 1H), 5.10-5.27 (m, 1H), 6.44 (s, 1H), 7.09 (t, J=8.84 Hz, 2H), 7.28 (dd, J=5.05, 8.84 Hz, 2H). Exact mass calculated for $C_{19}H_{25}FN_4O$: 344.2; Found: LCMS m/z=345.4 (M+H$^+$).

Example 1.10: Preparation of (4-Bromo-1,5-dimethyl-1H-pyrazol-3-yl)-{4-[2-(4-fluoro-phenyl)-ethyl]-piperazin-1-yl}-methanone (Compound 51)

(4-(4-Fluorophenethyl)piperazin-1-yl)(1,5-dimethyl-1H-pyrazol-3-yl)methanone (150 mg, 0.45 mmol), and NBS (97 mg, 0.54 mmol) in DMF (1.5 mL) were heated for 20 min at 100° C. under microwave irradiation in a heavy-walled sealed tube. The product was purified by preparative HPLC to afford the TFA salt of the title compound (86 mg) as a solid. $^1$H NMR (Acetonitrile-d$_3$, 400 MHz) δ 2.26 (s, 3H), 3.01-3.08 (m, 4H), 3.27-3.32 (m, 3H), 3.47-3.65 (m, 3H), 3.79 (s, 3H), 4.33-4.45 (m, 1H), 4.63-4.72 (m, 1H), 7.09 (t, J=8.84 Hz, 2H), 7.29 (dd, J=5.05, 8.84 Hz, 2H). Exact mass calculated for $C_{18}H_{22}BrFN_4O$: 408.1; Found: LCMS m/z=409.1 (M+H$^+$ $^{79}$Br, 100%), 411.1 (M+H$^+$ $^{81}$Br, 97%).

Example 1.11: Preparation of (4-Chloro-1,5-dimethyl-1H-pyrazol-3-yl)-{4-[2-(4-fluoro-phenyl)-ethyl]-piperazin-1-yl}-methanone (Compound 46)

(4-(4-Fluorophenethyl)piperazin-1-yl)(1 1,5-dimethyl-1H-pyrazol-3-yl)methanone (100 mg, 0.300 mmol), and NCS (49 mg, 0.36 mmol) in DMF (1.5 mL) were heated for 10 min at 100° C. under microwave irradiation in a heavy-walled sealed tube. The product was purified by preparative HPLC to afford the TFA salt of the title compound (71 mg) as a solid. $^1$H NMR (Acetonitrile-d$_3$, 400 MHz) δ 2.25 (s, 3H), 3.01-3.10 (m, 4H), 3.26-3.33 (m, 2H), 3.46-3.71 (m, 4H), 3.77 (s, 3H), 4.39-4.51 (m, 1H), 4.62-4.72 (m, 1H), 7.10 (t, J=8.84 Hz, 2H), 7.29 (dd, J 5.05, 8.84 Hz, 2H). Exact mass calculated for $C_{18}H_{22}ClFN_4O$: 364.2; Found: LCMS m/z=365.4 (M+H$^+$).

Example 1.12: Preparation of {4-[2-(4-Fluoro-phenyl)-ethyl]-piperazin-1-yl}-(2-methyl-2H-pyrazol-3-yl)-methanone (Compound 41)

The title compound was prepared in a similar manner as described in Example 1.7, using 1-(4-fluorophenethyl)piperazine (200 mg, 0.96 mmol), and 1-methyl-1H-pyrazole-5-carboxylic acid (157 mg, 1.25 mmol) as starting materials, to afford the TFA salt (371 mg) as a solid. $^1$H NMR (Acetonitrile-d$_3$, 400 MHz) δ 3.01-3.10 (m, 4H), 3.28-3.34 (m, 2H), 3.48-3.65 (m, 4H), 3.90 (s, 3H), 4.58-4.96 (m, 2H), 6.43 (d, J=2.02 Hz, 1H), 7.09 (t, J=8.84 Hz, 2H), 7.29 (dd, J=5.05, 8.84 Hz, 2H), 7.46 (d, J=2.02 Hz, 1H). Exact mass calculated for $C_{17}H_{21}FN_4O$: 316.2; Found: LCMS m/z=317.3 (M+H$^+$).

Example 1.13: Preparation of (4-Bromo-1-methyl-1H-pyrazol-3-yl)-{4-[2-(4-fluoro-phenyl)-ethyl]-piperazin-1-yl}-methanone (Compound 36)

The title compound was prepared in a similar manner as described in Example 1.7, using 1-(4-fluorophenethyl)piperazine (68 mg, 0.33 mmol), and 4-bromo-1-methyl-1H-pyrazole-3-carboxylic acid (87 mg, 0.42 mmol) as starting materials, to afford the TFA salt (111 mg) as a solid. $^1$H NMR (Acetonitrile-d$_3$, 400 MHz) δ 3.01-3.09 (m, 4H), 3.27-3.33 (m, 2H), 3.48-3.74 (m, 4H), 3.86 (s, 3H), 4.29-4.42 (m, 1H), 4.63-4.73 (m, 1H), 7.09 (t, J=8.84 Hz, 2H), 7.29 (dd, J=5.05, 8.84 Hz, 2H), 7.67 (s, 1H). Exact mass calculated for C$_{17}$H$_{20}$BrFN$_4$O: 394.1; Found: LCMS m/z=395.3 (M+H$^+$ $^{79}$Br, 100%), 397.3 (M+H$^+$ $^{81}$Br, 97%).

Example 1.14: Preparation of (4-Bromo-2-methyl-2H-pyrazol-3-yl)-{4-[2-(4-fluoro-phenyl)-ethyl]-piperazin-1-yl}-methanone (Compound 31)

The title compound was prepared in a similar manner as described in Example 1.10, using (4-(4-fluorophenethyl)piperazin-1-yl)(1-methyl-1H-pyrazol-5-yl)methanone (150 mg, 0.470 mmol), and NBS (101 mg, 0.570 mmol) as starting materials, to afford the TFA salt (20 mg) as a solid. $^1$H NMR (Acetonitrile-d$_3$, 400 MHz) δ 2.41-2.84 (m, 2H), 3.04-3.09 (m, 2H), 3.24-3.29 (m, 2H), 3.31-3.46 (m, 4H), 3.66-3.79 (m, 2H), 3.84 (s, 3H), 7.08 (t, J=8.84 Hz, 2H), 7.28 (dd, J=5.05, 8.84 Hz, 2H), 7.48 (s, 1H). Exact mass calculated for C$_{17}$H$_{20}$BrFN$_4$O: 394.1; Found: LCMS m/z=395.3 (M+H$^+$ $^{79}$Br, 100%), 397.3 (M+H$^+$ $^{81}$Br, 97%).

Example 1.15: Preparation of (4-Bromo-2,5-dimethyl-2H-pyrazol-3-yl)-{4-[2-(4-fluoro-phenyl)-ethyl]-piperazin-1-yl}-methanone (Compound 26)

The title compound was prepared in a similar manner as described in Example 1.7, using 1-(4-fluorophenethyl)piperazine (62 mg, 0.3 mmol), and 4-bromo-1,3-dimethyl-1H-pyrazole-5-carboxylic acid (85 mg, 0.39 mmol) as starting materials, to afford the TFA salt (70 mg) as a solid. $^1$H NMR (Acetonitrile-d$_3$, 400 MHz) δ 2.14-2.17 (m, 2H), 2.16 (s, 3H), 2.51-2.56 (m, 2H), 2.57-2.62 (m, 2H), 2.73-2.79 (m, 2H), 3.28-3.37 (m, 2H), 3.65-3.71 (m, 2H), 3.72 (s, 3H), 7.02 (t, J=8.84 Hz, 2H), 7.24 (dd, J=5.05, 8.84 Hz, 2H). Exact mass calculated for C$_{18}$H$_{22}$BrFN$_4$O: 408.1; Found: LCMS m/z=409.4 (M+H$^+$ $^{79}$Br, 100%), 411.4 (M+H$^+$ $^{81}$Br, 97%).

Example 1.16: Preparation of 2-[4-(1,5-Dimethyl-1H-pyrazole-3-carbonyl)-piperazin-1-yl]-1-(4-fluoro-phenyl)-ethanone (Compound 1)

Step A: Preparation of Intermediate tert-Butyl 4-(2-(4-Fluorophenyl)-2-oxoethyl)piperazine-1-carboxylate tert-Butyl piperazine-1-carboxylate (5.00 g, 26.8 mmol) was dissolved in DMF (15 mL). 2-Bromo-1-(4-fluorophenyl)ethanone (7.00 g, 32.2 mmol) and potassium carbonate (11.1 g, 80.5 mmol) were then added to the solution. The reaction was stirred at room temperature for 10 min. The product was purified by HPLC (5-95% acetonitrile/water/0.1% TFA) to afford the TFA salt of the title compound (9.06 g) as an oil. Exact mass calculated for C$_{17}$H$_{23}$FN$_2$O$_3$: 322.2; Found: 323.2 (M+H$^+$).

Step B: Preparation of Intermediate 1-(4-Fluorophenyl)-2-(piperazin-1-yl)ethanone tert-Butyl 4-(2-(4-fluorophenyl)-2-oxoethyl)piperazine-1-carboxylate (8.65 g, 26.8 mmol), 4 M HCl in dioxane (6 mL) and dioxane (20 mL) were stirred at 43° C. for 1 h. The solvent was removed under reduced pressure and the residue was dried in a vacuum oven to yield the title compound (5.29 g). Exact mass calculated for C$_{12}$H$_{15}$FN$_2$O: 222.1; Found: 223.4 (M+H$^+$).

Step C: Preparation of 2-[4-(1,5-Dimethyl-1H-pyrazole-3-carbonyl)-piperazin-1-yl]-1-(4-fluoro-phenyl)-ethanone 1-(4-Fluorophenyl)-2-(piperazin-1-yl)ethanone (295 mg, 1.00 mmol), 1,5-dimethyl-1H-pyrazole-3-carboxylic acid (182 mg, 1.30 mmol), O-(7-azabenzotriazol-1-yl)-N,N,N',N'-tetramethyluronium hexafluorophosphate (490 mg, 1.30 mmol), triethylamine (297 µL, 2.00 mmol) and THF (3.5 mL) were heated for 10 min at 100° C. under microwave irradiation in a heavy-walled sealed tube. The solvent was evaporated and the resulting oil was dissolved in acetonitrile (3 mL) and purified by preparative HPLC to afford the TFA salt of the title compound (411 mg) as a solid. $^1$H NMR (Acetonitrile-d$_3$, 400 MHz) δ 2.27 (s, 3H), 3.19-3.58 (m, 4H), 3.76 (s, 3H), 3.84-4.17 (m, 4H), 4.76 (s, 2H), 6.43 (s, 1H), 7.32 (t, J=8.84 Hz, 2H), 8.02 (dd, J=5.31, 8.84 Hz, 2H). Exact mass calculated for C$_{18}$H$_{21}$FN$_4$O$_2$: 344.2; Found: LCMS m/z=345.4 (M+H$^+$).

Example 1.17: Preparation of 2-[4-(4-Bromo-1,5-dimethyl-1H-pyrazole-3-carbonyl)-piperazin-1-yl]-1-(4-fluoro-phenyl)-ethanone (Compound 68)

The title compound was prepared in a similar manner as described in Example 1.10, using 2-[4-(1,5-dimethyl-1H-pyrazole-3-carbonyl)-piperazin-1-yl]-1-(4-fluoro-phenyl)-ethanone (194 mg, 0.560 mmol), and NBS (120 mg, 0.680 mmol) as starting materials, to afford the TFA salt (51 mg) as a solid. $^1$H NMR (Acetonitrile-d$_3$, 400 MHz) δ 2.27 (s, 3H), 3.30-3.53 (m, 4H), 3.79 (s, 3H), 3.78-4.28 (m, 2H), 4.46-5.05 (m, 2H), 4.77 (s, 2H), 7.32 (t, J=8.84 Hz, 2H), 8.02 (dd, J=5.31, 8.84 Hz, 2H). Exact mass calculated for C$_{18}$H$_{20}$BrFN$_4$O$_2$: 422.1; Found: LCMS m/z=423.3 (M+H$^+$ $^{79}$Br, 100%), 425.3 (M+H$^+$ $^{81}$Br, 97%).

Example 1.18: Preparation of 2-[4-(4-Chloro-1,5-dimethyl-1H-pyrazole-3-carbonyl)-piperazin-1-yl]-1-(4-fluoro-phenyl)-ethanone (Compound 62)

The title compound was prepared in a similar manner as described in Example 1.10, using 2-[4-(1,5-dimethyl-1H-pyrazole-3-carbonyl)-piperazin-1-yl]-1-(4-fluoro-phenyl)-ethanone (194 mg, 0.56 mmol), and NCS (90 mg, 0.68 mmol) as starting materials, to afford the TFA salt (143 mg) as a solid. $^1$H NMR (Acetonitrile-d$_3$, 400 MHz) δ 2.25 (s, 3H), 3.27-3.53 (m, 4H), 3.77 (s, 3H), 3.88-4.28 (m, 2H), 4.48-4.78 (m, 2H), 4.77 (s, 2H), 7.32 (t, J=8.84 Hz, 2H), 8.02 (dd, J=5.31, 8.84 Hz, 2H). Exact mass calculated for C$_{18}$H$_{20}$ClFN$_4$O$_2$: 378.1; Found: LCMS m/z=379.3 (M+H$^+$).

Example 1.19: Preparation of 2-[4-(4-Chloro-5-methyl-1H-pyrazole-3-carbonyl)-piperazin-1-yl]-1-(4-fluoro-phenyl)-ethanone (Compound 57)

The title compound was prepared in a similar manner as described in Example 1.10, using 1-(4-fluorophenyl)-2-(4-(5-methyl-1H-pyrazole-3-carbonyl)piperazin-1-yl)ethanone (80 mg, 0.24 mmol), and NCS (65 mg, 0.49 mmol) as starting materials, to afford the TFA salt (7 mg) as a solid. $^1$H NMR (Acetonitrile-d$_3$, 400 MHz) δ 2.26 (s, 3H), 3.34-3.53 (m, 6H), 3.98-4.13 (m, 2H), 4.74 (s, 2H), 7.31 (t, J=8.84 Hz, 2H), 8.01 (dd, J=5.31, 8.84 Hz, 2H). Exact mass calculated for C$_{17}$H$_{18}$ClFN$_4$O$_2$: 364.1; Found: LCMS m/z=365.4 (M+H$^+$).

Example 1.20: Preparation of 2-[4-(4-Bromo-5-methyl-1H-pyrazole-3-carbonyl)-piperazin-1-yl]-1-(4-fluoro-phenyl)-ethanone (Compound 52)

The title compound was prepared in a similar manner as described in Example 1.10, using 1-(4-fluorophenyl)-2-(4-(5-methyl-1H-pyrazole-3-carbonyl)piperazin-1-yl)ethanone (80 mg, 0.24 mmol), and NBS (116 mg, 0.65 mmol) as starting materials, to afford the TFA salt (11 mg) as a solid. $^1$H NMR (Acetonitrile-$d_3$, 400 MHz) δ 2.26 (s, 3H), 3.33-3.52 (m, 4H), 3.93-4.12 (m, 4H), 4.74 (s, 2H), 7.30 (t, J=8.84 Hz, 2H), 8.01 (dd, J=5.31, 8.84 Hz, 2H). Exact mass calculated for $C_{17}H_{18}BrFN_4O_2$: 408.1; Found: LCMS m/z=409.3 (M+H$^+$ $^{79}$Br, 100%), 411.3 (M+H$^+$ $^{79}$Br, 97%).

Example 1.21: Preparation of 1-(4-Fluoro-phenyl)-2-[4-(4-iodo-1-methyl-1H-pyrazole-3-carbonyl)-piperazin-1-yl]-ethanone (Compound 47)

The title compound was prepared in a similar manner as described in Example 1.7, using 1-(4-fluorophenyl)-2-(piperazin-1-yl)ethanone (180 mg, 0.8 mmol), and 4-iodo-1-methyl-1H-pyrazole-3-carboxylic acid (265 mg, 1.00 mmol) as starting materials, to afford the TFA salt (390 mg) as a solid. $^1$H NMR (Acetonitrile-$d_3$, 400 MHz) δ 3.18-3.72 (m, 4H), 3.88 (s, 3H), 4.07-4.52 (m, 4H), 4.79 (s, 2H), 7.33 (t, J=8.84 Hz, 2H), 7.69 (s, 1H), 8.02 (dd, J=5.31, 8.84 Hz, 2H). Exact mass calculated for $C_{17}H_{18}FIN_4O_2$: 456.1; Found: LCMS m/z=457.3 (M+H$^+$).

Example 1.22: Preparation of 2-[4-(4-Fluoro-5-methyl-1H-pyrazole-3-carbonyl)-piperazin-1-yl]-1-(4-fluoro-phenyl)-ethanone (Compound 42)

The title compound was prepared in a similar manner as described in Example 1.7, using 1-(4-fluorophenyl)-2-(piperazin-1-yl)ethanone (44 mg, 0.2 mmol), and 4-fluoro-5-methyl-1H-pyrazole-3-carboxylic acid (37 mg, 0.26 mmol) as starting materials, to afford the TFA salt (71 mg) as a solid. $^1$H NMR (Acetonitrile-$d_3$, 400 MHz) δ 2.23 (s, 3H), 3.34-3.50 (m, 4H), 3.91-3.31 (m, 4H), 4.72 (s, 2H), 7.30 (t, J=8.84 Hz, 2H), 8.01 (dd, J=5.31, 8.84 Hz, 2H). Exact mass calculated for $C_{17}H_{18}F_2N_4O_2$: 348.1; Found: LCMS m/z=349.4 (M+H$^+$).

Example 1.23: Preparation of 2-[4-(5-Ethyl-4-fluoro-1H-pyrazole-3-carbonyl)-piperazin-1-yl]-1-(4-fluoro-phenyl)-ethanone (Compound 37)

The title compound was prepared in a similar manner as described in Example 1.7, using 1-(4-fluorophenyl)-2-(piperazin-1-yl)ethanone (44 mg, 0.2 mmol), and 5-ethyl-4-fluoro-1H-pyrazole-3-carboxylic acid (41 mg, 0.26 mmol) as starting materials, to afford the TFA salt (61 mg) as a solid. $^1$H NMR (Acetonitrile-$d_3$, 400 MHz) δ 1.24 (t, J=7.83 Hz, 3H), 2.67 (q, J=7.83 Hz, 2H), 3.36-3.50 (m, 4H), 3.54-3.86 (m, 2H), 3.94-4.31 (m, 2H), 4.73 (s, 2H), 7.31 (t, J=8.84 Hz, 2H), 8.01 (dd, J=5.31, 8.84 Hz, 2H). Exact mass calculated for $C_{18}H_{20}F_2N_4O_2$: 362.2; Found: LCMS m/z=363.3 (M+H$^+$).

Example 1.24: Preparation of 2-[4-(5-Cyclopropyl-4-fluoro-1H-pyrazole-3-carbonyl)-piperazin-1-yl]-1-(4-fluoro-phenyl)-ethanone (Compound 32)

The title compound was prepared in a similar manner as described in Example 1.7, using 1-(4-fluorophenyl)-2-(piperazin-1-yl)ethanone (44 mg, 0.2 mmol), and 5-cyclopropyl-4-fluoro-1H-pyrazole-3-carboxylic acid (44 mg, 0.26 mmol) as starting materials, to afford the TFA salt (42 mg) as a solid. $^1$H NMR (Acetonitrile-$d_3$, 400 MHz) δ 0.82-0.85 (m, 2H), 0.94-0.99 (m, 2H), 1.83-1.90 (m, 1H), 3.37-3.48 (m, 4H), 3.92-4.25 (m, 4H), 4.73 (s, 2H), 7.30 (t, J=8.84 Hz, 2H), 8.01 (dd, J=5.31, 8.84 Hz, 2H). Exact mass calculated for $C_{19}H_{20}F_2N_4O_2$: 374.2; Found: LCMS m/z=375.3 (M+H$^+$).

Example 1.25: Preparation of 1-(4-Fluoro-phenyl)-2-[4-(1-methyl-4-o-tolyl-1H-pyrazole-3-carbonyl)-piperazin-1-yl]-ethanone (Compound 27)

1-(4-Fluoro-phenyl)-2-[4-(4-iodo-1-methyl-1H-pyrazole-3-carbonyl)-piperazin-1-yl]-ethanone (68 mg, 0.15 mmol), o-tolylboronic acid (44 mg, 0.33 mmol), tetrakis(triphenylphosphine)palladium(0) (26 mg, 0.02 mmol), $K_2CO_3$ (42 mg, 0.3 mmol) and THF (1 mL) were heated for 2 h at 120° C. under microwave irradiation in a heavy-walled sealed tube. The solvent was evaporated and the resulting oil was dissolved in acetonitrile (3 mL) and purified by preparative HPLC to afford the TFA salt of the title compound (30 mg) as a solid. $^1$H NMR (Methanol-$d_4$, 400 MHz) δ 2.27 (s, 3H), 2.96-3.11 (m, 2H), 3.04-3.09 (m, 2H), 3.33-3.44 (m, 2H), 3.76-3.92 (m, 2H), 4.00 (s, 3H), 4.90 (s, 2H), 7.11-7.41 (m, 6H), 7.77 (s, 1H), 8.06-8.11 (m, 2H). Exact mass calculated for $C_{24}H_{25}FN_4O_2$: 420.2; Found: LCMS m/z=421.4 (M+H$^+$).

Example 1.26: Preparation of (4-Bromo-1-methyl-1H-pyrazol-3-yl)-{4-[2-(4-fluoro-phenyl)-2-hydroxy-ethyl]-piperazin-1-yl}-methanone (Compound 77)

2-(4-(4-bromo-1-methyl-1H-pyrazole-3-carbonyl)piperazin-1-yl)-1-(4-fluorophenyl)ethanone (30 mg, 0.070 mmol) was taken up in MeOH (4 mL) and chilled to 0° C. Sodium borohydride (2.8 mg, 0.070 mmol) was added portion wise. Then the reaction mixture was stirred at room temperature for 5 min and quenched with water. The solvent was removed under reduced pressure. The crude product was purified by preparative HPLC to afford the TFA salt of the title compound (25 mg) as a solid. $^1$H NMR (Acetonitrile-$d_3$, 400 MHz) δ 2.92-4.16 (m, 8H), 3.23-3.29 (m, 2H), 3.87 (s, 3H), 5.15-5.20 (m, 1H), 7.14 (t, J=8.84 Hz, 2H), 7.44 (dd, J=5.31, 8.84 Hz, 2H), 7.67 (s, 1H). Exact mass calculated for $C_{17}H_{20}BrFN_4O_2$: 410.1; Found: LCMS m/z (%)=411.2 (M+H$^+$ $^{79}$Br, 100%), 413.2 (M+H$^+$ $^{81}$Br, 97%).

Example 1.27: Preparation of 2-[4-(4-Bromo-1-methyl-1H-pyrazole-3-carbonyl)-piperazin-1-yl]-1-(3,4-difluoro-phenyl)-ethanone (Compound 48)

The title compound was prepared in a similar manner as described in Example 1.7, using (4-bromo-1-methyl-1H-pyrazol-3-yl)(piperazin-1-yl)methanone (75 mg, 0.24 mmol), and 2-bromo-1-(3,4-difluorophenyl)ethanone (57 mg, 0.24 mmol) as starting materials, to afford the TFA salt (14 mg) as a solid. $^1$H NMR (Methanol-$d_4$, 400 MHz) δ 3.44-3.56 (m, 4H), 3.93 (s, 3H), 4.03-4.17 (m, 4H), 5.01 (s, 2H), 7.48-7.57 (m, 1H), 7.85 (s, 1H), 7.88-7.94 (m, 1H), 7.96-8.02 (m, 1H). Exact mass calculated for $C_{17}H_{17}BrF_2N_4O_2$: 426.1; Found: LCMS m/z (%)=427.1 (M+H$^+$ $^{79}$Br, 100%), 429.1 (M+H$^+$ $^{81}$Br, 97%).

Example 1.28: Preparation of 2-[4-(4-Bromo-1-methyl-1H-pyrazole-3-carbonyl)-piperazin-1-yl]-1-(4-trifluoromethyl-phenyl)-ethanone (Compound 33)

The title compound was prepared in a similar manner as described in Example 1.7, using (4-bromo-1-methyl-1H-pyrazol-3-yl)(piperazin-1-yl)methanone (75 mg, 0.24 mmol), and 2-bromo-1-(4-(trifluoromethyl)phenyl)ethanone (65 mg, 0.24 mmol) as starting materials, to afford the TFA salt (47 mg) as a solid. $^1$H NMR (Methanol-$d_4$, 400 MHz) δ 3.47-3.56 (m, 4H), 3.93 (s, 3H), 4.04-4.16 (m, 4H), 5.08 (s, 2H), 7.85 (s, 1H), 7.92 (d, J=8.34 Hz, 2H), 8.22 (d, J=8.34 Hz, 2H). Exact mass calculated for $C_{18}H_{18}BrF_3N_4O_2$: 458.1; Found: LCMS m/z (%)=459.3 (M+H$^+$ $^{79}$Br, 100%), 461.3 (M+H$^+$ $^{81}$Br, 100%).

Example 1.29: Preparation of 2-[4-(4-Bromo-1-methyl-1H-pyrazole-3-carbonyl)-piperazin-1-yl]-1-(4-trifluoromethoxy-phenyl)-ethanone (Compound 28)

The title compound was prepared in a similar manner as described in Example 1.7, using (4-bromo-1-methyl-1H-pyrazol-3-yl)(piperazin-1-yl)methanone (75 mg, 0.24 mmol), and 2-bromo-1-(4-(trifluoromethoxy)phenyl)ethanone (68 mg, 0.24 mmol) as starting materials, to afford the TFA salt (68 mg) as a solid. $^1$H NMR (Methanol-$d_4$, 400 MHz) δ 3.46-3.56 (m, 4H), 3.93 (s, 3H), 4.04-4.18 (m, 4H), 5.04 (s, 2H), 7.50 (d, J=8.84 Hz, 2H), 7.85 (s, 1H), 8.16 (d, J=8.84 Hz, 2H). Exact mass calculated for $C_{18}H_{18}BrF_3N_4O_3$: 474.1; Found: LCMS m/z (%)=475.4 (M+H$^+$ $^{79}$Br, 100%), 477.4 (M+H$^+$ $^{81}$Br, 97%).

Example 1.30: Preparation of 2-[4-(4-Bromo-1-methyl-1H-pyrazole-3-carbonyl)-piperazin-1-yl]-1-(4-methanesulfonyl-phenyl)-ethanone (Compound 23)

The title compound was prepared in a similar manner as described in Example 1.7, using (4-bromo-1-methyl-1H-pyrazol-3-yl)(piperazin-1-yl)methanone (75 mg, 0.24 mmol), and 2-bromo-1-(4-(methylsulfonyl)phenyl)ethanone (67 mg, 0.24 mmol) as starting materials, to afford the TFA salt (8 mg) as a solid. $^1$H NMR (Methanol-$d_4$, 400 MHz) δ 3.20 (s, 3H), 3.48-3.58 (m, 4H), 3.93 (s, 3H), 4.07-4.18 (m, 4H), 5.10 (s, 2H), 7.85 (s, 1H), 8.17 (d, J=8.34 Hz, 2H), 8.26 (d, J=8.34 Hz, 2H). Exact mass calculated for $C_{18}H_{21}BrN_4O_4S$: 468.1; Found: LCMS m/z (%)=469.3 (M+H$^+$ $^{79}$Br, 100%), 471.3 (M+H$^+$ $^{81}$Br, 97%).

Example 1.31: Preparation of 2-[4-(4-Bromo-1-methyl-1H-pyrazole-3-carbonyl)-piperazin-1-yl]-1-(4-pyrrolidin-1-yl-phenyl)-ethanone (Compound 18)

The title compound was prepared in a similar manner as described in Example 1.7, using (4-bromo-1-methyl-1H-pyrazol-3-yl)(piperazin-1-yl)methanone (75 mg, 0.24 mmol), and 2-bromo-1-(4-(pyrrolidin-1-yl)phenyl)ethanone (65 mg, 0.24 mmol) as starting materials, to afford the TFA salt (65 mg) as a solid. $^1$H NMR (Methanol-$d_4$, 400 MHz) δ 2.04-2.10 (m, 4H), 3.38-3.44 (m, 4H), 3.45-3.60 (m, 4H), 3.93 (s, 3H), 3.97-4.18 (m, 4H), 4.86 (s, 2H), 6.64 (d, J=8.84 Hz, 2H), 7.85 (s, 1H), 7.86 (d, J=8.84 Hz, 2H). Exact mass calculated for $C_{21}H_{26}BrN_5O_2$: 459.1; Found: LCMS m/z (%)=460.4 (M+H$^+$ $^{79}$Br, 100%), 462.4 (M+H$^+$ $^{81}$Br, 97%).

Example 1.32: Preparation of 1-(4-Fluoro-phenyl)-2-[4-(1,4,5,6-tetrahydro-cyclopentapyrazole-3-carbonyl)-piperazin-1-yl]-ethanone (Compound 11)

The title compound was prepared in a similar manner as described in Example 1.7, using 1-(4-fluorophenyl)-2-(piperazin-1-yl)ethanone (80 mg, 0.27 mmol), and 1,4,5,6-tetrahydrocyclopenta[c]-pyrazole-3-carboxylic acid (49 mg, 0.33 mmol) as starting materials, to afford the TFA salt (57 mg) as a solid. $^1$H NMR (Methanol-$d_4$, 400 MHz) δ 2.53-2.61 (m, 2H), 2.70-2.78 (m, 4H), 3.46-3.57 (m, 4H), 3.96-4.49 (m, 4H), 5.03 (s, 2H), 7.34 (t, J=8.84 Hz, 2H), 8.12 (dd, J=5.31, 8.84 Hz, 2H). Exact mass calculated for $C_{19}H_{21}FN_4O_2$: 356.2; Found: LCMS m/z=357.2 (M+H$^+$).

Example 1.33: Preparation of 1-(4-Fluoro-phenyl)-2-{4-[1-(4-methoxy-phenyl)-5-phenyl-1H-pyrazole-3-carbonyl]-piperazin-1-yl}-ethanone (Compound 19)

The title compound was prepared in a similar manner as described in Example 1.7, using 1-(4-fluorophenyl)-2-(piperazin-1-yl)ethanone (59 mg, 0.20 mmol), and 1-(4-methoxyphenyl)-5-phenyl-1H-pyrazole-3-carboxylic acid (65 mg, 0.22 mmol) as starting materials, to afford the TFA salt (66 mg) as a solid. $^1$H NMR (Acetonitrile-$d_3$, 400 MHz) δ 3.39-3.52 (m, 4H), 3.80 (s, 3H), 3.92-4.24 (m, 2H), 4.38-4.64 (m, 2H), 4.72 (s, 2H), 6.90-6.95 (m, 3H), 7.22-7.37 (m, 9H), 8.02 (dd, J=5.31, 8.84 Hz, 2H). Exact mass calculated for $C_{29}H_{27}FN_4O_3$: 498.2; Found: LCMS m/z=499.6 (M+H$^+$).

Example 1.34: Preparation of 1-(4-Fluoro-phenyl)-2-[4-(1-methyl-5-trifluoromethyl-1H-pyrazole-3-carbonyl)-piperazin-1-yl]-ethanone (Compound 35)

The title compound was prepared in a similar manner as described in Example 1.7, using 1-(4-fluorophenyl)-2-(piperazin-1-yl)ethanone (70 mg, 0.30 mmol), and 1-methyl-5-(trifluoromethyl)-1H-pyrazole-3-carboxylic acid (65 mg, 0.33 mmol) as starting materials, to afford the TFA salt (153 mg) as a solid. $^1$H NMR (Methanol-$d_4$, 400 MHz) δ 3.48-3.62 (m, 4H), 3.92-4.29 (m, 2H), 4.07 (s, 3H), 4.34-4.69 (m, 2H), 5.03 (s, 2H), 7.19 (s, 1H), 7.34 (t, J=8.84 Hz, 2H), 8.12 (dd, J=5.31, 8.84 Hz, 2H). Exact mass calculated for $C_{18}H_{18}F_4N_4O_2$: 398.1; Found: LCMS m/z=399.4 (M+H$^+$).

Example 1.35: Preparation of 2-[4-(4-Bromo-1-methyl-1H-pyrazole-3-carbonyl)-piperazin-1-yl]-1-(4-fluoro-phenyl)-ethanone O-Methyl-oxime (Compound 25)

2-(4-(4-Bromo-1-methyl-1H-pyrazole-3-carbonyl)piperazin-1-yl)-1-(4-fluorophenyl)ethanone (100 mg, 0.24 mmol) and methoxylamine hydrochloride (25 mg, 0.31 mmol) were taken up in ethanol (10 mL) in a round-bottom flask and heated to reflux at 90° C. for 21 h. The solvent was removed under reduced pressure and saturated aqueous NaHCO$_3$ (1.5 mL) was added. The mixture was extracted three times with DCM and the organic phase was dried over sodium sulfate, filtered, and concentrated. The crude product was purified by preparative TLC plate (R$_f$=0.44, 60% EtOAc/Hexane, UV 254 nm) and dried to afford the title compound (25 mg) as a free base. $^1$H NMR (Acetonitrile-$d_3$, 400 MHz) δ 2.42-2.48 (m, 2H), 2.48-2.54 (m, 2H), 3.35-3.42 (m, 2H), 3.37 (s, 2H), 3.57-3.63 (m, 2H), 3.80 (s, 3H), 3.84 (s, 3H), 7.14 (t, J=8.84 Hz, 2H), 7.60 (dd, J=5.31, 8.84 Hz, 2H), 7.61 (s, 1H).

Exact mass calculated for $C_{18}H_{21}BrFN_5O_2$: 437.1; Found: LCMS m/z (%)=438.3 (M+H+ $^{79}$Br, 100%), 440.3 (M+H+ $^{81}$Br, 97%).

Example 1.36: Preparation of 1-(4-Fluoro-phenyl)-2-[4-(5-nitro-1H-pyrazole-3-carbonyl)-piperazin-1-yl]-ethanone (Compound 76)

To a solution of 1-(4-fluorophenyl)-2-(piperazin-1-yl)ethanone dihydrochloride (29.5 mg, 0.100 mmol), 5-nitro-1H-pyrazole-3-carboxylic acid (23.6 mg, 0.150 mmol) and triethylamine (139 µL, 1.00 mmol) in DMF (0.5 mL) was added 1-propylphosphonic acid anhydride solution (50 wt. % in ethyl acetate, 61.0 µL, 0.100 mmol). The resulting mixture was vortexed and then allowed to stand for 30 min. The product was purified by preparative HPLC/MS and lyophilized to afford the TFA salt of the title compound (20.5 mg) as a white solid. $^1$H NMR (DMSO-d$_6$, 400 MHz) δ 3.69 (bs, 6H), 4.00 (bs, 2H), 4.95 (bs, 2H), 7.47 (t, J=8.84 Hz, 2H), 7.52 (s, 1H), 8.05-8.14 (m, 2H). Exact mass calculated for $C_{16}H_{16}FN_5O_4$: 361.1; Found: LCMS m/z=362.4 (M+H+).

Example 1.37: Preparation of 2-[4-(4-Bromo-2,5-dimethyl-2H-pyrazole-3-carbonyl)-piperazin-1-yl]-1-(4-fluoro-phenyl)-ethanone (Compound 4)

The title compound was prepared in a similar manner as described in Example 1.1, using 1-(4-fluorophenyl)-2-(piperazin-1-yl)ethanone hydrochloride (35 mg, 135 µmol) and 4-bromo-1,3-dimethyl-1H-pyrazole-5-carboxylic acid (29.6 mg, 135 mol) as starting materials, to afford the TFA salt (41 mg) as a solid. $^1$H NMR (Acetonitrile-d$_3$, 400 MHz) δ 2.19 (s, 3H), 2.58 (s, 3H), 3.46 (s, 4H), 3.80 (s, 4H), 4.77 (s, 2H), 7.34 (t, J=8.8 Hz, 2H), 8.02 (m, 2H). Exact mass calculated for $C_{18}H_{20}BrFN_4O_2$: 422.1; Found: LCMS m/z (%)=423.1 (M+H+ $^{79}$Br, 100%), 425.1 (M+H+ $^{81}$Br, 97%).

Example 1.38: Preparation of 2-[4-(1-tert-Butyl-5-methyl-1H-pyrazole-3-carbonyl)-piperazin-1-yl]-1-(4-fluoro-phenyl)-ethanone (Compound 17)

1-(4-Fluorophenyl)-2-(piperazin-1-yl)ethanone dihydrochloride (59.0 mg, 0.200 mmol) was added to a solution of 1-tert-butyl-5-methyl-1H-pyrazole-3-carbonyl chloride (48.2 mg, 0.240 mmol) in triethylamine (97.4 µL, 0.700 mmol) and DCM (2.0 mL). The solution was stirred for 30 min at room temperature. The solvent was removed under reduced pressure and the residue was purified by preparative HPLC to afford the TFA salt of the title compound (48.3 mg) as a solid. $^1$H NMR (Acetonitrile-d$_3$, 400 MHz) δ 1.62 (s, 9H), 2.46 (s, 3H), 3.44 (m, 4H), 3.90-4.08 (m, 4H), 4.72 (s, 2H), 6.45 (s, 1H), 7.30 (t, J=8.8 Hz, 2H), 8.01 (dd, J=8.8, 8.8 Hz, 2H). Exact mass calculated for $C_{21}H_{27}FN_4O_2$: 386.2; Found: LCMS m/z=387.3 (M+H+).

Example 1.39: Preparation of 2-[4-(2-Ethyl-5-methyl-2H-pyrazole-3-carbonyl)-piperazin-1-yl]-1-(4-fluoro-phenyl)-ethanone (Compound 79)

The title compound was prepared in a similar manner as described in Example 1.1, Step C, using 1-ethyl-3-methyl-1H-pyrazole-5-carboxylic acid (42.1 mg, 0.273 mmol) and (1-(4-fluorophenyl)-2-(piperazin-1-yl)ethanone dihydrochloride (62.0 mg, 0.210 mmol) as starting materials, to afford the TFA salt (59.7 mg) as a solid. $^1$H NMR (Acetonitrile-d$_3$, 400 MHz) δ 1.36 (t, J=7.1 Hz, 3H), 2.21 (s, 3H), 3.39 (s, 4H), 3.98 (s, 4H), 4.17 (q, J=7.1, 2H), 4.71 (s, 2H), 6.20 (s, 1H), 7.31 (t, J=8.8, 2H), 8.02 (m, 2H). Exact mass calculated for $C_{19}H_{23}FN_4O_2$: 358.2; Found: LCMS m/z=359.5 (M+H+).

Example 1.40: Preparation of 2-[(S)-4-(4-Bromo-1-methyl-1H-pyrazole-3-carbonyl)-2-methyl-piperazin-1-yl]-1-(4-fluoro-phenyl)-ethanone (Compound 82)

The starting material, (S)-1-(4-fluorophenyl)-2-(2-methylpiperazin-1-yl)ethanone dihydrochloride, was made in a similar manner as described in Example 1.1, Steps A and B, using (S)-tert-butyl 3-methylpiperazine-1-carboxylate (1.00 g, 4.99 mmol), and 2-bromo-1-(4-fluorophenyl)ethanone (1.14 g, 5.24 mmol). The title compound was prepared in a similar manner as described in Example 1.1, Step C, using 4-bromo-1-methyl-1H-pyrazole-3-carboxylic acid (43.1 mg, 210 µmol) and (S)-1-(4-fluorophenyl)-2-(2-methylpiperazin-1-yl)ethanone dihydrochloride (50.0 mg, 162 µmol) as starting materials, to afford the TFA salt (22.6 mg) as a solid. $^1$H NMR (Acetonitrile-d$_3$, 400 MHz) δ 1.32-1.42 (dd, J=5.9, 34.9 Hz, 3H), 2.06 (s, 1H), 3.30-3.55 (m, 6H), 3.87 (s, 3H), 4.71 (q, J=17.1, 2H), 7.30 (s, J=6.9 Hz, 2H), 7.60 (s, 1H), 8.05 (dd, J=6.9, 8.8, 2H). Exact mass calculated for $C_{18}H_{20}BrFN_4O_2$: 422.1; Found: LCMS m/z (%)=423.1 (M+H+ $^{79}$Br, 100%), 425.1 (M+H+ $^{81}$Br, 97%).

Example 1.41: Preparation of 2-[(S)-4-(4-Chloro-1-methyl-1H-pyrazole-3-carbonyl)-2-methyl-piperazin-1-yl]-1-(4-fluoro-phenyl)-ethanone (Compound 80)

The title compound was prepared in a similar manner as described in Example 1.40, using 4-bromo-1-methyl-1H-pyrazole-3-carboxylic acid (43.1 mg, 210 µmol) and (S)-1-(4-fluorophenyl)-2-(2-methylpiperazin-1-yl)ethanone dihydrochloride (50.0 mg, 162 µmol) as starting materials, to afford the TFA salt (25.3 mg) as a solid. $^1$H NMR (Acetonitrile-d$_3$, 400 MHz) δ 1.32-1.42 (dd, J=5.9, 34.9 Hz, 3H), 2.08 (s, 1H), 3.30-3.60 (m, 3H), 3.87 (s, 3H), 3.90-4.25 (m, 3H), 4.72 (q, J=17.8 Hz, 2H), 7.31 (t, J=8.8 Hz, 2H), 7.65 (s, 1H), 8.05 (dd, J=2.1, 8.8 Hz, 2H). Exact mass calculated for $C_{18}H_{20}ClFN_4O_2$: 378.1; Found: LCMS m/z (%)=379.4 (M+H+ $^{35}$Cl, 100%), 381.4 (M+H+ $^{37}$Cl, 32%).

Example 1.42: Preparation of 2-[(S)-4-(4-Bromo-1,5-dimethyl-1H-pyrazole-3-carbonyl)-2-methyl-piperazin-1-yl]-1-(4-fluoro-phenyl)-ethanone (Compound 78)

The title compound was prepared in a similar manner as described in Example 1.40, using 4-bromo-1,5-dimethyl-1H-pyrazole-3-carboxylic acid (46.0 mg, 210 µmol) and (S)-1-(4-fluorophenyl)-2-(2-methylpiperazin-1-yl)ethanone dihydrochloride (50 mg, 162 µmol) as starting materials, to afford the TFA salt (25.5 mg) as a solid. $^1$H NMR (Acetonitrile-d$_3$, 400 MHz) δ 1.32-1.42 (d, J=16.0 Hz, 3H), 2.18 (s, 3H), 3.30-3.55 (m, 7H), 3.78 (s, 3H), 4.50-4.75 (s, 2H), 7.30 (t, J=8.8 Hz, 2H), 8.05 (m, 2H). Exact mass calculated for $C_{19}H_{22}BrFN_4O_2$: 436.1; Found: LCMS m/z (%)=437.3 (M+H+ $^{79}$Br, 100%), 439.3 (M+H+ $^{81}$Br, 98%).

Example 1.43: Preparation of 2-[(R)-4-(4-Bromo-1-methyl-1H-pyrazole-3-carbonyl)-2-methyl-piperazin-1-yl]-1-(4-fluoro-phenyl)-ethanone (Compound 15)

The starting material, (R)-1-(4-fluorophenyl)-2-(2-methylpiperazin-1-yl)ethanone dihydrochloride, was made in a similar manner as described in Example 1.1, Steps A and B, using (R)-tert-butyl 2-methylpiperazine-1-carboxylate (1.00 g, 4.99 mmol), 2-bromo-1-(4-fluorophenyl)ethanone (1.14 g, 5.24 mmol). The title compound was prepared in a similar manner as described in Example 1.1, Step C, using 4-bromo-1-methyl-1H-pyrazole-3-carboxylic acid (57.1 mg, 252 µmol) and (R)-1-(4-fluorophenyl)-2-(2-methylpiperazin-1-yl)ethanone dihydrochloride (60.0 mg, 194 µmol) as starting materials, to afford the TFA salt (56 mg) as a solid. $^1$H NMR (Acetonitrile-$d_3$, 400 MHz) δ 1.34-1.42 (d, J=19.9 Hz, 3H), 3.30-3.55 (m, 4H), 3.78 (s, 3H), 3.90-4.15 (m, 3H), 4.73 (m, 2H), 7.35 (t, J=8.8 Hz, 2H), 7.68 (s, 1H), 8.05 (m, 2H). Exact mass calculated for $C_{18}H_{20}BrFN_4O_2$: 422.1; Found: LCMS m/z (%)=423.3 (M+H$^+$ $^{79}$Br, 100%), 425.3 (M+H$^+$ $^{81}$Br, 97%).

Example 1.44: Preparation of 2-[(R)-4-(4-Chloro-1-methyl-1H-pyrazole-3-carbonyl)-2-methyl-piperazin-1-yl]-1-(4-fluoro-phenyl)-ethanone (Compound 12)

The title compound was prepared in a similar manner as described in Example 1.43, using 4-chloro-1-methyl-1H-pyrazole-3-carboxylic acid (40.5 mg, 252 mol) and (R)-1-(4-fluorophenyl)-2-(2-methylpiperazin-1-yl)ethanone dihydrochloride (60 mg, 194 µmol) as starting materials, to afford the TFA salt (52.8 mg) as a solid. $^1$H NMR (Acetonitrile-$d_3$, 400 MHz) δ 1.35-1.44 (d, J=29.1 Hz, 3H), 3.30-3.55 (m, 4H), 3.78 (s, 3H), 3.90-4.15 (m, 3H), 4.67-4.85 (m, 2H), 7.33 (t, J=8.8 Hz, 2H), 7.68 (s, 1H), 8.07 (m, 2H). Exact mass calculated for $C_{18}H_{20}ClFN_4O_2$: 378.1; Found: LCMS m/z (%)=379.4 (M+H$^+$ $^{35}$Cl, 100%), 381.4 (M+H$^+$ $^{37}$Cl, 32%).

Example 1.45: Preparation of 2-[(S)-4-(4-Bromo-1-methyl-1H-pyrazole-3-carbonyl)-3-methyl-piperazin-1-yl]-1-(4-fluoro-phenyl)-ethanone (Compound 9)

The title compound was prepared in a similar manner as described in Example 1.40, using 4-bromo-1-methyl-1H-pyrazole-3-carboxylic acid (51.7 mg, 252 µmol) and (S)-1-(4-fluorophenyl)-2-(3-methylpiperazin-1-yl)ethanone dihydrochloride (60.0 mg, 194 µmol) as starting materials, to afford the TFA salt (42 mg) as a solid. $^1$H NMR (Acetonitrile-$d_3$, 400 MHz) δ 1.51 (d, J=7.1 Hz, 3H), 3.17 (s, 4H), 3.55 (s, 3H), 3.89 (s, 3H), 4.61-4.77 (m, 2H), 7.32 (t, J=8.8 Hz, 2H), 7.69 (s, 1H), 8.03 (m, 2H). Exact mass calculated for $C_{18}H_{20}BrFN_4O_2$: 422.1, Found: LCMS m/z (%)=423.3 (M+H$^+$ $^{79}$Br, 100%), 425.3 (M+H$^+$ $^{81}$Br, 97%).

Example 1.46: Preparation of 2-[(S)-4-(4-Chloro-1-methyl-1H-pyrazole-3-carbonyl)-3-methyl-piperazin-1-yl]-1-(4-fluoro-phenyl)-ethanone (Compound 6)

The title compound was prepared in a similar manner as described in Example 1.40, using 4-chloro-1-methyl-1H-pyrazole-3-carboxylic acid (40.5 mg, 252 µmol) and (S)-1-(4-fluorophenyl)-2-(3-methylpiperazin-1-yl)ethanone dihydrochloride (60.0 mg, 194 kµmol) as starting materials, to afford the TFA salt (38 mg) as a solid. $^1$H NMR (Acetonitrile-$d_3$, 400 MHz) δ 1.51 (d, J=7.1 Hz, 3H), 3.16 (s, 4H), 3.55 (s, 3H), 3.87 (s, 3H), 4.61-4.77 (m, 2H), 7.32 (t, J=8.8 Hz, 2H), 7.67 (s, 1H), 8.03 (m, 2H). Exact mass calculated for $C_{18}H_{20}ClFN_4O_2$: 378.1; Found: LCMS m/z (%)=379.4 (M+H$^+$ $^{35}$Cl, 100%), 381.4 (M+H$^+$ $^{37}$Cl, 32%).

Example 1.47: Preparation of 2-[4-(4-Bromo-1-methyl-1H-pyrazole-3-carbonyl)-piperazin-1-yl]-1-(4-fluoro-phenyl)-ethanone (Compound 13)

In a heavy-walled sealed tube, 1-(4-fluorophenyl)-2-(piperazin-1-yl)ethanone dihydrochloride (0.072 g, 0.24 mmol) was dissolved in THF (1.2 mL). 4-Bromo-1-methyl-1H-pyrazole-3-carboxylic acid (0.050 g, 0.24 mmol), O-(7-azabenzotriazol-1-yl)-N,N,N',N'-tetramethyluronium hexafluorophosphate (0.10 g, 0.27 mmol), and triethylamine (0.068 mL, 0.49 mmol) were added. The reaction was heated under microwave irradiation at 100° C. for 10 min. The mixture was concentrated and purified by preparative HPLC. The best fractions were lyophilized to afford the TFA salt of the title compound (0.044 g) as a white solid. $^1$H NMR (DMSO-$d_6$, 400 MHz) δ 3.07-3.33 (m, 2H), 3.50-3.80 (m, 4H), 3.87 (s 3H), 4.07-4.28 (m, 1H), 4.35-4.55 (m, 1H), 4.94-5.18 (m, 2H), 7.48 (t, J=8.7 Hz, 2H), 8.04-8.11 (m, 3H). Exact mass calculated for $C_{17}H_{18}BrFN_4O_2$: 408.1; Found: LCMS m/z (%)=409.4 (M+H$^+$ $^{79}$Br, 100%), 411.4 (M+H$^+$ $^{81}$Br, 98%).

Example 1.48: Preparation of 2-[4-(4-Chloro-1-methyl-1H-pyrazole-3-carbonyl)-piperazin-1-yl]-1-(4-fluorophenyl)-ethanone (Compound 10)

In a heavy-walled sealed tube, 1-(4-fluorophenyl)-2-(piperazin-1-yl)ethanone dihydrochloride (0.37 g, 1.2 mmol) was dissolved in THF (4.9 mL). 4-Chloro-1-methyl-1H-pyrazole-3-carboxylic acid (0.200 g, 1.20 mmol), O-(7-azabenzotriazol-1-yl)-N,N,N',N'-tetramethyluronium hexafluorophosphate (0.52 g, 1.4 mmol), and triethylamine (0.25 mL, 2.5 mmol) were added to the solution. The reaction was heated under microwave irradiation at 100° C. for 10 min. The mixture was concentrated and purified by preparative HPLC. The best fractions were lyophilized to afford the TFA salt of the title compound (0.22 g) as a white solid. $^1$H NMR (DMSO-$d_6$, 400 MHz) δ 3.05-3.60 (m, 4H), 3.86 (s, 3H), 3.80-4.10 (m, 4H), 4.96-5.12 (m, 2H), 7.48 (t, J=8.8 Hz, 2H), 8.04-8.13 (m, 3H). Exact mass calculated for $C_{17}H_{18}ClFN_4O_2$: 364.1; Found: LCMS m/z (%)=365.4 (M+H$^+$ $^{35}$Cl, 100%), 367.4 (M+H$^+$ $^{37}$Cl, 32%).

Example 1.49: Preparation of (4-Chloro-1-methyl-1H-pyrazol-3-yl)-{4-[2-(4-chlorophenyl)-ethyl]-piperazin-1-yl}-methanone (Compound 44)

In a heavy-walled sealed tube, (4-chloro-1-methyl-1H-pyrazol-3-yl)(piperazin-1-yl)methanone dihydrochloride (27 mg, 0.10 mmol) was dissolved in DMF (1.0 mL). 4-Chlorophenethyl bromide (12 mg, 0.083 mmol) and potassium carbonate (35 mg, 2.5 mmol) were added. The reaction was heated under microwave irradiation for 10 min at 100° C. The solids were filtered and the filtrate was purified by preparative HPLC. The best fractions were lyophilized to afford the TFA salt of the title compound (15 mg) as a white solid. $^1$H NMR (DMSO-$d_6$, 400 MHz) δ 2.96-3.03 (m, 2H), 3.03-3.28 (m, 2H), 3.30-3.75 (m, 6H), 3.87 (s 3H), 4.23-4.40 (bs, 1H), 4.46-4.65 (bs, 1H), 7.32 (d, J=8.4 Hz, 2H), 7.43 (d, J=8.3 Hz, 2H), 8.10 (s, 1H). Exact mass calculated for $C_{17}H_{20}Cl_2N_4O$: 366.1; Found: LCMS m/z (%)=367.4 (M+H$^+$ $^{35}$Cl, 100%), 369.4 (M+H$^+$ $^{37}$Cl, 64%).

Example 1.50: Preparation of 2-[4-(4-Chloro-1-methyl-1H-pyrazole-3-carbonyl)-piperazin-1-yl]-1-(4-chlorophenyl)-ethanone (Compound 39)

The title compound was prepared in a similar manner as described in Example 1.49, using (4-chloro-1-methyl-1H-pyrazol-3-yl)(piperazin-1-yl)methanone dihydrochloride (27 mg, 0.10 mmol) and 4-chlorophenacyl bromide (19 mg, 0.083 mmol) as starting materials, to afford the TFA salt (13 mg) as a pale solid. $^1$H NMR (DMSO-$d_6$, 400 MHz) δ 2.90-4.50 (m, 11H), 4.80-5.20 (bs, 2H), 7.72 (d, J=8.5 Hz, 2H), 7.97-8.02 (m, 2H), 8.09 (s, 1H). Exact mass calculated for $C_{17}H_{18}Cl_2N_4O_2$: 380.1; Found: LCMS m/z (%)=381.3 (M+H$^+$ $^{35}$Cl, 100%), 383.4 (M+H$^+$ $^{37}$Cl, 64%).

Example 1.51: Preparation of (4-Chloro-1-methyl-1H-pyrazol-3-yl)-{4-[2-(3-fluorophenyl)-ethyl]-piperazin-1-yl}-methanone (Compound 34)

The title compound was prepared in a similar manner as described in Example 1.49, using (4-chloro-1-methyl-1H-pyrazol-3-yl)(piperazin-1-yl)methanone dihydrochloride (27 mg, 0.10 mmol) and 3-fluorophenethyl bromide (17 mg, 0.083 mmol) as starting materials, to afford the TFA salt (12 mg) as a pale solid. $^1$H NMR (DMSO-$d_6$, 400 MHz) δ 2.99-3.80 (m, 10H), 3.87 (s, 3H), 4.20-4.30 (bs, 1H), 4.45-4.65 (bs, 1H), 7.08-7.20 (m, 3H), 7.40 (q, J=7.8 Hz, 1H), 8.10 (s, 1H). Exact mass calculated for $C_{17}H_{20}ClFN_4O$: 350.1; Found: LCMS m/z (%)=351.2 (M+H$^+$ $^{35}$Cl, 100%), 353.2 (M+H$^+$ $^{37}$Cl, 32%).

Example 1.52: Preparation of 2-[4-(4-Chloro-1-methyl-1H-pyrazole-3-carbonyl)-piperazin-1-yl]-1-(3-fluorophenyl)-ethanone (Compound 29)

The title compound was prepared in a similar manner as described in Example 1.49, using (4-chloro-1-methyl-1H-pyrazol-3-yl)(piperazin-1-yl)methanone dihydrochloride (27 mg, 0.10 mmol) and 2-bromo-1-(3-fluorophenyl)ethanone (18 mg, 0.083 mmol) as starting materials, to afford the TFA salt (3.8 mg) as a pale solid. $^1$H NMR (DMSO-$d_6$, 400 MHz) δ 3.00-3.60 (m, 8H), 3.86 (s, 3H), 4.80-5.20 (bs, 2H), 7.59-7.72 (m, 2H), 7.76-7.82 (m, 1H), 7.84 (d, J=7.6 Hz, 1H), 8.09 (s, 1H). Exact mass calculated for $C_{17}H_{18}ClFN_4O_2$: 364.1; Found: LCMS m/z (%)=365.5 (M+H$^+$ $^{35}$Cl, 100%), 367.5 (M+H$^+$ $^{37}$Cl, 33%).

Example 1.53: Preparation of (4-Chloro-1-methyl-1H-pyrazol-3-yl)-{4-[2-(2-fluorophenyl)-ethyl]-piperazin-1-yl}-methanone (Compound 24)

The title compound was prepared in a similar manner as described in Example 1.49, using (4-chloro-1-methyl-1H-pyrazol-3-yl)(piperazin-1-yl)methanone dihydrochloride (27 mg, 0.10 mmol) and 2-fluorophenethyl bromide (18 mg, 0.083 mmol) as starting materials, to afford the TFA salt (3.9 mg) as a white solid. $^1$H NMR (DMSO-$d_6$, 400 MHz) δ 2.99-3.25 (m, 4H), 3.50-3.80 (m, 6H), 3.87 (s, 3H), 4.25-4.42 (bs, 1H), 4.50-4.68 (bs, 1H), 7.17-7.26 (m, 2H), 7.40-7.31 (m, 2H), 8.10 (s, 1H). Exact mass calculated for $C_{17}H_{20}ClFN_4O$: 350.1, Found: LCMS m/z (%)=351.2 (M+H$^+$ $^{35}$Cl, 100%), 353.2 (M+H$^+$ $^{37}$Cl, 32%).

Example 1.54: Preparation of 2-[4-(4-Bromo-1-methyl-1H-pyrazole-3-carbonyl)-piperazin-1-yl]-1-(2-fluorophenyl)-ethanone (Compound 71)

The title compound was prepared in a similar manner as described in Example 1.49, using (4-bromo-1-methyl-1H-pyrazol-3-yl)-piperazin-1-yl-methanone hydrochloride (31 mg, 0.10 mmol) and 2-bromo-1-(2-fluorophenyl)ethanone (26 mg, 0.12 mmol) as starting materials, to afford the TFA salt (6.1 mg) as a white solid. $^1$H NMR (DMSO-$d_6$, 400 MHz) δ 2.80-3.75 (m, 8H), 3.87 (s, 3H), 4.00-4.60 (m, 1H), 4.70-5.11 (bs, 1H), 7.30-7.51 (m, 2H), 7.68-7.85 (m, 1H), 7.86-8.02 (m, 1H), 8.07 (s, 1H). Exact mass calculated for $C_{17}H_{18}BrFN_4O_2$: 408.1; Found: LCMS m/z (%)=409.4 (M+H$^+$ $^{79}$Br, 100%), 411.4 (M+H$^+$ $^{81}$Br, 98%).

Example 1.55: Preparation of 2-[4-(4-Bromo-1-methyl-1H-pyrazole-3-carbonyl)-piperazin-1-yl]-1-(2-methoxyphenyl)-ethanone (Compound 65)

The title compound was prepared in a similar manner as described in Example 1.49, using (4-bromo-1-methyl-H-pyrazol-3-yl)-piperazin-1-yl-methanone hydrochloride (31 mg, 0.10 mmol) and 2-bromo-1-(2-methoxyphenyl)ethanone (28 mg, 0.12 mmol) as starting materials, to afford the TFA salt (11 mg) as a white solid. $^1$H NMR (DMSO-$d_6$, 400 MHz) δ 3.10-3.70 (m, 6H), 3.88 (s, 3H), 3.95 (s, 3H), 4.10-4.28 (m, 1H), 4.43-4.62 (m, 1H), 4.75-4.95 (m, 2H), 7.09-7.17 (m, 1H), 7.24-7.32 (d, J=8.4 Hz, 1H), 7.65-7.74 (m, 1H), 7.80-7.94 (m, 1H), 8.09 (s, 1H). Exact mass calculated for $C_{18}H_{21}BrN_4O_3$: 420.1; Found: LCMS m/z (%)=421.4 (M+H$^+$ $^{79}$Br, 100%), 423.4 (M+H$^+$ $^{81}$Br, 97%).

Example 1.56: Preparation of (4-Bromo-1-methyl-1H-pyrazol-3-yl)-{4-[2-(3-chlorophenyl)-ethyl]-piperazin-1-yl}-methanone (Compound 60)

The title compound was prepared in a similar manner as described in Example 1.49, using (4-bromo-1-methyl-H-pyrazol-3-yl)-piperazin-1-yl-methanone hydrochloride (31 mg, 0.10 mmol) and 1-(2-bromoethyl)-3-chlorobenzene (26 mg, 0.12 mmol) as starting materials, to afford the TFA salt (15 mg) as a white solid. $^1$H NMR (DMSO-$d_6$, 400 MHz) δ 2.92-3.74 (m, 10H), 3.88 (s, 3H), 4.14-4.27 (bs, 1H), 4.45-4.64 (bs, 1H), 7.26 (d, J=7.3 Hz, 1H), 7.32-7.43 (m, 3H), 8.09 (s, 1H). Exact mass calculated for $C_{17}H_{20}BrClN_4O$: 410.1; Found: LCMS m/z (%)=411.3 (M+H$^+$ $^{79}$Br, 77%), 413.3 (M+H$^+$ $^{81}$Br, 100%).

Example 1.57: Preparation of (4-Bromo-1-methyl-1H-pyrazol-3-yl)-{4-[2-(2-chlorophenyl)-ethyl]-piperazin-1-yl}-methanone (Compound 55)

(4-Bromo-1-methyl-1H-pyrazol-3-yl)-piperazin-1-yl-methanone hydrochloride (31 mg, 0.10 mmol) was dissolved in DMF (1.5 mL). 1-(2-Bromoethyl)-2-chlorobenzene (66 mg, 0.30 mmol) and potassium carbonate (42 mg, 0.30 mmol) were added. The reaction was stirred at 50° C. for 2 h. Potassium carbonate was removed by filtration and the filtrate was purified by preparative HPLC. The best fractions were lyophilized to afford the TFA salt of the title compound (0.041 g) as a pale solid. $^1$H NMR (DMSO-$d_6$, 400 MHz) δ 3.05-3.80 (m, 10H), 3.88 (s, 3H), 4.18-4.39 (bs, 1H), 4.50-4.70 (bs, 1H), 7.29-7.39 (m, 2H), 7.42 (dd, J=2.2, 7.5 Hz, 1H), 7.48 (dd, J=1.4, 7.1 Hz, 1H), 8.09 (s, 1H). Exact mass calculated for $C_{17}H_{20}BrClN_4O$: 410.1; Found: LCMS m/z (%)=411.4 (M+H$^+$ $^{79}$Br, 77%), 413.3 (M+H$^+$ $^{81}$Br, 100%).

Example 1.58: Preparation of (4-Bromo-1-methyl-1H-pyrazol-3-yl)-{(R)-4-[2-(4-fluoro-phenyl)-ethyl]-3-methyl-piperazin-1-yl}-methanone (Compound 75)

4-Bromo-1-methyl-1H-pyrazole-3-carboxylic acid (55.5 mg, 271 µmol) and (R)-1-(4-fluorophenethyl)-2-methylpiperazine (59.8 mg, 269 μmol) were dissolved in DMA (3 mL) and N,N-diisopropylethylamine (50 μL). O-(7-azabenzotriazol-1-yl)-N,N,N',N'-tetramethyluronium hexafluorophosphate (115 mg, 302 μmol) was added and stirring was continued for 2 h. The reaction was purified by preparative HPLC to afford the TFA salt of the title compound (64 mg) as a white solid. Exact mass calculated for $C_{18}H_{22}BrFN_4O$: 408.1; Found: LCMS m/z (%)=409.4 (M+H$^+$ $^{79}$Br, 100%), 411.4 (M+H$^+$ $^{81}$Br, 97%).

Example 1.59: Preparation of (4-Bromo-1,5-dimethyl-1H-pyrazol-3-yl)-{(R)-4-[2-(4-fluoro-phenyl)-ethyl]-3-methyl-piperazin-1-yl}-methanone (Compound 73)

The title compound was prepared in a similar manner as described in Example 1.58, using 4-bromo-1,5-dimethyl-1H-pyrazole-3-carboxylic acid (74 mg, 0.34 mmol) and (R)-1-(4-fluorophenethyl)-2-methylpiperazine (56 mg, 0.25 mmol) as starting materials, to afford the TFA salt (64 mg) as a white solid. Exact mass calculated for $C_{19}H_{24}BrFN_4O$: 422.1, Found: LCMS m/z (%)=423.3 (M+H$^+$ $^{79}$Br, 100%), 425.3 (M+H$^+$ $^{81}$Br, 97%).

Example 1.60: Preparation of (4-Bromo-1-methyl-1H-pyrazol-3-yl)-{(S)-4-[2-(4-fluoro-phenyl)-ethyl]-3-methyl-piperazin-1-yl}-methanone (Compound 58)

The title compound was prepared in a similar manner as described in Example 1.58, using 4-bromo-1-methyl-1H-pyrazole-3-carboxylic acid (70.1 mg, 342 μmol) and (S)-1-(4-fluorophenethyl)-2-methylpiperazine (56.7 mg, 255 μmol) as starting materials, to afford the TFA salt (65 mg) as a white solid. $^1$H NMR (400 MHz, DMSO-d$_6$) δ 1.11-1.46 (m, 3H), 2.85-4.60 (m, 14H), 7.19 (t, J=8.8 Hz, 2H), 7.32-7.43 (m, 2H), 8.10 (s, 1H), 9.99-10.55 (m, 1H). Exact mass calculated for $C_{18}H_{22}BrFN_4O$: 408.1; Found: LCMS m/z (%)=409.4 (M+H$^+$ $^{79}$Br, 100%), 411.4 (M+H$^+$ $^{81}$Br, 97%).

Example 1.61: Preparation of (4-Bromo-1,5-dimethyl-1H-pyrazol-3-yl)-{(S)-4-[2-(4-fluoro-phenyl)-ethyl]-3-methyl-piperazin-1-yl}-methanone (Compound 53)

The title compound was prepared in a similar manner as described in Example 1.58, using 4-bromo-1,5-dimethyl-1H-pyrazole-3-carboxylic acid (66 mg, 301 μmol) and (S)-1-(4-fluorophenethyl)-2-methylpiperazine (59 mg, 265 μmol) as starting materials, to afford the TFA salt (54 mg) as a white solid. $^1$H NMR (DMSO-d$_6$, 400 MHz) δ 1.10-1.47 (m, 3H), 2.28 (s, 3H), 2.82-4.66 (m, 14H), 7.19 (t, J=8.8 Hz, 2H), 7.31-7.41 (m, 2H), 9.92-10.47 (m, 1H). Exact mass calculated for $C_{19}H_{24}BrFN_4O$: 422.1; Found: LCMS m/z (%)=423.3 (M+H$^+$ $^{79}$Br, 100%), 425.3 (M+H$^+$ $^{81}$Br, 97%).

Example 1.62: Preparation of (4-Bromo-1-methyl-1H-pyrazol-3-yl)-{(R)-4-[2-(4-fluoro-phenyl)-ethyl]-2-methyl-piperazin-1-yl}-methanone (Compound 59)

The title compound was prepared in a similar manner as described in Example 1.58, using 4-bromo-1-methyl-1H-pyrazole-3-carboxylic acid (70.7 mg, 345 μmol) and (R)-1-(4-fluorophenethyl)-3-methylpiperazine (64.1 mg, 288 μmol) as starting materials, to afford the TFA salt (68 mg) as a white solid. Exact mass calculated for $C_{18}H_{22}BrFN_4O$: 408.1, Found: LCMS m/z (%)=409.4 (M+H$^+$ $^{79}$Br, 100%), 411.4 (M+H$^+$ $^{81}$Br, 97%).

Example 1.63: Preparation of (4-Bromo-1-methyl-1H-pyrazol-3-yl)-{(S)-4-[2-(4-fluoro-phenyl)-ethyl]-2-methyl-piperazin-1-yl}-methanone (Compound 54)

The title compound was prepared in a similar manner as described in Example 1.58, using 4-bromo-1-methyl-1H-pyrazole-3-carboxylic acid (56.3 mg, 275 μmol) and (S)-1-(4-fluorophenethyl)-3-methylpiperazine (56 mg, 252 μmol) as starting materials, to afford the TFA salt (51 mg) as a white solid. $^1$H NMR (DMSO-d$_6$, 400 MHz) δ 1.36 (d, J=7.3 Hz, 3H), 2.93-5.02 (m, 14H), 7.19 (t, J=8.8 Hz, 2H), 7.27-7.35 (m, 2H), 8.09 (s, 1H), 9.67-9.99 (m, 1H). Exact mass calculated for $C_{18}H_{22}BrFN_4O$: 408.1; Found: LCMS m/z (%)=409.4 (M+H$^+$ $^{79}$Br, 100%), 411.4 (M+H$^+$ $^{81}$Br, 97%).

Example 1.64: Preparation of (4-Bromo-1-methyl-1H-pyrazol-3-yl)-(4-phenethyl-piperazin-1-yl)-methanone (Compound 43)

To a mixture of 1-phenethylpiperazine (0.050 g, 263 μmol), 4-bromo-1-methyl-1H-pyrazole-3-carboxylic acid (64.6 mg, 315 μmol) and O-(7-azabenzotriazol-1-yl)-N,N,N',N'-tetramethyluronium hexafluorophosphate (120 mg, 315 μmol) in DMA (2 mL), N,N-diisopropylethylamine (138 μl, 788 μmol) was added. The reaction mixture was heated at 120° C. for 20 min under microwave irradiation in a heavy-walled sealed tube and purified by preparative HPLC. The corresponding fractions were collected, and lyophilized to afford the TFA salt of the title compound (51 mg) as an off-white solid. $^1$H NMR (DMSO-d$_6$, 400 MHz) δ 3.02-2.91 (m, 2H), 3.30-3.02 (m, 4H), 3.80-3.36 (m, 4H), 3.88 (s, 3H), 4.34-4.21 (m, 1H), 4.62-4.51 (m, 1H), 7.31-7.25 (m, 3H), 7.38-7.33 (m, 2H), 8.10 (s, 1H). Exact mass calculated for $C_{17}H_{21}BrN_4O$: 376.1; Found: LCMS m/z (%)=377.4 (M+H$^+$ $^{79}$Br, 100%), 379.4 (M+H$^+$ $^{81}$Br, 97%).

Example 1.65: Preparation of (4-Bromo-1-methyl-1H-pyrazol-3-yl)-{4-[2-(3-fluoro-phenyl)-ethyl]-piperazin-1-yl}-methanone (Compound 38)

A mixture of (4-bromo-1-methyl-1H-pyrazol-3-yl)(piperazin-1-yl)methanone hydrochloride (0.040 g, 146 μmol), 1-(2-bromoethyl)-3-fluorobenzene (35.7 mg, 176 μmol) and potassium carbonate (60.7 mg, 439 μmol) in acetonitrile (2 mL) was heated at 120° C. for 20 min under microwave irradiation in a heavy-walled sealed tube and purified by preparative HPLC. The corresponding fractions were collected, and lyophilized to afford the TFA salt of the title compound (12.6 mg) as a white solid. Exact mass calculated for $Cl_7H_{20}BrFN_4O$: 394.1; Found: LCMS m/z (%)=395.3 (M+H$^+$ $^{79}$Br, 100%), 397.3 (M+H$^+$ $^{81}$Br, 97%).

Example 1.66: Preparation of 2-[4-(4-Bromo-1-methyl-1H-pyrazole-3-carbonyl)-piperazin-1-yl]-1-(3-fluoro-phenyl)-ethanone (Compound 14)

A mixture of (4-bromo-1-methyl-1H-pyrazol-3-yl)(piperazin-1-yl)methanone hydrochloride (0.040 g, 146 μmol), 2-bromo-1-(3-fluorophenyl)ethanone (35.0 mg, 161 μmol) and potassium carbonate (60.7 mg, 439 μmol) in acetonitrile was stirred at room temperature for 30 min. The reaction mixture was purified by preparative HPLC. The corresponding fractions were collected and lyophilized to afford the TFA salt of the title compound (16 mg) as a white solid. Exact mass calculated for $C_{17}H_{18}BrFN_4O$: 408.1; Found: LCMS m/z (%)=409.4 (M+H$^+$ $^{79}$Br, 100%), 411.4 (M+H$^+$ $^{81}$Br, 97%).

Example 1.67: Preparation of (4-Bromo-1-methyl-1H-pyrazol-3-yl)-{4-[2-(2-fluoro-phenyl)-ethyl]-piperazin-1-yl}-methanone (Compound 8)

A mixture of (4-bromo-1-methyl-1H-pyrazol-3-yl)(piperazin-1-yl)methanone hydrochloride (40.0 mg, 147 µmol), 1-(2-bromoethyl)-2-fluorobenzene (31 µL, 220 iµmol) and potassium carbonate (60.7 mg, 439 µmol) in acetonitrile (2 mL) was heated at 150° C. for 20 min under microwave irradiation in a heavy-walled sealed tube. Potassium carbonate was filtered off. The filtrate was purified by preparative HPLC. The corresponding fractions were collected, and lyophilized to afford the TFA salt of the title compound (17 mg) as a white solid. Exact mass calculated for $C_{17}H_{20}BrFN_4O$: 394.1; Found: LCMS m/z (%)=395.4 (M+H$^+$ $^{79}$Br, 100%), 397.4 (M+H$^+$ $^{81}$Br, 97%).

Example 1.68: Preparation of 5-{2-[4-(4-Bromo-1-methyl-1H-pyrazole-3-carbonyl)-piperazin-1-yl]-ethyl}-6-chloro-1,3-dihydro-indol-2-one (Compound 5)

A mixture of (4-bromo-1-methyl-1H-pyrazol-3-yl)(piperazin-1-yl)methanone hydrochloride (40.0 mg, 146 µmol), 6-chloro-5-(2-chloroethyl)indolin-2-one (40.4 mg, 176 µmol), potassium iodide (24.3 mg, 146 µmol) and potassium carbonate (40.5 mg, 293 µmol) in acetonitrile (2 mL) was heated at 160° C. for 20 min under microwave irradiation in a heavy-walled sealed tube. The reaction mixture was purified by preparative HPLC. The corresponding fractions were collected and lyophilized to afford the TFA salt of the title compound (25 mg) as a white solid. Exact mass calculated for $C_{19}H_{21}BrClN_5O_2$: 465.1; Found: LCMS m/z (%)=466.5 (M+H$^+$ $^{79}$Br, 77%), 468.5 (M+H$^+$ $^{81}$Br, 100%).

Example 1.69: Preparation of (4-Bromo-1-methyl-1H-pyrazol-3-yl)-{4-[2-(4-chloro-phenyl)-ethyl]-piperazin-1-yl}-methanone (Compound 2)

A mixture of (4-bromo-1-methyl-1H-pyrazol-3-yl)(piperazin-1-yl)methanone hydrochloride (40.0 mg, 0.146 mmol), 1-(2-bromoethyl)-4-chlorobenzene (26 µL, 0.18 µmol) and potassium carbonate (61 mg, 0.44 gµmol) in acetonitrile (2 mL) was heated at 150° C. for 20 min under microwave irradiation in a heavy-walled sealed tube. The reaction mixture was purified by preparative HPLC. The corresponding fractions were collected, and lyophilized to afford the TFA salt of the title compound (7.9 mg) as a white solid. Exact mass calculated for $C_{17}H_{20}BrClN_4O$: 410.1; Found: LCMS m/z (%)=411.1 (M+H$^+$ $^{79}$Br, 77%), 413.1 (M+H$^+$ $^{81}$Br, 100%).

Example 1.70: Preparation of 2-[4-(4-Bromo-1-methyl-1H-pyrazole-3-carbonyl)-piperazin-1-yl]-1-(4-chloro-phenyl)-ethanone (Compound 70)

A mixture of (4-bromo-1-methyl-1H-pyrazol-3-yl)(piperazin-1-yl)methanone hydrochloride (40.0 mg, 0.146 mmol), 2-bromo-1-(4-chlorophenyl)ethanone (37.6 mg, 0.161 mmol) and potassium carbonate (60.7 mg, 0.439 mmol) in acetonitrile (2 mL) was stirred at room temperature for 30 min. The reaction mixture was purified by preparative HPLC. The corresponding fractions were collected, and lyophilized to afford the TFA salt of the title compound (41.8 mg) as a white solid. Exact mass calculated for $C_{17}H_{18}BrClN_4O_2$: 424.0; Found: LCMS m/z (%)=425.4 (M+H$^+$ $^{79}$Br, 77%), 427.4 (M+H$^+$ $^{81}$Br, 100%).

Example 1.71: Preparation of 2-[4-(4-Bromo-1-methyl-1H-pyrazole-3-carbonyl)-piperazin-1-yl]-1-naphthalen-2-yl-ethanone (Compound 64)

A mixture of (4-bromo-1-methyl-1H-pyrazol-3-yl)(piperazin-1-yl)methanone hydrochloride (40.0 mg, 146 µmol), 2-bromo-1-(naphthalen-2-yl)ethanone (40.1 mg, 161 µmol) and potassium carbonate (60.7 mg, 439 µmol) in acetonitrile (2 mL) was stirred at room temperature for 30 min. The reaction mixture was purified by preparative HPLC. The corresponding fractions were collected, and lyophilized to afford the TFA salt of the title compound (33.7 mg) as a white solid. Exact mass calculated for $C_{21}H_{21}BrN_4O_2$: 440.1; Found: LCMS m/z (%)=441.4 (M+H$^+$ $^{79}$Br, 77%), 443.4 (M+H$^+$ $^{81}$Br, 100%).

Example 1.72: Preparation of 5-{2-[4-(4-Bromo-1-methyl-1H-pyrazole-3-carbonyl)-piperazin-1-yl]-acetyl}-6-chloro-1,3-dihydro-indol-2-one (Compound 49)

A mixture of (4-bromo-1-methyl-1H-pyrazol-3-yl)(piperazin-1-yl)methanone hydrochloride (40.0 mg, 146 µmol), 6-chloro-5-(2-chloroacetyl)indolin-2-one (42.9 mg, 176 µmol), potassium iodide (24.3 mg, 146 µmol) and potassium carbonate (40.5 mg, 293 µmol) in acetonitrile (2 mL) was stirred at room temperature for 30 min. The reaction mixture was purified by preparative HPLC. The corresponding fractions were collected, and lyophilized to afford the TFA salt of the title compound (10.6 mg) as a white solid. Exact mass calculated for $C_{19}H_{19}BrClN_5O_2$: 479.0; Found: LCMS m/z (%)=480.3 (M+H$^+$ $^{79}$Br, 77%), 482.3 (M+H$^+$ $^{81}$Br, 100%).

Example 1.73: Preparation of 1-(4-Fluoro-phenyl)-2-[4-(1-methyl-1H-pyrazole-3-carbonyl)-piperazin-1-yl]-ethanone (Compound 74)

To a mixture of 1-(4-fluorophenyl)-2-(piperazin-1-yl)ethanone (50.0 mg, 225 µmol), 1-methyl-1H-pyrazole-3-carboxylic acid (34.0 mg, 270 µmol) and O-(7-azabenzotriazol-1-yl)-N,N,N',N'-tetramethyluronium hexafluorophosphate (103 mg, 270 µmol) in DMA (2 mL), N,N-diisopropylethylamine (118 µL, 675 jµmol) was added. The reaction mixture was heated at 120° C. for 20 min under microwave irradiation in a heavy-walled sealed tube. The reaction mixture was purified by preparative HPLC. The corresponding fractions were collected, and lyophilized to afford the TFA salt of the title compound (53.3 mg) as an off-white solid. Exact mass calculated for $C_{17}H_{19}FN_4O_2$: 330.2; Found: LCMS m/z=331.4 (M+H$^+$).

Example 1.74: Preparation of 1-(4-Fluoro-phenyl)-2-[4-(2-methyl-5-phenyl-2H-pyrazole-3-carbonyl)-piperazin-1-yl]-ethanone (Compound 3)

To a mixture of 1-(4-fluorophenyl)-2-(piperazin-1-yl)ethanone dihydrochloride (59.0 mg, 0.200 mmol) and 1-methyl-3-phenyl-1H-pyrazole-5-carbonyl chloride (46.3 mg, 0.210 mmol) in DCM (2 mL), N,N-diisopropylethylamine (105 µL, 0.600 mmol) was added. The reaction mixture was stirred at room temperature overnight, concentrated and purified by preparative HPLC. The corresponding fractions were collected, and lyophilized to afford the TFA salt of the title compound (76.8 mg) as a white solid. Exact mass calculated for $C_{23}H_{23}FN_4O_2$: 406.2; Found: LCMS m/z=407.4 (M+H$^+$).

Example 1.75: Preparation of 1-(4-Fluoro-phenyl)-2-[4-(1-methyl-5-phenyl-1H-pyrazole-3-carbonyl)-piperazin-1-yl]-ethanone (Compound 72)

A mixture of 1-(4-fluorophenyl)-2-(piperazin-1-yl)ethanone dihydrochloride (59.0 mg, 0.200 mmol) and 1-methyl-5-phenyl-1H-pyrazole-3-carbonyl chloride (46.3 mg, 0.210 mmol) and N,N-diisopropylethylamine (105 µL, 0.600 mmol) in DCM (2 mL) was stirred at room temperature overnight, concentrated and purified by preparative HPLC. The corresponding fractions were collected, and lyophilized to afford the TFA salt of the title compound (77.3 mg) as a white solid. Exact mass calculated for $C_{23}H_{23}FN_4O_2$: 406.2; Found: LCMS m/z=407.5 (M+H$^+$).

Example 1.76: Preparation of 1-(4-Fluoro-phenyl)-2-[4-(5-furan-2-yl-1-methyl-1H-pyrazole-3-carbonyl)-piperazin-1-yl]-ethanone (Compound 66)

A mixture of 1-(4-fluorophenyl)-2-(piperazin-1-yl)ethanone dihydrochloride (59.0 mg, 0.20 mmol), 5-(furan-2-yl)-1-methyl-1H-pyrazole-3-carbonyl chloride (44.2 mg, 0.210 mmol) and N,N-diisopropylethylamine (105 µL, 0.600 mmol) in DCM (1.5 mL) was added. The reaction mixture was stirred at room temperature overnight, concentrated and purified by preparative HPLC. The corresponding fractions were collected, and lyophilized to afford the TFA salt of the title compound (65.7 mg) as a white solid. Exact mass calculated for $C_{21}H_{21}FN_4O_3$: 396.2; Found: LCMS m/z=397.3 (M+H$^+$).

Example 1.77: Preparation of (4-Chloro-1-methyl-1H-pyrazol-3-yl)-{4-[2-(4-fluoro-phenyl)-ethyl]-piperazin-1-yl}-methanone (Compound 21)

A mixture of 4-chloro-1-methyl-1H-pyrazole-3-carboxylic acid (40 mg, 0.25 mmol), 1-[2-(4-fluoro-phenyl)-ethyl]-piperazine hydrochloride (61 mg, 0.25 mmol), O-(7-azabenzotriazol-1-yl)-N,N,N',N'-tetramethyluronium hexafluorophosphate (114 mg, 0.3 mmol) and triethylamine (0.2 mL) in DMF (1.5 mL) was heated in microwave at 100° C. for 10 min. The crude mixture was purified by HPLC to afford the TFA salt of the title compound (78 mg) as a yellow solid. $^1$H NMR (Acetonitrile-d$_3$, 400 MHz) δ 3.09-3.15 (m, 2H), 3.32-3.36 (m, 4H), 3.51-3.73 (m, 4H), 3.86-3.94 (m, 5H), 7.13-7.17 (m, 2H), 7.33-7.36 (m, 2H), 7.71 (s, 1H). Exact mass calculated for $C_{17}H_{20}ClFN_4O$: 350.1; Found: LCMS m/z (%)=351.1 (M+H$^+$ $^{35}$Cl, 100%), 353.1 (M+H$^+$ $^{37}$Cl, 32%).

Example 1.78: Preparation of (4-Chloro-1-ethyl-1H-pyrazol-3-yl)-{4-[2-(4-fluoro-phenyl)-ethyl]-piperazin-1-yl}-methanone (Compound 16)

The title compound was prepared in a similar manner as described in Example 1.77, using 4-chloro-1-ethyl-1H-pyrazole-3-carboxylic acid (44 mg, 0.25 mmol) to afford the TFA salt (47 mg) as a white solid. $^1$H NMR (Acetonitrile-d$_3$, 400 MHz) δ 1.48 (t, J=8.0 Hz, 3H), 2.80-3.00 (m, 4H), 3.09-3.13 (m, 4H), 3.32-3.36 (m, 2H), 3.50-3.70 (m, 2H), 4.20 (q, J=8.0 Hz, 2H), 7.13-7.17 (m, 2H), 7.33-7.36 (m, 2H), 7.76 (s, 1H). Exact mass calculated for $C_{18}H_{22}ClFN_4O$: 364.2; Found: LCMS m/z (%)=365.1 (M+H$^+$ $^{35}$Cl, 100%), 367.1 (M+H$^+$ $^{37}$Cl, 32%).

Example 1.79: Preparation of (4-Bromo-1-methyl-1H-pyrazol-3-yl)-{4-[2-(4-methoxy-phenyl)-ethyl]-piperazin-1-yl}-methanone (Compound 22)

Step A: Preparation of Intermediate 4-(4-Bromo-1-methyl-1H-pyrazole-3-carbonyl)-piperazine-1-carboxylic Acid tert-Butyl Ester A mixture of 4-bromo-1-methyl-1H-pyrazole-3-carboxylic acid (500 mg, 2.44 mmol), 1-N-Boc piperazine (454 mg, 2.44 mmol), O-(7-azabenzotriazol-1-yl)-N,N,N',N'-tetramethyluronium hexafluorophosphate (1.11 g, 2.92 mmol) and triethylamine (1.0 mL) in THF (3 mL) was heated in microwave at 100° C. for 5 min. The crude was purified by HPLC to afford the TFA salt of the title compound (820 mg) as an off-white solid. $^1$H NMR (Acetonitrile-d$_3$, 400 MHz) δ 1.49 (s, 9H), 3.43-3.46 (m, 2H), 3.50-3.53 (m, 4H), 3.68-3.70 (m, 2H), 3.91 (s, 3H), 7.69 (s, 1H). Exact mass calculated for $C_{14}H_{21}BrN_4O_3$: 372.1; Found: LCMS m/z (%)=373.1 (M+H$^+$ $^{79}$Br, 100%), 375.1 (M+H$^+$ $^{81}$Br, 97%).

Step B: Preparation of Intermediate (4-Bromo-1-methyl-1H-pyrazol-3-yl)-piperazin-1-yl-methanone 4-(4-Bromo-1-methyl-1H-pyrazole-3-carbonyl)-piperazine-1-carboxylic acid tert-butyl ester (800 mg, 2.14 mmol) from Step A and HCl in dioxane (4 N, 5.36 mL) was stirred at room temperature for 1 h. The solvent was removed under reduced pressure to afford the hydrochloride salt of the title compound (585 mg) as a light yellow solid. $^1$HNMR (Acetonitrile-d$_3$, 400 MHz) δ 3.20-3.26 (m, 4H), 3.92 (s, 3H), 3.98-4.05 (m, 4H), 7.71 (s, 1H), 9.40-9.50 (bs, 2H). Exact mass calculated for $C_9H_{13}BrN_4O$: 272.0; Found: LCMS m/z (%)=273.0 (M+H$^+$ $^{79}$Br, 100%), 275.0 (M+H$^+$ $^{81}$Br, 97%).

Step C: Preparation of (4-Bromo-1-methyl-1H-pyrazol-3-yl)-{4-[2-(4-methoxy-phenyl)-ethyl]-piperazin-1-yl}-methanone(Compound 22)

A mixture of (4-bromo-1-methyl-1H-pyrazol-3-yl)-piperazin-1-yl-methanone hydrochloride (46.4 mg, 0.15 mmol), 1-(2-bromo-ethyl)-4-methoxy-benzene (35.5 mg, 0.165 mmol), potassium carbonate (41.4 mg, 0.3 mmol) and sodium iodide (11 mg, 0.075 mmol) in acetonitrile (1.5 mL) was heated at 100° C. under microwave irradiation for 20 min. The crude mixture was purified by HPLC to afford the TFA salt of the title compound (45 mg) as a white solid. $^1$H NMR (Acetonitrile-d$_3$, 400 MHz) δ 3.05-3.07 (m, 4H), 3.30-3.35 (m, 4H), 3.55-3.66 (m, 4H), 3.82 (s, 3H), 3.92 (s, 3H), 6.94-6.97 (m, 2H), 7.22-7.26 (m, 2H), 7.72 (s, 1H). Exact mass calculated for $C_{18}H_{23}BrN_4O_2$: 406.1; Found: LCMS m/z (%)=407.4 (M+H$^+$ $^{79}$Br, 100%), 409.4 (M+H$^+$ $^{81}$Br, 97%).

Example 1.80: Preparation of 2-[4-(4-Bromo-1-methyl-1H-pyrazole-3-carbonyl)-piperazin-1-yl]-1-(2,4-difluoro-phenyl)-ethanone (Compound 81)

The title compound was prepared in a similar manner as described in Example 1.79, using 2-bromo-1-(2,4-difluoro-phenyl)-ethanone (38.7 mg, 0.165 mmol) to afford the TFA salt (38 mg) as a white solid. $^1$H NMR (Acetonitrile-$d_3$, 400 MHz) δ 3.41-3.52 (m, 4H), 3.92 (s, 3H), 4.02-4.15 (m, 4H), 4.68 (d, 2H), 7.18-7.25 (m, 2H), 7.73 (s, 1H), 8.08-8.14 (m, 1H). Exact mass calculated for $C_{17}H_{17}BrF_2N_4O_2$: 426.1; Found: LCMS m/z (%)=427.2 (M+H$^+$ $^{79}$Br, 100%), 429.2 (M+H$^+$ $^{81}$Br, 97%).

Example 1.81: Preparation of (4-Chloro-1-methyl-1H-pyrazol-3-yl)-{4-[2-(4-fluoro-phenyl)-propyl]-piperazin-1-yl}-methanone (Compound 69)

To (4-chloro-1-methyl-1H-pyrazol-3-yl)-{4-[2-(4-fluoro-phenyl)-ethyl]-piperazin-1-yl}-methanone (45 mg, 0.128 mmol) in THF was added n-BuLi (1.6 M, 0.4 mL) at −78° C. The mixture was stirred at this temperature for 1 h. Then, methyl iodide (182 mg, 1.28 mmol) was added. The mixture was warmed up to room temperature and stirred overnight. The reaction was quenched with $H_2O$ and the mixture was concentrated under reduced pressure. The crude product was purified by HPLC to afford the TFA salt of the title compound as a white solid. Exact mass calculated for $C_{18}H_{22}ClFN_4O$: 364.2; Found: LCMS m/z (%)=365.5 (M+H$^+$ $^{35}$Cl, 100%), 367.5 (M+H$^+$ $^{37}$Cl, 32%).

Example 1.82: Preparation of (4-Chloro-1-methyl-1H-pyrazol-3-yl)-{4-[2-(4-fluoro-phenyl)-2-methyl-propyl]-piperazin-1-yl}-methanone (Compound 63)

The title compound was prepared in a similar manner as described in Example 1.81 to afford the TFA salt as a white solid. Exact mass calculated for $C_{19}H_{24}ClFN_4O$: 378.2; Found: LCMS m/z (%)=379.4 (M+H$^+$ $^{35}$Cl, 100%), 381.4 (M+H$^+$ $^{37}$Cl, 32%).

Example 1.83: Preparation of {4-[2-(4-Fluoro-phenyl)-ethyl]-piperazin-1-yl}-(1-methyl-5-trifluoromethyl-1H-pyrazol-3-yl)-methanone (Compound 83)

The title compound was prepared in a similar manner as described in Example 1.77, using 1-methyl-5-trifluoromethyl-1H-pyrazole-3-carboxylic acid (58 mg, 0.3 mmol) to afford the TFA salt (100 mg) as a white solid. $^1$H NMR (Acetonitrile-$d_3$, 400 MHz) δ 3.06-3.15 (m, 4H), 3.31-3.38 (m, 4H), 3.44-3.70 (m, 2H), 4.04 (s, 3H), 4.73 (s, 1H), 5.04 (s, 1H), 7.11-7.20 (m, 3H), 7.31-7.40 (m, 2H). Exact mass calculated for $C_{18}H_{20}F_4N_4O$: 384.2; Found: LCMS m/z=385.2 (M+H$^+$).

Example 1.84: Preparation of (4-Bromo-1-methyl-1H-pyrazol-3-yl)-{4-[2-(2,4-difluoro-phenyl)-ethyl]-piperazin-1-yl}-methanone (Compound 84)

Step A: Preparation of tert-Butyl 4-(2-(2,4-Difluorophenyl)acetyl)piperazine-1-carboxylate 2-(2,4-Difluorophenyl)acetic acid (5.00 g, 29.1 mmol), 1H-benzo[d][1,2,3]triazol-1-ol (4.46 g, 29.1 mmol), N-ethyl-N-(3-dimethylaminopropyl)carbodiimide hydrochloride (5.57 g, 29.1 mmol) and triethylamine (4.05 mL, 29.1 mmol) were stirred in DCM (30 mL) for 15 min. tert-Butyl piperazine-1-carboxylate (2.71 g, 14.5 mmol) was added and the mixture was stirred at room temperature for 8 h. The reaction was diluted with DCM (10 mL) and washed with 1 N NaOH (5 mL), followed by 1 M citric acid (5 mL). The organic extracts were dried over $Na_2SO_4$, filtered and concentrated to afford an oil that was purified by RP-HPLC. The best fractions were lyophilized to afford material that was neutralized with $NaHCO_3$ (75 mL), and extracted with EtOAc (2×200 mL). The organic extracts were dried over $Na_2SO_4$, filtered, and concentrated to afford the title compound (1.68 g) as a yellow solid. $^1$H NMR (DMSO-$d_6$, 400 MHz) δ 1.42 (s, 9H), 3.25-3.39 (m, 4H), 3.42-3.48 (m, 2H), 3.49-3.56 (m, 2H), 3.74 (s, 2H), 7.02 (dt, J=2.7, 8.5 Hz, 1H), 7.18 (dt, J=2.6, 9.7 Hz, 1H), 7.25-7.33 (m, 1H). Exact mass calculated for $C_{17}H_{22}F_2N_2O_3$: 340.2; Found: LCMS m/z=341.3 (M+H$^+$).

Step B: Preparation of tert-Butyl 4-(2,4-Difluorophenethyl)piperazine-1-carboxylate tert-Butyl 4-(2-(2,4-difluorophenyl)acetyl)piperazine-1-carboxylate (1.12 g, 3.30 mmol) was dissolved in THF (8.5 mL) and borane-tetrahydrofuran complex (1.0 M, 15.8 mL, 15.8 mmol) was added. The reaction was refluxed at 66° C. The reaction was quenched slowly with methanol (0.4 mL) dropwise. Then, 0.5 M HCl (10.0 mL) was added, and the mixture was extracted with EtOAc (2×100 mL). The organic extracts were dried over $Na_2SO_4$, filtered, and concentrated to give a residue that was purified by RP-HPLC. The best fractions were added to $NaHCO_3$ (20 mL) and extracted with EtOAc (2×100 mL). The organic extracts were dried over $Na_2SO_4$, filtered, and concentrated to yield the title compound (1.08 g) as a white solid. $^1$H NMR (DMSO-$d_6$, 400 MHz) δ 1.41 (s 9H), 2.80-2.96 (m, 6H), 3.10-3.03 (m, 2H), 3.50-3.60 (m, 4H), 7.06 (dt, J=2.6, 8.5 Hz, 1H), 7.22 (dt, J=2.6, 9.6 Hz, 1H), 7.38-7.46 (m, 1H). Exact mass calculated for $C_{17}H_{24}F_2N_2O_2$: 326.2; Found: LCMS m/z=327.1 (M+H$^+$).

Step C: Preparation of 1-(2,4-Difluorophenethyl)piperazine.

tert-Butyl 4-(2,4-difluorophenethyl)piperazine-1-carboxylate (0.853 g, 2.61 mmol) was dissolved in 4 M HCl in dioxane (10.0 mL) and stirred for 1 hour. The reaction was concentrated to afford the dihydrochloride salt of the title compound (0.718 g, 92% yield) as a pale solid. $^1$H NMR (DMSO-$d_6$, 400 MHz) δ 2.95-3.75 (m, 12H), 6.03-6.80 (bs, 1H), 7.04-7.12 (m, 1H), 7.24 (dt, J=2.6, 9.6 Hz, 1H), 7.39-7.50 (m, 1H). Exact mass calculated for $Cl_2H_6F_2N_2$: 226.1; Found: LCMS m/z=227.2 (M+H$^+$).

Step D: Preparation of (4-Bromo-1-methyl-1H-pyrazol-3-yl)-{4-[2-(2,4-difluoro-phenyl)-ethyl]-piperazin-1-yl}-methanone (Compound 84)

In a heavy-walled sealed tube, 4-bromo-1-methyl-1H-pyrazole-3-carboxylic acid (0.0194 g, 0.0583 mmol), 1-(2,4-difluorophenethyl)piperazine (0.0145 g, 0.0641 mmol), O-(7-azabenzotriazol-1-yl)-N,N,N',N'-tetramethyluronium hexafluorophosphate (0.0244 g, 0.0641 mmol), and triethylamine (0.0162 mL, 0.117 mmol) were combined in THF (0.5 mL). The reaction mixture was heated at 100° C. for 10 min under microwave irradiation. The reaction mixture was concentrated and then purified by RP-HPLC. The best fractions were lyophilized to afford the TFA salt of the title compound (0.015 g) as a yellow solid. $^1$H NMR (DMSO-$d_6$, 400 MHz) δ 2.90-3.80 (m, 10H), 3.87 (s, 3H), 4.18-4.40 (bs, 1H), 4.45-4.69 (bs, 1H), 7.07-7.16 (m, 1H), 7.23-7.33 (m, 1H), 7.39-7.47 (m, 1H), 8.09 (s, 1H). Exact mass calculated for $C_{17}H_{19}BrF_2N_4O$: 412.1; Found: LCMS m/z (%)=413.1 (M+H$^+$ $^{79}$Br, 100%), 415.1 (M+H$^+$ $^{81}$Br, 98%).

Example 1.85: Preparation of (4-Chloro-1-methyl-1H-pyrazol-3-yl)-{4-[2-(2,4-difluoro-phenyl)-ethyl]-piperazin-1-yl}-methanone (Compound 85)

To a mixture of 4-chloro-1-methyl-1H-pyrazole-3-carboxylic acid (6.81 mg, 42.4 μmol), O-(7-azabenzotriazol- 1-yl)-N,N,N',N'-tetramethyluronium hexafluorophosphate (16.1 mg, 42.4 µmol) and N,N-Diisopropylethylamine (18.5 µl, 106 µmol) in DMA (0.5 mL) was added a solution of 1-(2,4-difluorophenethyl)piperazine (80.0 mg, 35.4 µmol) in DMA (0.5 mL). The reaction mixture was heated at 120° C. for 20 min under microwave irradiation in a heavy-walled sealed tube. The reaction mixture was concentrated and then purified by RP-HPLC. The best fractions were lyophilized to afford the TFA salt of the title compound (5.60 mg) as a white solid. Exact mass calculated for $C_{17}H_{19}ClF_2N_4O$: 368.1; Found: LCMS m/z (%)=369.3 (M+H$^+$ $^{35}$Cl, 100%), 371.3 (M+H$^+$ $^{37}$Cl, 32%).

Example 2: Receptor Expression

A. pCMV

Although a variety of expression vectors are available to those in the art, it is preferred that the vector utilized be pCMV. This vector was deposited with the American Type Culture Collection (ATCC) on Oct. 13, 1998 (10801 University Blvd., Manassas, Va. 20110-2209 USA) under the provisions of the Budapest Treaty for the International Recognition of the Deposit of Microorganisms for the Purpose of Patent Procedure. The DNA was tested by the ATCC and determined to be viable. The ATCC has assigned the following deposit number to pCMV: ATCC #203351.

B. Transfection Procedure

For the IP accumulation assay (Example 6), HEK293 cells were transfected while for the DOI binding assay (Example 3) COS7 cells were transfected. Several protocols well known in the art can be used to transfect cells. The following protocol is representative of the transfection procedures used herein for COS7 or HEK293 cells.

On day one, COS-7 cells or HEK293 cells were plated onto 24-well plates, usually 1×10$^5$ cells/well or 2×10$^5$ cells/well respectively. On day two, the cells were transfected by first mixing 0.25 µg cDNA in 50 µl serum-free DMEM/well and then 2 µl lipofectamine in 50 µl serum-free DMEM/well. The solutions (transfection media) were gently mixed and incubated for 15-30 minutes at room temperature. The cells were washed with 0.5 mL PBS and then 400 µl of serum free medium was mixed with the transfection media and added to the cells. The cells were then incubated for 3-4 hours at 37° C./5% CO$_2$. Then the transfection medium was removed and replaced with 1 mL/well of regular growth medium.

For HEK293 cells, on day one, 13×10$^6$ cells per 150 mm plate were plated out. On day two, 2 mL of serum OptimemI (Invitrogen Corporation) was added per plate followed by addition of 60 µL of lipofectamine and 16 µg of cDNA. Note that lipofectamine must be added to the OptimemI and mixed well before addition of cDNA. While complexes between lipofectamine and the cDNA are forming, medium was carefully aspirated and cells were gently rinsed with 5 mL of OptimemI medium followed by careful aspiration. Then 12 mL of OptimemI was added to each plate and 2 mL of transfection solution was added followed by a 5 hour incubation at 37° C. in a 5% CO$_2$ incubator. Plates were then carefully aspirated and 25 mL of Complete Media were added to each plate and cells were then incubated until used.

Example 3: Binding Assays

Compounds of the invention were tested for their ability to bind to a 5-HT$_{2A}$ serotonin receptor clone membrane preparation using a radioligand binding assay. Briefly, COS cells were transiently transfected with a pCMV expression vector containing a human 5-HT$_{2A}$ receptor (for the sequence of the receptor see U.S. Pat. No. 6,541,209, SEQ ID NO:24).

A. Preparation of Crude Membrane Preparations for Radioligand Binding Assays.

COS7 cells transfected with recombinant human 5-HT$_{2A}$ serotonin receptors were cultured for 48 h post transfection, collected, washed with ice-cold phosphate buffered saline, pH 7.4 (PBS), and then centrifuged at 48,000 g for 20 min at 4° C. The cell pellet was then resuspended in wash buffer containing 20 mM HEPES pH 7.4 and 0.1 mM EDTA, homogenized on ice using a Brinkman polytron, and recentrifuged at 48,000 g for 20 min at 4° C. The resultant pellet was then resuspended in 20 mM HEPES, pH 7.4, homogenized on ice, and centrifuged (48,000 g for 20 min at 4° C.). Crude membrane pellets were stored at −80° C. until used for radioligand binding assays.

B. [$^{125}$I]DOI Radioligand Binding Assay.

Radioligand binding assays for human 5-HT$_{2A}$ serotonin receptor was conducted using the 5-HT$_2$ agonist [$^{125}$I]DOI as radioligand. To define nonspecific binding, 10 µM DOI was used for all assays. For competitive binding studies, 0.5 nM [$^{125}$I]DOI was used and compounds were assayed over a range of 0.01 nM to 10 µM. Assays were conducted in a total volume of 200 µl in 96-well Perkin Elmer GF/C filter plates in assay buffer (50 mM Tris-HCl, pH 7.4, 0.5 mM EDTA, 5 mM MgCl$_2$, and 10 µM pargyline). Assay incubations were performed for 60 min at room temperature and were terminated by rapid filtration under vacuum pressure of the reaction mixture over Whatman GF/C glass fiber filters presoaked in 0.5% PEI using a Brandell cell harvester. Filters were then washed several times with ice-cold wash buffer (50 mM Tris-HCl, pH 7.4). Plates were then dried at room temperature and counted in a Wallac MicroBeta scintillation counter. Certain compounds of the present invention and their corresponding activity values are shown in TABLE B.

TABLE B

| Compound No. | IC$_{50}$ DOI Binding Assay (nM) |
| --- | --- |
| 24 | 36 |
| 42 | 11 |
| 52 | 4.6 |
| 66 | 4.8 |

Certain other compounds of the invention had activity values ranging from about 10 µM to about 1 nM in this assay.

Example 4: 5-HT$_{2A}$ Receptor Binding

Animals:

Animals (Sprague-Dawley rats) are sacrificed and brains are rapidly dissected and frozen in isopentane maintained at −42° C. Horizontal sections are prepared on a cryostat and maintained at −20° C.

LSD Displacement Protocol:

Lysergic acid diethylamide (LSD) is a potent 5-HT$_{2A}$ serotonin receptor and dopamine D$_2$ receptor ligand. An indication of the selectivity of compounds for either or both of these receptors involves displacement of radiolabeled-bound LSD from pre-treated brain sections. For these studies, radiolabeled $^{125}$I-LSD (NEN Life Sciences, Boston, Mass.; Catalog number NEX-199) can be utilized; spiperone (RBI, Natick, Mass.; Catalog number s-128) a 5-HT$_{2A}$ receptor and dopamine $D_2$ receptor antagonist, can also utilized. Buffer consists of 50 nanomolar TRIS-HCl, pH 7.4.

Brain sections are incubated in (a) Buffer plus 1 nanomolar $^{125}$I-LSD; (b) Buffer plus 1 nanomolar $^{125}$I-LSD and 1 micromolar spiperone; or Buffer plus 1 nanomolar $^{125}$I-LSD and 1 micromolar compound of interest for 30 min at room temperature. Sections are then washed 2×10 min at 4° C. in Buffer, followed by 20 s in distilled $H_2O$. Slides are then air-dried.

After drying, sections are apposed to x-ray film (Kodak Hyperfilm) and exposed for 4 days.

Example 5: In Vitro Human Platelet Aggregation Assays

Compounds of the invention were tested for their ability to aggregate human platelets. Aggregation assays were performed using a Chrono-Log Optical aggregometer model 410. Human blood (~100 mL) was collected from human donors into glass Vacutainers containing 3.8% sodium citrate (light blue tops) at room temperature. Platelet rich plasma (PRP) was isolated via centrifugation at 100 g for 15 min at room temperature. After removal of the aqueous PRP layer, the platelet poor plasma (PPP) was prepared via high speed centrifugation at 2400 g for 20 min. Platelets were counted and their concentration was set to 250,000 cells/L by dilution with PPP. Aggregation assays were conducted according to the manufacturer's specifications. Briefly, a suspension of 450 µL PRP was stirred in a glass cuvette (1200 rpm) and, after baseline was established, 1 µM ADP followed by either saline or 1 µM 5-HT and compound of interest (at desired concentrations) were added and the aggregation response recorded. The concentration of ADP used causes approximately 10-20% of maximal aggregation. The 5-HT concentration corresponded to the concentration which produced maximal potentiation. Percent inhibition of aggregation was calculated from the maximum decrease in optical density of the controls and of the samples containing inhibitors. Only the synergistic effect was assessed. Certain compounds of the invention had activity values ranging from about 80 µM to about 10 nM in this assay. Other compounds of the invention had activity values ranging from about 8 µM to about 10 nM in this assay.

Example 6: Inositol Phosphate (IP) Accumulation Assays

A. 5-HT$_{2A}$ Receptor

Compounds of the invention can be tested for their ability to activate a 5-HT$_{2A}$ receptor clone using an IP accumulation assay. Briefly, HEK293 cells are transiently transfected with a pCMV expression vector containing a human 5-HT$_{2A}$ receptor (for the sequence of the receptor see U.S. Pat. No. 6,541,209, SEQ ID NO:24). An IP accumulation assay can be performed as described below.

B. Constitutively Active 5-HT$_{2A}$ Receptor

Compounds of the invention can be tested for their ability to inhibit a constitutively active 5-HT$_{2A}$ receptor clone using an IP accumulation assay. Briefly, 293 cells are transiently transfected with a pCMV expression vector containing a constitutively active human 5-HT$_{2A}$ receptor (for the sequence of the receptor see U.S. Pat. No. 6,541,209, SEQ ID NO:30). The constitutively active human 5-HT$_{2A}$ receptor contained the human 5-HT$_{2A}$ receptor described in part A except that intracellular loop 3 (IC3) and the cytoplasmic tail are replaced by the corresponding human INI 5-HT$_{2C}$ cDNA. An IP accumulation assay can be performed as described below.

C. IP Accumulation Assay Protocol

On the day after transfections, medium is removed and the cells are washed with 5 mL PBS followed by careful aspiration. Cells are then trypsinized with 2 mL of 0.05% trypsin for 20-30 s followed by addition of 10 mL of warmed medium, gently titurated to dissociate cells, and an additional 13 mL of warmed medium was gently added. Cells are then counted and 55,000 cells are added to 96-well sterile poly-D-lysine treated plates. Cells are allowed to attach over a six hour incubation at 37° C. in a 5% $CO_2$ incubator. Medium is then carefully aspirated and 100 µL of warm inositol-free medium plus 0.5 Ci $^3$H-inositol are added to each well and the plates are incubated for 18-20 hours at 37° C. in a 5% $CO_2$ incubator.

On the next day, medium is carefully aspirated and then 0.1 mL of assay medium is added containing inositol-free/serum free medium, 10 µM pargyline, 10 mM lithium chloride, and test compound at indicated concentrations. The plates are then incubated for three hours at 37° C. and then wells are carefully aspirated. Then 200 µL of ice-cold 0.1M formic acid is added to each well. Plates can then be frozen at this point at −80° C. until further processed. Frozen plates are then thawed over the course of 1 h, and the contents of the wells (approximately 220 µL) are placed over 400 µL of washed ion-exchange resin (AG 1-X8) contained in a Multi Screen Filtration plate and incubated for 10 min followed by filtration under reduced pressure. Resin is then washed with 9×200 µL of water and then tritiated inositol phosphates (IP, IP2, and IP3) are eluted into a collecting plate by the addition of 200 µl of 1 M ammonium formate and an additional 10 min incubation. The eluent is then transferred to 20 mL scintillation vials, 8 mL of SuperMix or Hi-Safe scintillation cocktail is added, and vials are counted for 0.5-1 min in a Wallac 1414 scintillation counter.

Example 7: Efficacy of Compounds of the Invention in the Attenuation of DOI-Induced Hypolocomotion in Rats In this example, compounds of the invention were tested for inverse agonist activity by determining whether these compounds could attenuate DOI-induced hypolocomotion in rats in a novel environment. DOI is a potent 5-HT$_{2A/2C}$ receptor agonist that crosses the blood-brain barrier. The standard protocol used is described briefly below.

Animals:

Male Sprague-Dawley rats weighing between 200-350 g were used for all tests. Rats were housed three to four per cage.

Compounds:

(R)-DOI HCl ($C_{11}H_{16}INO_2$·HCl) was obtained from Sigma-Aldrich, and was dissolved in 0.9% saline. Compounds of the invention were synthesized at Arena Pharmaceuticals Inc., San Diego, Calif., and were dissolved in 100% PEG400. DOI was injected s.c. in a volume of 1 mL/kg, while compounds of the invention were administered p.o. in a volume of 1 mL/kg.

Procedure:

The "Motor Monitor" (Hamilton-Kinder, Poway, Calif.) was used for all activity measurement. This apparatus recorded rears using infrared photobeams.

Locomotor activity testing was conducted during the light cycle between 9:00 a.m. and 4:00 p.m. Animals were allowed 30 min acclimation to the testing room before testing began.

In determining the effects of compounds of the invention on DOI-induced hypoactivity, animals were first injected with vehicle or the compound of the invention (1-10 mg/kg) in their home cages. Twenty five minutes later, saline or DOI (1 mg/kg salt) was injected. Ten minutes after DOI administration, animals were placed into the activity apparatus and rearing activity was measured for 10 min.

Figure 5:
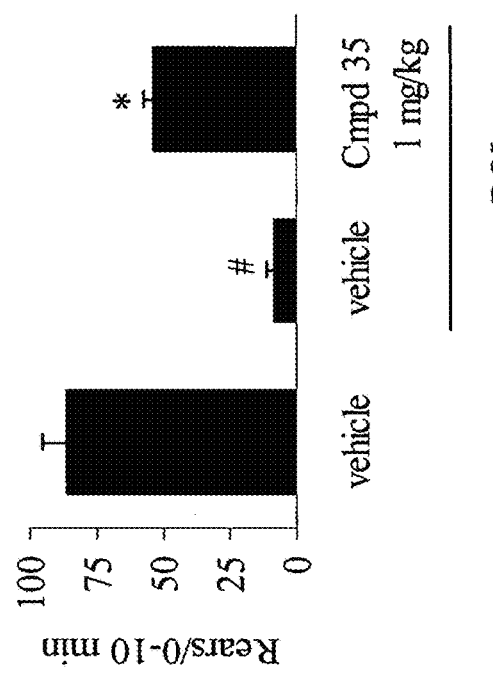
FIG. 5 shows the efficacy of compound 35 in the attenuation of DOI-induced hypolocomotion in rats.
Figure 6:
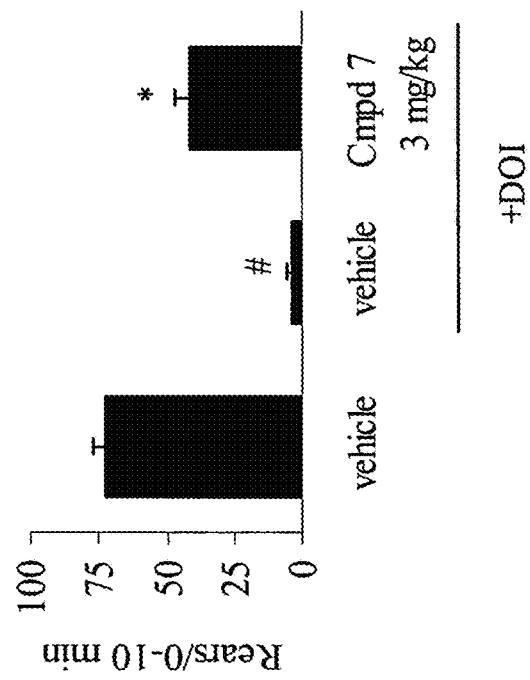
FIG. 6 shows the efficacy of compound 7 in the attenuation of DOI-induced hypolocomotion in rats.

Statistics and Results:

Results (total rears over 10 minutes) were analyzed by t-test. $P<0.05$ was considered significant. As shown in FIG. 5, compound 35 attenuated DOI-induced hypolocomotion in rats. In addition, as shown in FIG. 6, compound 7 also attenuated DOI-induced hypolocomotion in rats.

Example 8: Serotonin 5-HT$_{2A}$ Receptor Occupancy Studies in Monkey

In this example, the 5-HT$_{2A}$ receptor occupancy of a compound of the invention can be measured. The study can be carried out in rhesus monkeys using PET and $^{18}$F-altanserin.

Radioligand:

The PET radioligand used for the occupancy studies is $^{18}$F-altanserin. Radiosynthesis of $^{18}$F-altanserin is achieved in high specific activities and is suitable for radiolabeling 5-HT$_{2A}$ receptors in vivo (see Staley et al., *Nucl. Med. Biol.*, 28:271-279 (2001) and references cited within). Quality control issues (chemical and radiochemical purity, specific activity, stability etc) and appropriate binding of the radioligand are verified in rat brain slices prior to use in PET experiments.

Drug Doses and Formulations:

Briefly, the radiopharmaceutical is dissolved in sterile 0.9% saline, pH approx 6-7. The compounds of the invention are dissolved in 60% PEG 400-40% sterile saline on the same day of the PET experiment.

Serotonin 5-HT$_{2A}$ occupancy studies in humans have been reported for M100,907 (Grunder et al., *Neuropsychopharmacology*, 17:175-185 (1997), and Talvik-Lofti et al., *Psychopharmacology*, 148:400-403 (2000)). High occupancies of the 5-HT$_{2A}$ receptors have been reported for various oral doses (doses studied ranged from 6 to 20 mg). For example, an occupancy of >90% was reported for a dose of 20 mg (Talvik-Lofti et al., supra), which translates to approx. 0.28 mg/kg. It may therefore be anticipated that an i.v. dose of 0.1 to 0.2 mg/kg of M100,907 is likely to provide high receptor occupancy. A 0.5 mg/kg dose of a compound of the invention can be used in these studies.

PET Experiments:

The monkey is anesthetized by using ketamine (10 mg/kg) and is maintained using 0.7 to 1.25% isoflurane. Typically, the monkey has two i.v. lines, one on each arm. One i.v. line is used to administer the radioligand, while the other line is used to draw blood samples for pharmacokinetic data of the radioligand as well as the cold drugs. Generally, rapid blood samples are taken as the radioligand is administered which then taper out by the end of the scan. A volume of approximately 1 mL of blood is taken per time point, which is spun down, and a portion of the plasma is counted for radioactivity in the blood.

An initial control study is carried out in order to measure baseline receptor densities. PET scans on the monkey are separated by at least two weeks. Unlabeled Compound of the invention is administered intravenously, dissolved in 80% PEG 400:40% sterile saline.

PET Data Analysis:

PET data are analyzed by using cerebellum as the reference region and using the distribution volume region (DVR) method. This method has been applied for the analysis of $^{18}$F-altanserin PET data in nonhuman primate and human studies (Smith et al., *Synapse*, 30:380-392 (1998)).

Example 9: The Effect of Compounds of the Invention and Zolpidem on Delta Power in Rats In this example, the effect of compounds of the invention on sleep and wakefulness can be compared to the reference drug zolpidem. Drugs are administered during the middle of the light period (inactivity period).

Briefly, compounds of the invention are tested for their effects on sleep parameters and are compared to zolpidem (5.0 mg/kg, Sigma, St. Louis, Mo.) and vehicle control (80% Tween 80, Sigma, St. Louis, Mo.). A repeated measures design is employed in which each rat is to receive seven separate dosings via oral gavage. The first and seventh dosings are vehicle and the second through sixth are the test compounds and zolpidem given in counter-balanced order. Since all dosings are administered while the rats are connected to the recording apparatus, 60% CO$_2$/40% O$_2$ gas is employed for light sedation during the oral gavage process. Rats are fully recovered within 60 seconds following the procedure. A minimum of three days elapses between dosings. In order to test the effect of the compounds on sleep consolidation, dosing occurs during the middle of the rats' normal inactive period (6 h following lights on). Dosing typically occurs between 13:15 and 13:45 using a 24 hour notation. All dosing solutions are made fresh on the day of dosing. Following each dosing, animals are continuously recorded until lights out the following day (~30 h).

Animal Recording and Surgical Procedures:

Animals are housed in a temperature controlled recording room under a 12/12 light/dark cycle (lights on at 7:00 am) and have food and water available ad libitum. Room temperature (24±2° C.), humidity (50±20% relative humidity) and lighting conditions are monitored continuously via computer. Drugs are administered via oral gavage as described above, with a minimum of three days between dosings. Animals are inspected daily in accordance with NIH guidelines.

Eight male Wistar rats (300±25 g; Charles River, Wilmington, Mass.) are prepared with chronic recording implants for continuous electroencephalograph (EEG) and electromyograph (EMG) recordings. Under isoflurane anesthesia (1-4%), the fur is shaved from the top of the skull and the skin was disinfected with Betadine and alcohol. A dorsal midline incision is made, the temporalis muscle retracted, and the skull cauterized and thoroughly cleaned with a 2% hydrogen peroxide solution. Stainless steel screws (#000) are implanted into the skull and served as epidural electrodes. EEG electrodes are positioned bilaterally at +2.0 mm AP from bregma and 2.0 mm ML and at −6.0 mm AP and 3.0 mm ML. Multi-stranded twisted stainless steel wire electrodes are sutured bilaterally in the neck muscles for recording of the EMG. EMG and EEG electrodes are soldered to a head plug connector that was affixed to the skull with dental acrylic. Incisions are closed with suture (silk 4-0) and antibiotics administered topically. Pain is relieved by a long-lasting analgesic (buprenorphine) administered intramuscularly once post-operatively. Post-surgery, each animal is placed in a clean cage and observed until it is recovered. Animals are permitted a minimum of one week post-operative recovery before study.

For sleep recordings, animals are connected via a cable and a counter-balanced commutator to a Neurodata model 15 data collection system (Grass-Telefactor, West Warwick, R.I.). The animals are allowed an acclimation period of at least 48 hours before the start of the experiment and are connected to the recording apparatus continuously throughout the experimental period except to replace damaged cables. The amplified EEG and EMG signals are digitized and stored on a computer using SleepSign software (Kissei Comtec, Irvine, Calif.).

Data Analysis:

EEG and EMG data are scored visually in 10 s epochs for waking (W), REMS and NREMS. Scored data are analyzed and expressed as time spent in each state per half hour. Sleep bout length and number of bouts for each state are calculated in hourly bins. A "bout" consists of a minimum of two consecutive epochs of a given state. EEG delta power (0.5-3.5 Hz) within NREMS is also analyzed in hourly bins. The EEG spectra during NREMS are obtained offline with a fast Fourier transform algorithm on all epochs without artifact. The delta power is normalized to the average delta power in NREMS between 23:00 and 1:00, a time when delta power is normally lowest.

Data are analyzed using repeated measures ANOVA. Light phase and dark phase data are analyzed separately. Both the treatment effect within each rat and the time by treatment effect within each rat is analyzed. Since two comparisons are made, a minimum value of $P<0.025$ is required for post hoc analysis. When statistical significance is found from the ANOVAs, t-tests are performed comparing all compounds to vehicle and the test compounds to zolpidem.

Example 10: Efficacy of Compounds of the Invention in the Inhibition of JC Virus Infection of Human Glial Cells A compound of the invention can be shown to inhibit JC virus infection of human glial cells using the in vitro model of Elphick et al. [*Science* (2004) 306:1380-1383], essentially as described briefly here.

Cells and JC Virus

The human glial cell line SVG (or a suitable subclone thereof, such as SVG-A) is used for these experiments. SVG is a human glial cell line established by transformation of human fetal glial cells by an origin defective SV40 mutant [Major et al., *Proc. Natl. Acad. Sci. USA* (1985) 82:1257-1261]. SVG cells are cultured in Eagle's minimum essential medium (Mediatech Inc., Herndon, Va.) supplemented with 10% heat-inactivated fetal bovine serum, and kept in a humidified 37° C. 5% $CO_2$ incubator.

The Mad-1/SVEΔ strain of JC virus [Vacante et al., *Virology* (1989) 170:353-361] is used for these experiments. While the host range of JC virus is typically limited to growth in human fetal glial cells, the host range of Mad-1/SVEΔ extends to human kidney and monkey cell types. Mad-1/SVEΔ is propagated in HEK cells. Virus titer is measured by hemagglutination of human type O erythrocytes.

Assay for Inhibition of JC Virus Infection

SVG cells growing on coverslips are pre-incubated at 37° C. for 45 min with or without the compound of the invention diluted in media containing 2% FCS. By way of illustration and not limitation, the compound of the invention is used at a concentration of about 1 nM to about 100 μM, at a concentration of about 10 nM to about 100 μM, at a concentration of about 1 nM to about 10 μM, or at a concentration of about 10 nM to about 10 μM.

JC virus (Mad-1/SVEΔ) is then added at an MOI of 1.0 and the cells are incubated for 1 h at 37° C. in the continued presence of the compound of the invention. The cells are then washed 3× in PBS and fed with growth media containing the compound of the invention. At 72 h post-infection, V antigen positive cells are scored by indirect immunofluorescence (see below). Controls include the addition of the compound of the invention at 24 and 48 h post-infection. The percentage of infected cells in untreated cultures is set at 100%.

Indirect Immunofluorescence

For indirect immunofluorescence analysis of V antigen expression, SVG cells growing on coverslips are fixed in ice cold acetone. To detect V antigen expression, the cells are then incubated for 30 min at 37° C. with a 1:10 dilution of hybridoma supernatant from PAB597. The PAB597 hybridoma produces a monoclonal antibody against the SV40 capsid protein VP1 which has been shown to cross-react with JC virus VP1. The cells are then washed and incubated with goat anti-mouse Alexa Fluor 488 secondary antibody for an additional 30 min. After a final wash, the cells are counterstained with 0.05% Evan's blue, mounted onto glass slides using 90% glycerol in PBS and visualized on Nikon E800 epifluorescent scope. Images are captured using a Hamamatsu digital camera and analyzed using Improvision software.

Example 11: In Vitro Dog Platelet Aggregation Assays

Approximately 50 mL of blood is pooled from 3 male beagles. The protocol for analyzing the effects of compounds on platelet aggregation are identical to those used for human platelets (see Example 5, supra) except 5 μM ADP and 2 μM 5-HT were used to stimulate amplification of platelet aggregation.

Example 12: Ex-Vivo Dog Whole Blood Aggregation

One hour following p.o. dosing with a test compound whole blood is collected from male beagle dogs in a 5 mL Vacutainer with exogenous heparin (5 U/mL) added to the Vacutainer. Aggregation studies are evaluated by using a whole blood Aggregometer (Chronolog Corp.). Briefly, whole blood (400 μL) is added to saline (600 μL) with constant stirring and activated with 5 μg of Collagen (Chronolog Corp.). The serotonin response is obtained by adding 5-HT (Sigma) to a final concentration of 2.5 μM.

Results:

Selected compounds are tested for anti-platelet aggregation activity after single bolus oral dosing. The dose that affords maximal inhibition of 5-HT amplified platelet aggregation is identified and used for comparison.

Example 13: Rat In Vivo Thrombosis, Bleeding, Aggregation, PK Assay

Thrombosis Formation and Bleeding Time:

This model concomitantly measures thrombus formation, bleeding time, platelet aggregation and drug exposure in a single live dosed rat. Test compounds are administered to male rats (weighing 250-350 g) via p.o. injection at varying concentrations depending on compound potency ranging from 1 mg/kg-100 mg/kg. Animals are then anesthetized using Nembutal approximately 30 min post administration. Once the animal is fully anesthetized using approved surgical techniques the animal's right femoral artery is isolated in 2 different sections approximately 4-6 mm in length, one area for probe placement and one for ferric chloride patch positioning. The artery is then allowed to stabilize to allow recovery from the surgery. During stabilization the animal is then intubated and placed on a ventilator (Harvard Apparatus, Inc.) at 75 strokes/min with a volume of 2.5 cm$^3$. Following intubation and after stabilization a micro arterial probe (Transonic Systems, Inc.) is then placed on the distal isolated femoral artery. Once the probe is in place the flow is monitored using a Powerlab recording system (AD Instruments) to monitor rate of pulsatile flow. A small piece of filter paper soaked in 30% ferric chloride is placed on the area of the artery upstream of the probe for 10 min. After 5 min of ferric chloride patch placement the last 3 mm of the rat's tail is removed. The tail is then placed in a saline filled glass vial at 37° C. and the time it took for bleeding to stop is recorded. After the ferric chloride patch is removed the flow is recorded until the artery is occluded and the time to occlusion is recorded.

Whole Blood Aggregation and PK:

Following measurement of bleeding and time to occlusion 5 mL of blood is obtained for ex vivo aggregation analysis by cardiac puncture in heparin (5 U/mL). An additional 500 µL of blood is collected in a separate Vacutainer for PK analysis (plasma drug concentration). Ex vivo aggregation studies are evaluated by using a whole blood Aggregometer (Chronolog Corp.). Briefly, whole blood (400 µL) is added to saline (600 µL) with constant stirring and activated with 2.55 µg of Collagen (Chronolog Corp.). The serotonin response is obtained by adding 5-HT (Sigma) to a final concentration of 2.5 µM.

Results:

Test compounds or reference compounds with acceptable levels of binding to rat 5-HT$_{2A}$ serotonin receptors are evaluated for effects of thrombus formation, bleeding and platelet activity in a single model. This allows for the most accurate demonstration of separation of the test compound effects on platelet mediated thrombus formation from effects on bleeding.

Those skilled in the art will recognize that various modifications, additions, substitutions, and variations to the illustrative examples set forth herein can be made without departing from the spirit of the invention and are, therefore, considered within the scope of the invention. All documents referenced above, including, but are not limited to, printed publications, and provisional and regular patent applications, are incorporated herein by reference in their entirety.

What is claimed is:

1. A method for treating a 5-HT$_{2A}$ mediated disorder in an individual in need thereof comprising administering to said individual a therapeutically effective amount of a compound selected from the group consisting of 2-[4-(4-bromo-1-methyl-1-H-pyrazole-3-carbonyl)-piperazin-1-yl]-1-(4-fluoro-phenyl)-ethanone, 2-[4-(4-chloro-1-methyl-1-H-pyrazole-3-carbonyl)-piperazin-1-yl]-1-(4-fluoro-phenyl)-ethanone, and 2-[(S)-4-(4-chloro-1-methyl-1-H-pyrazole-3-carbonyl)-3-methyl-piperazin-1-yl]-1-(4-fluoro-phenyl)-ethanone or a pharmaceutically acceptable salt, solvate, or hydrate thereof, wherein the 5-HT$_{2A}$ mediated disorder is selected from the group consisting of agitation, dementia, Alzheimer's disease, Lewy Body disease, Parkinson's disease, Huntington's disease, platelet aggregation, reducing the risk of blood clot formation, treating a diabetic-related disorder, treating progressive multifocal leukoencephalopathy, hypertension, pain, and sleep disorders.

2. A method for treating a sleep disorder in an individual in need thereof comprising administering to said individual a therapeutically effective amount of a compound selected from the group consisting of 2-[4-(4-bromo-1-methyl-1-H-pyrazole-3-carbonyl)-piperazin-1-yl]-1-(4-fluoro-phenyl)-ethanone, 2-[4-(4-chloro-1-methyl-1-H-pyrazole-3-carbonyl)-piperazin-1-yl]-1-(4-fluoro-phenyl)-ethanone, and 2-[(S)-4-(4-chloro-1-methyl-1-H-pyrazole-3-carbonyl)-3-methyl-piperazin-1-yl]-1-(4-fluoro-phenyl)-ethanone or a pharmaceutically acceptable salt, solvate, or hydrate thereof.

3. The method according to claim 2, wherein said sleep disorder is a dyssomnia.

4. The method according to claim 2, wherein said sleep disorder is insomnia.

5. The method according to claim 2, wherein said sleep disorder is a parasomnia.

6. A method for increasing slow wave sleep in an individual in need thereof comprising administering to said individual a therapeutically effective amount of a compound selected from the group consisting of 2-[4-(4-bromo-1-methyl-1-H-pyrazole-3-carbonyl)-piperazin-1-yl]-1-(4-fluoro-phenyl)-ethanone, 2-[4-(4-chloro-1-methyl-1-H-pyrazole-3-carbonyl)-piperazin-1-yl]-1-(4-fluoro-phenyl)-ethanone, and 2-[(S)-4-(4-chloro-1-methyl-1-H-pyrazole-3-carbonyl)-3-methyl-piperazin-1-yl]-1-(4-fluoro-phenyl)-ethanone or a pharmaceutically acceptable salt, solvate, or hydrate thereof.

7. A method for improving sleep consolidation in an individual in need thereof comprising administering to said individual a therapeutically effective amount of a compound selected from the group consisting of 2-[4-(4-bromo-1-methyl-1-H-pyrazole-3-carbonyl)-piperazin-1-yl]-1-(4-fluoro-phenyl)-ethanone, 2-[4-(4-chloro-1-methyl-1-H-pyrazole-3-carbonyl)-piperazin-1-yl]-1-(4-fluoro-phenyl)-ethanone, and 2-[(S)-4-(4-chloro-1-methyl-1-H-pyrazole-3-carbonyl)-3-methyl-piperazin-1-yl]-1-(4-fluoro-phenyl)-ethanone or a pharmaceutically acceptable salt, solvate, or hydrate thereof.

8. A method for improving sleep maintenance in an individual in need thereof comprising administering to said individual a therapeutically effective amount of a compound selected from the group consisting of 2-[4-(4-bromo-1-methyl-1-H-pyrazole-3-carbonyl)-piperazin-1-yl]-1-(4-fluoro-phenyl)-ethanone, 2-[4-(4-chloro-1-methyl-1-H-pyrazole-3-carbonyl)-piperazin-1-yl]-1-(4-fluoro-phenyl)-ethanone, and 2-[(S)-4-(4-chloro-1-methyl-1-H-pyrazole-3-carbonyl)-3-methyl-piperazin-1-yl]-1-(4-fluoro-phenyl)-ethanone or a pharmaceutically acceptable salt, solvate, or hydrate thereof.

9. A method for treating agitation an individual in need thereof comprising administering to said individual a therapeutically effective amount of a compound selected from the group consisting of 2-[4-(4-bromo-1-methyl-1-H-pyrazole-3-carbonyl)-piperazin-1-yl]-1-(4-fluoro-phenyl)-ethanone, 2-[4-(4-chloro-1-methyl-1-H-pyrazole-3-carbonyl)-piperazin-1-yl]-1-(4-fluoro-phenyl)-ethanone, and 2-[(S)-4-(4-chloro-1-methyl-1-H-pyrazole-3-carbonyl)-3-methyl-piperazin-1-yl]-1-(4-fluoro-phenyl)-ethanone or a pharmaceutically acceptable salt, solvate, or hydrate thereof.

10. The method of claim 9, wherein the agitation is due to a psychiatric disorder other than dementia.

11. A method for the treatment of agitation or a symptom thereof in an individual in need thereof suffering from dementia comprising administering to said individual a therapeutically effective amount of a compound selected from the group consisting of 2-[4-(4-bromo-1-methyl-1-H-pyrazole-3-carbonyl)-piperazin-1-yl]-1-(4-fluoro-phenyl)-ethanone, 2-[4-(4-chloro-1-methyl-1-H-pyrazole-3-carbonyl)-piperazin-1-yl]-1-(4-fluoro-phenyl)-ethanone, and 2-[(S)-4-(4-chloro-1-methyl-1-H-pyrazole-3-carbonyl)-3-methyl-piperazin-1-yl]-1-(4-fluoro-phenyl)-ethanone or a pharmaceutically acceptable salt, solvate, or hydrate thereof.

12. The method of claim 11, wherein the dementia is due to a degenerative disease of the nervous system.

13. The method of claim 11, wherein the dementia is selected from the group consisting of Alzheimer's disease, Lewy Body, Parkinson's disease, Huntington's disease, dementia due to diseases that affect blood vessels, and any combination thereof.

14. A method of treating agitation or a symptom thereof in an individual in need thereof, where the individual is a cognitively intact elderly patient, comprising administering to said individual a therapeutically effective amount of a compound selected from the group consisting of 2-[4-(4-bromo-1-methyl-1-H-pyrazole-3-carbonyl)-piperazin-1-yl]-1-(4-fluoro-phenyl)-ethanone, 2-[4-(4-chloro-1-methyl-1-H-pyrazole-3-carbonyl)-piperazin-1-yl]-1-(4-fluoro-phenyl)-ethanone, and 2-[(S)-4-(4-chloro-1-methyl-1-H-pyrazole-3-carbonyl)-3-methyl-piperazin-1-yl]-1-(4-fluoro-phenyl)-ethanone or a pharmaceutically acceptable salt, solvate, or hydrate thereof.

15. A method for treating a condition associated with platelet aggregation in an individual in need thereof comprising administering to said individual a therapeutically effective amount of a compound selected from the group consisting of 2-[4-(4-bromo-1-methyl-1-H-pyrazole-3-carbonyl)-piperazin-1-yl]-1-(4-fluoro-phenyl)-ethanone, 2-[4-(4-chloro-1-methyl-1-H-pyrazole-3-carbonyl)-piperazin-1-yl]-1-(4-fluoro-phenyl)-ethanone, and 2-[(S)-4-(4-chloro-1-methyl-1-H-pyrazole-3-carbonyl)-3-methyl-piperazin-1-yl]-1-(4-fluoro-phenyl)-ethanone or a pharmaceutically acceptable salt, solvate, or hydrate thereof.

16. A method for reducing the risk of blood clot formation in an angioplasty or coronary bypass surgery individual in need thereof comprising administering to said individual a therapeutically effective amount of a compound selected from the group consisting of 2-[4-(4-bromo-1-methyl-1-H-pyrazole-3-carbonyl)-piperazin-1-yl]-1-(4-fluoro-phenyl)-ethanone, 2-[4-(4-chloro-1-methyl-1-H-pyrazole-3-carbonyl)-piperazin-1-yl]-1-(4-fluoro-phenyl)-ethanone, and 2-[(S)-4-(4-chloro-1-methyl-1-H-pyrazole-3-carbonyl)-3-methyl-piperazin-1-yl]-1-(4-fluoro-phenyl)-ethanone or a pharmaceutically acceptable salt, solvate, or hydrate thereof.

17. A method for reducing the risk of blood clot formation in an individual in need thereof comprising administering to said individual a therapeutically effective amount of a compound selected from the group consisting of 2-[4-(4-bromo-1-methyl-1-H-pyrazole-3-carbonyl)-piperazin-1-yl]-1-(4-fluoro-phenyl)-ethanone, 2-[4-(4-chloro-1-methyl-1-H-pyrazole-3-carbonyl)-piperazin-1-yl]-1-(4-fluoro-phenyl)-ethanone, and 2-[(S)-4-(4-chloro-1-methyl-1-H-pyrazole-3-carbonyl)-3-methyl-piperazin-1-yl]-1-(4-fluoro-phenyl)-ethanone or a pharmaceutically acceptable salt, solvate, or hydrate thereof.

18. A method for reducing the risk of blood clot formation in an individual in need thereof suffering from atrial fibrillation, comprising administering to said individual a therapeutically effective amount of a compound selected from the group consisting of 2-[4-(4-bromo-1-methyl-1-H-pyrazole-3-carbonyl)-piperazin-1-yl]-1-(4-fluoro-phenyl)-ethanone, 2-[4-(4-chloro-1-methyl-1-H-pyrazole-3-carbonyl)-piperazin-1-yl]-1-(4-fluoro-phenyl)-ethanone, and 2-[(S)-4-(4-chloro-1-methyl-1-H-pyrazole-3-carbonyl)-3-methyl-piperazin-1-yl]-1-(4-fluoro-phenyl)-ethanone or a pharmaceutically acceptable salt, solvate, or hydrate thereof.

19. A method for treating a diabetic-related disorder in an individual in need thereof comprising administering to said individual a therapeutically effective amount of a compound selected from the group consisting of 2-[4-(4-bromo-1-methyl-1-H-pyrazole-3-carbonyl)-piperazin-1-yl]-1-(4-fluoro-phenyl)-ethanone, 2-[4-(4-chloro-1-methyl-1-H-pyrazole-3-carbonyl)-piperazin-1-yl]-1-(4-fluoro-phenyl)-ethanone, and 2-[(S)-4-(4-chloro-1-methyl-1-H-pyrazole-3-carbonyl)-3-methyl-piperazin-1-yl]-1-(4-fluoro-phenyl)-ethanone or a pharmaceutically acceptable salt, solvate, or hydrate thereof.

20. A method for treating progressive multifocal leukoencephalopathy in an individual in need thereof comprising administering to said individual a therapeutically effective amount of a compound selected from the group consisting of 2-[4-(4-bromo-1-methyl-1-H-pyrazole-3-carbonyl)-piperazin-1-yl]-1-(4-fluoro-phenyl)-ethanone, 2-[4-(4-chloro-1-methyl-1-H-pyrazole-3-carbonyl)-piperazin-1-yl]-1-(4-fluoro-phenyl)-ethanone, and 2-[(S)-4-(4-chloro-1-methyl-1-H-pyrazole-3-carbonyl)-3-methyl-piperazin-1-yl]-1-(4-fluoro-phenyl)-ethanone or a pharmaceutically acceptable salt, solvate, or hydrate thereof.

21. A method for treating hypertension in an individual in need thereof comprising administering to the individual a therapeutically effective amount of a compound selected from the group consisting of 2-[4-(4-bromo-1-methyl-1-H-pyrazole-3-carbonyl)-piperazin-1-yl]-1-(4-fluoro-phenyl)-ethanone, 2-[4-(4-chloro-1-methyl-1-H-pyrazole-3-carbonyl)-piperazin-1-yl]-1-(4-fluoro-phenyl)-ethanone, and 2-[(S)-4-(4-chloro-1-methyl-1-H-pyrazole-3-carbonyl)-3-methyl-piperazin-1-yl]-1-(4-fluoro-phenyl)-ethanone or a pharmaceutically acceptable salt, solvate, or hydrate thereof.

22. A method for treating pain in an individual in need thereof comprising administering to the individual a therapeutically effective amount of a compound selected from the group consisting of 2-[4-(4-bromo-1-methyl-1-H-pyrazole-3-carbonyl)-piperazin-1-yl]-1-(4-fluoro-phenyl)-ethanone, 2-[4-(4-chloro-1-methyl-1-H-pyrazole-3-carbonyl)-piperazin-1-yl]-1-(4-fluoro-phenyl)-ethanone, and 2-[(S)-4-(4-chloro-1-methyl-1-H-pyrazole-3-carbonyl)-3-methyl-piperazin-1-yl]-1-(4-fluoro-phenyl)-ethanone or a pharmaceutically acceptable salt, solvate, or hydrate thereof.

* * * * *